United States Patent
Winqvist et al.

(12) 
(10) Patent No.: US 10,401,357 B2
(45) Date of Patent: Sep. 3, 2019

(54) TREATING CANCER

(71) Applicant: TLA TARGETED IMMUNOTHERAPIES AB, Stockholm (SE)

(72) Inventors: Ola Winqvist, Uppsala (SE); Graham Cotton, Edinburgh (GB)

(73) Assignee: TLA TARGETED IMMUNOTHERAPIES AB, Stockholm (SE)

( * ) Notice: Subject to any disclaimer, the term of this patent is extended or adjusted under 35 U.S.C. 154(b) by 0 days.

(21) Appl. No.: 15/629,708

(22) Filed: Jun. 21, 2017

(65) Prior Publication Data

US 2018/0038860 A1 Feb. 8, 2018

Related U.S. Application Data

(60) Division of application No. 14/105,628, filed on Dec. 13, 2013, now Pat. No. 9,726,666, which is a continuation-in-part of application No. PCT/GB2012/051357, filed on Jun. 13, 2012, and a continuation-in-part of application No. PCT/GB2012/051349, filed on Jun. 13, 2012, and a continuation-in-part of application No. PCT/BG2012/051348, filed on Jun. 13, 2012, and a continuation-in-part of application No. PCT/GB2012/051351, filed on Jun. 13, 2012, and a continuation-in-part of application No. PCT/GB2012/051350, filed on Jun. 13, 2012, and a continuation-in-part of application No. PCT/GB2012/051355, filed on Jun. 13, 2012, and a continuation-in-part of application No. PCT/GB2012/051345, filed on Jun. 13, 2012, and a continuation-in-part of application No. PCT/GB2012/051352, filed on Jun. 13, 2012, and a continuation-in-part of application No. PCT/GB2012/051346, filed on Jun. 13, 2012, and a continuation-in-part of application No. PCT/GB2012/051353, filed on Jun. 13, 2012, and a continuation-in-part of application No. PCT/GB2012/051356, filed on Jun. 13, 2012, and a continuation-in-part of application No. PCT/GB2012/051354, filed on Jun. 13, 2012.

(60) Provisional application No. 61/496,442, filed on Jun. 13, 2011, provisional application No. 61/496,167, filed on Jun. 13, 2011, provisional application No. 61/496,288, filed on Jun. 13, 2011, provisional application No. 61/496,242, filed on Jun. 13, 2011, provisional application No. 61/496,209, filed on Jun. 13, 2011, provisional application No. 61/496,195, filed on Jun. 13, 2011, provisional application No. 61/496,228, filed on Jun. 13, 2011, provisional application No. 61/496,264, filed on Jun. 13, 2011, provisional application No. 61/496,184, filed on Jun.

(Continued)

(51) Int. Cl.
| | |
|---|---|
| *A61K 39/00* | (2006.01) |
| *A61K 39/395* | (2006.01) |
| *A61K 39/40* | (2006.01) |
| *A61M 37/00* | (2006.01) |
| *G01N 33/566* | (2006.01) |
| *A61M 1/36* | (2006.01) |
| *G01N 33/569* | (2006.01) |

(52) U.S. Cl.
CPC ......... *G01N 33/566* (2013.01); *A61M 1/3618* (2014.02); *A61M 1/3679* (2013.01); *G01N 33/56972* (2013.01); *G01N 2333/70596* (2013.01); *G01N 2333/7158* (2013.01); *G01N 2800/065* (2013.01)

(58) Field of Classification Search
None
See application file for complete search history.

(56) References Cited

U.S. PATENT DOCUMENTS 8,658,377 B2 2/2014 Lillard et al.
2003/0017979 A1 1/2003 Mack
(Continued)

FOREIGN PATENT DOCUMENTS

DE 102005036505 A1 6/2006
EP 1255112 A2 11/2002
(Continued)

OTHER PUBLICATIONS

Lopez-Giral et al. 2004. J. Leukoc. Biol. 76:462-471 (Year: 2004).*
(Continued)

*Primary Examiner* — Shulamith H Shafer
(74) *Attorney, Agent, or Firm* — Michael Best & Friedrich LLP

(57) ABSTRACT

A method for treating cancer comprising applying peripheral blood from a patient or subject to an apheresis column loaded with a solid support comprising one or more binding reagents capable of specifically binding to a chemokine receptor, optionally the chemokine receptor CCR7, CCR5, CCR6, CCR8, CXCR4, CXCR7, CCR4, CCR9, CCR10, CXCR3 or CXCR5 or to a Treg receptor immobilized directly or indirectly on the support thus removing one or more chemokine receptor, optionally CCR7, CCR5, CCR6, CCR8, CXCR4, CXCR7, CCR4, CCR9, CCR10, CXCR3 or CXCR5 or Treg receptor expressing cells from the peripheral blood of the patient or subject. Various companion diagnostic methods and useful binding reagents are also described.

12 Claims, 9 Drawing Sheets

Specification includes a Sequence Listing.

Related U.S. Application Data 13, 2011, provisional application No. 61/496,329, filed on Jun. 13, 2011, provisional application No. 61/496,377, filed on Jun. 13, 2011, provisional application No. 61/496,352, filed on Jun. 13, 2011.

(56) References Cited

U.S. PATENT DOCUMENTS

| | | |
|---|---|---|
| 2003/0215421 A1 | 11/2003 | McDonald |
| 2004/0077835 A1 | 4/2004 | Offord |
| 2007/0092484 A1 | 4/2007 | Levine |
| 2009/0196823 A1 | 8/2009 | Cornelius et al. |
| 2010/0029753 A1 | 2/2010 | Anderson |
| 2011/0081407 A1 | 4/2011 | Lillard et al. |

FOREIGN PATENT DOCUMENTS

| | | |
|---|---|---|
| EP | 1783227 A1 | 5/2007 |
| EP | 2067495 A1 | 6/2009 |
| EP | 2118060 B1 | 10/2010 |
| WO | WO-0125492 A1 | 4/2001 |
| WO | WO-0140306 A1 | 6/2001 |
| WO | WO-2004026893 A2 | 4/2004 |
| WO | WO-2004045526 A2 | 6/2004 |
| WO | WO-050088 A2 | 1/2005 |
| WO | WO-2005037305 A1 | 4/2005 |
| WO | 2005/084667 | 9/2005 |
| WO | WO-2006052723 A2 | 5/2006 |
| WO | WO-2006125201 A2 | 11/2006 |
| WO | WO-2006126209 A1 | 11/2006 |
| WO | WO-2007024705 A2 | 3/2007 |
| WO | 2007/053082 | 5/2007 |
| WO | WO-2007133147 A1 | 11/2007 |
| WO | WO-2008059066 A1 | 5/2008 |
| WO | WO-2008142405 A1 | 11/2008 |
| WO | WO-2010021697 A2 | 2/2010 |
| WO | WO-2010029317 A2 | 3/2010 |
| WO | WO-2010103517 A1 | 9/2010 |
| WO | WO-2010142952 A2 | 12/2010 |
| WO | WO-2011017120 A1 | 2/2011 |
| WO | WO-2012112724 A1 | 8/2012 |

OTHER PUBLICATIONS

Alfonso-Perez et al. 2006.J. Leukoc. Biol. 79:1157-1165 (Year: 2006).*
Till et al. 2002. Blood. 99:2977-2984 (Year: 2002).*
Allen, et al., "A Rapid and Efficient Way to Obtain Modified Chemokines for Functional and Biophysical Studies", Cytokine, vol. 55, No. 2, May 2, 2011, 168-173.
An, et al., "Immunohistochemical Detection of CCR2 and CX3CR1 in Sepsis-Induced Lung Injury", Forensic Science International, Nov. 20, 2009, e21-e25.
Autschbach, et al., "Expression of Chemokine Receptors in Normal and Inflamed Human Intestine, Tonsil, and Liver", Cellular Immunology, vol. 236, Sep. 23, 2005, 110-114.
Bellani, et al., "Altered MRNA Levels of Chemokines and Cytokines in Schizophrenia and Bipolar Disorder", Schizophrenia Research, vol. 117, No. 2-3, Apr. 1, 2010, 251-252.
Beumer, et al., "Increased Level of Serum Cytokines, Chemokines and Adipokines in Patients with Schizophrenia is Associated with Disease and Metabolic Syndrome", Psychoneuroendocrinology, Apr. 1, 2012, 1901-1911.
Borchers, et al., "Lymphocyte Recruitment and Homing to the Liver in Primary Biliary Cirrhosis and Primary Sclerosing Cholangitis", Seminars in Immunopathology, vol. 31, No. 3, Jun. 17, 2009, 309-322.
Bossink, et al., "Plasma Levels of the Chemokines Monocyte Chemotactic Protein-1 and -2 are Elevated in Human Sepsis", Blood, vol. 86, No. 10, Nov. 15, 1995, 3841-3847.
Cancello, et al., "Review Article: Is Obesity an Inflammatory Illness? Role of Low-Grade Inflammation and Macrophage Infiltration in Human White Adipose Tissue", BJOG: An International Journal of Obstetrics and Gynecology, vol. 113, No. 10, Oct. 1, 2006, 1141-1147.
Chantry, et al., "Chemokines in Allergy", Current Drug Targets—Inflammation & Allergy, vol. 1, No. 1, Jan. 1, 2002, 109-116.
Charo, et al., "Chemokines in the Pathogenesis of Vascular Disease", Circulation Research, vol. 95, No. 9, Oct. 29, 2004, 858-866.
Chinese Office Action for Chinese Patent Application No. 2012800396667, English translation only provided to Applicant, dated Jun. 17, 2015, 8 pages.
Coillie, et al., "Functional Comparison of Two Human Monocyte Chemotactin Protein-2 Isoforms, Role of the Amino-Terminal Pyroglutamic Acid and Processing by CD26/Dipeptidyl Peptidase IV", Biochemistry, vol. 37, No. 36, Jan. 1, 1998, 12672-12680.
De Boer, et al., "Cytokines and Therapy in COPD: A Promising Combination?", Chest, vol. 121, No. 90050, May 1, 2002, 209S-218.
Eksteen, et al., "Hepatic Endothelial CCL25 Mediates the Recruitment of CCR9+ Gut-Homing Lymphocytes to the Sclerosing Cholangitis", Journal of Experimental Medicine, vol. 200, No. 11, Dec. 6, 2004, 1511-1517.
European Office Action for European Patent Application No. 1272680.6, dated Mar. 16, 2015, 6 pages.
European Office Action for European Patent Application No. 12727915.6, dated Oct. 13, 2015, 3 pages.
European Search Report for European Patent Application No. 12727921, dated May 24, 2016, 4.
Feng, "Involvement of a Novel Chemokine Decoy Receptor CCX-CKRin Breast Cancer Growth Metastasis and Patient Survival", Clinical Cancer Research, vol. 15, No. 9, May 1, 2009, 2962-2970.
Grant, et al., "Hepatic Expression of Secondary Lymphoid Chemokine (CCL21) Promotes the Development of Portal-Associated Lymphoid Tissue in Chronic Inflammatory Liver Disease", American Journal of Pathology, vol. 160, No. 4, Apr. 2002, 1445-1455.
Hanai, et al., "The Mode of Actions of Adacolumn Therapeutic Leucocytapheresis in Patients with Inflammatory Bowel Disease: A Concise Review", Clinical & Experimental Immunology, vol. 163, No. 1, Nov. 16, 2010, 50-58.
Hsing-Cheng, et al., "Immunologic Variables in Acute Mania of Bipolar Disorder", Journal of Neuroimmunology, vol. 150, No. 1-2, May 1, 2004, 116-122.
Hu, "Schizophrenia is a TH2 Dominant Autoimmune Disease Possibly Against Acetylcholine Receptors of CNS", ViXra.org, vol. 1204, Apr. 30, 2012, 0070.
Iarlori, et al., "Interferon beta-1b Modulates MCP-1 Expression and Production in Relapsing-Remitting Multiple Sclerosis", Journal of Neuroimmunology, vol. 123, No. 1-2, Feb. 1, 2002, 170-179.
International Search Report and Written Opinion for PCT/GB2012/051345, dated Jan. 11, 2013, 24 pages.
International Search Report and Written Opinion for PCT/GB2012/051346, dated Jan. 11, 2013, 22 pages.
International Search Report and Written Opinion for PCT/GB2012/051348, dated Jan. 11, 2013, 23 pages.
International Search Report and Written Opinion for PCT/GB2012/051353, dated Jan. 11, 2013, 22 pages.
International Search Report and Written Opinion for PCT/GB2012/051355, dated Jan. 11, 2013, 22 pages.
International Search Report for PCT/GB2012/051349, dated Jan. 2, 2013, 7 pages.
International Search Report for PCT/GB2012/051350, dated Jan. 11, 2013, 6 pages.
International Search Report for PCT/GB2012/051351, dated Jan. 2, 2013, 5 pages.
International Search Report for PCT/GB2012/051352, dated Jan. 11, 2013, 7 pages.
International Search Report for PCT/GB2012/051354, dated Jan. 11, 2013, 7 pages.
International Search Report for PCT/GB2012/051356, dated Jan. 11, 2013, 6 pages.
International Search Report for PCT/GB2012/051357, dated Nov. 19, 2012, 6 pages.

(56) References Cited

OTHER PUBLICATIONS

Iwamoto, et al., "Molecular Aspects of Rheumatoid Arthritis: Chemokines in the Joints of Patients", FEBS Journal, vol. 275. No. 18, Sep. 1, 2008, 4448-4455.
Kruszynski, et al., "Synthetic, Site-Specific Biotinylated Analogs of Human MCP-1", Journal of Peptide Science, vol. 12, May 1, 2006, 354-360.
Linton, et al., "CCR9-Expressing CD14+HLA-DRhi Blood Monocytes Promote Intestinal Inflammation in IBD", Journal of Translational Medicine, vol. 9, No. Supply 2, Nov. 23, 2011, p. 32.
Liu, et al., "Correlation Effect of EGFR and CXCR4 and CCR7 Chemokine Receptors in Predicting Breast Cancer Vletastasis and Prognosis", Journal of Experimental & Clinical Cancer Research, vol. 29, No. 16, 2010, 9 pages.
Lumeng et al. "Obesity Induces a Phenotypic Switch in Adipose Tissue Macrophage Polarization", Journal of Clinical Investigation, American Society for Clinical Investigation, vol. 117, No. 1, Jan. 1, 2007, 175-184.
Maury, et al., "Adipokine Dysregulation, Adipose Tissue Inflammation and Metabolic Syndrome", Molecular and Cellular Endocrinology, vol. 314, No. 1, Jan. 15, 2010, 1-16.
Nakajima, "Increased Intrathecal Chemokine Receptor CCR2 Expression in Multiple Sclerosis", Biomarker Insights, Jan. 1, 2007, 463.
Nakatani, et al., "CCR4+ Memory CD4+ T Lymphocytes are Increased in Peripheral Blood and Lesional Skin from Patients with Atopic Dermatitis", Journal of Allergy and Clinical Immunology, vol. 107, No. 2, Feb. 1, 2001, 353-358.
Niu, et al., "Role of MCP-1 in Cardiovascular Disease: Molecular Mechanisms and Clinical Implications", Clinical Science, vol. 117, No. 3, Aug. 2009, 95-109.
Pease, et al., "Asthma, Allergy and Chemokines", Current Drug Targets, vol. 7, No. 1, retrieved from the Internet on Sep. 13, 2012: http://www.benthamdirect.org/pages/article/1/117/asthma-allergy-and-chemo-kines.html, Jan. 1, 2006, 3-12.
Petrek, et al., "CC and C Chemokine Expression in Pulmonary Sarcoidosis", European Respiratory Journal, vol. 20, No. 5, Nov. 1, 2002, 1206-1212.
Reale, et al., "Dysregulation of Chemo-Cytokine Production in Schizophrenic Patients Versus Healthy Controls", BMC Neuroscience, Biomed Central, vol. 12, No. 1, Jan. 25, 2011, 13 pages.
Reape, et al., "Chemokines and Atherosclerosis", Atherosclerosis, vol. 147, No. 2, Dec. 1, 1999, 213-225.
Rottman, et al., "Potential Role of the Chemokine Receptors CXCR3, CCR4, and the Integrin AlphaEbeta7 in the Pathogenesis of Psoriasis Vulgaris", Laboratory Investigation, vol. 81, No. 3, Mar. 2001, 335-347.
Sarafi, et al., "Murine Monocyte Chemoattractant Protein (MCP)-5: A Novel CC Chemokine that is a Structural and Functional Homologue of Human MCP-1", Journal of Experimental Medicine, vol. 185, No. 1, Jan. 1, 1997, 99-110.
Souto, et al., "Essential Role of CCR2 in Neutrophil Tissue Infiltration and Multiple Organ Dysfunction in Sepsis", American Journal of Respiratory and Critical Care Medicine, vol. 183, No. 2, Jan. 15, 2011, 234-242.
Speyer, "Novel Chemokine Responsiveness and Mobilization of Neutrophils During Sepsis", American Journal of Pathology, vol. 165, No. 6, Dec. 2004, 2187-2196.
Takanami, "Overexpression of CCR7 mRNA in Nonsmall Cell Lung Cancer: Correlation with Lymph Node Metastasis", International Journal of Cancer, vol. 105, No. 2, Jun. 10, 2003, 186-189.
Teixeira, et al., "Increased Serum Levels of CCL11/eotaxin in Schizophrenia", Progress in Neuro-Psychopharmacology & Biological Psychiatry, vol. 32, No. 3, Nov. 23, 2007, 710-714.
Terada, et al., "Stromal Cell-Derived Factor-1 from Biliary Epithelial Cells Recruits CXCR4-Positive Cells: Implications for Inflammatory Liver Disease", Laboratory Investigation, vol. 83, No. 5, May 1, 2003, 665-672.
Teraki, et al., "Homing Receptor and Chemokine Receptor on Intraedidermal T Cells in Psoriasis Vulgaris", Clinical and Experimental Dermatology, vol. 29, No. 6, Nov. 1, 2004, 658-663.
Tylaska, "CCR2 Regulates the Level of MCP-1/CCL2 in Vitro and at Inflammatory Sites and Controls T Cell Activation in Response to Alloantigen", Cytokine, vol. 18, No. 4, May 1, 2002, 184-190.
Vergunst, et al., "Modulation of CCR2 in Rheumatoid Arthritis—A Double-Blind, Randomized, Placebo-Controlled Clinical Trial", Arthritis & Rheumatism, vol. 58, No. 7, Jul. 1, 2008, 1931-1939.
Vita, et al., "Synthesis and Characterization of Biologically Functional Biotinylated Rantes", Journal of Immunological Methods, Aug. 1, 2002, 53-65.
Walters, et al., "Characterization of CCX282-B, and Orally Bioavailable Antagonist of the CCR9 Chemokine Receptor, for Treatment of Inflammatory Bowel Disease", Journal of Pharmacology and Experimental Therapeutics, vol. 335, No. 1, Oct. 1, 2010, 61-69.
Williams, et al., "Eotaxin and CCR3 as Therapeutic Targets in Asthma and Allergy", Chemokines 2, retrieved from the Internet on Sep. 17, 2012: http://www.pasteur.fr/applications/euroconf/chemokines2/Williams.pdf Jan. 1, 2003, 4.
Yawalkar, et al., "Enhanced Expression of Eotaxin and CCR3 in Atopic Dermatitis", Journal of Investigative Dermatology, vol. 113, No. 1, Jul. 1, 1999, 43-48.
Palchevskiy et al., "Immune response CC chemokinesCCL2 and CCL5 are associated with pulmonary sarcoidosis," Fibrogenesis & Tissue Repair, 2011, 4:10, 12 pages.
Kerstjens et al., "Tolerability and efficacy of inhaled AZD4818, a CCR1 antagonist, in moderate to severe COPD patients," Respiratory Medicine, 2010, 104, pp. 1297-1303.
Sonnleitner, "Adipositas: Inflammation im viszeralen Fettgewebe" Dissertation, University Hospital Ulm Center for Internal Medicine Department of Internal Medicine II, 2010.
Stulnig, "Adipositas und die Entziindung des Fettgewebes," Journal für Klinische Endokrinologie und Stoffwechsel—Austrian, 2009, 2(3):17-21.
European Patent Office Action for Application No. 12727914.9 dated Feb. 19, 2018 (7 pages).
Hasegawa et al., "Increased chemokine receptor CCR7/EB11 expression enhances the infiltration of lymphoid organs by adult T-cell leukemia cells," Blood, 2000, 95(1):30-38.
Lazennec et al., "Chemokines and chemokine receptors: new insights into cancer-related inflammation," Trends in Molecular Medicine, 2010, 16(3):133-144.
Yan et al., "Expression of vascular endothelial growth factor C and chemokine receptor CCR7 in gastric carcinoma and their values in predicting lymph node metastasis," World J Gastroenterol, 2004, 10(6):783-790.
European Patent Office Action for Application No. 12727916.4 dated Apr. 19, 2018 (7 pages).
Cummings et al., "Expression and Function of the Chemokine Receptors CXCR1 and CXCR2 in Sepsis," J. Immunology, 1999, 162: 2341-2346.
Kanamori et al., "Inhibition of MCP-1/CCR2 pathway ameliorates the development of diabetic nephropathy," Biochemical and Biophysical Research Communications, 2007, 360: 772-777.
Kaneider et al., "Reversing Systemic inflammatory Response syndrome with chemokine receptor pepducins," Nature Medicine, 2005, 11: 661-665.
Mahad et al., "The role of MCP-1 (CCL2) and CCR2 in multiple sclerosis and experimental autoimmune encephalomyelitis (EAE)," Seminars in Immunology, 2003, 15: 23-32.
NCI Dictionary of Cancer Terms, downloaded Sep. 27, 2018.
Owen, "Chemokine Receptors in Airway Disease: Which Receptors to Target?," Pulmonary Pharm and Therap, 2001, 14: 193-202.
Stuart et al., "Chemokines and chemokine receptors in mood disorders, schizophrenia, and cognitive impairment: A systematic review of biomarker studies," Neuroscience and Behavioral Review, 2014, 42:93-115.
Stuart et al., "Systematic review of the neurobiological relevance of chemokines to psychiatric disorders," Frontiers in cellular Neuroscience, 2015, 9:1-15.
Tamura et al., "C-C chemokine receptor 2 inhibitor improves diet-induced development of insulin resistance and hepatic steatosis in mice," J Atheroscler Thromb., 2010, 17: 219-228.

(56) References Cited

OTHER PUBLICATIONS

Tamura et al., "Inhibition of CCR2 Ameliorates Insulin Resistance and Hepatic Steatosis in db/db Mice," Arterioscler Thromb Vasc Biol., 2008, 28: 2195-2201.
Zaballos et al., "Cutting Edge: Identification of the Orphan Chemokine Receptor GPR-9-6 as CCR9, the Receptor for the Chemokine TECK," J. Immunol., 1999, 162:5671-5675.
United States Patent Office Action for U.S. Appl. No. 15/629,691 dated Dec. 17, 2018 (9 pages).
United States Patent Office Action for U.S. Appl. No. 15/629,697 dated Sep. 28, 2018 (9 pages).
United States Patent Office Action for U.S. Appl. No. 15/629,700 dated Oct. 2, 2018 (11 pages).
United States Patent Office Action for U.S. Appl. No. 15/629,705 dated Dec. 3, 2018 (10 pages).
United States Patent Office Action for U.S. Appl. No. 15/629,713 dated Oct. 26, 2018 (12 pages).
Mine et al., "Increased expression levels of monocyte CCR2 and monocyte chemoattractant protein-1 in patients with diabetes mellitus," Biochemical and Biophysical Communications, 2006, 344: 780-785.
Izikson et al., "Resistance to Experimental Autoimmune Encephalomyelitis in Mice Lacking the CC Chemokine Receptor (CCR)2," J. Exp. Med., 2000, 192:1075-1080.
Xia et al., "Recent developments in CCR2 antagonist," Expert Opinion on Therap. Patents, 2009, 19:295-303.
United States Patent Office Action for U.S. Appl. No. 15/629,697 dated Apr. 2, 2019 (10 pages).
United States Patent Office Notice of Allowance for U.S. Appl. No. 15/629,700 dated May 9, 2019 (9 pages).
United States Patent Office Notice of Allowance for U.S. Appl. No. 15/629,713 dated Apr. 29, 2019 (8 pages).
United States Patent Office Notice of Allowance for U.S. Appl. No. 15/629,705 dated May 24, 2019 (8 pages).
United States Patent Office Notice of Allowance for U.S. Appl. No. 15/629,691 dated Jun. 14, 2019 (9 pages).

\* cited by examiner

SEQUENCE LISTING

```
<160> NUMBER OF SEQ ID NOS: 34

<210> SEQ ID NO 1
<211> LENGTH: 76
<212> TYPE: PRT
<213> ORGANISM: Artificial sequence
<220> FEATURE:
<223> OTHER INFORMATION: Synthetic peptide
<220> FEATURE:
<221> NAME/KEY: X
<222> LOCATION: (1)..(1)
<223> OTHER INFORMATION: X is pyroglutamine or Gln
<220> FEATURE:
<221> NAME/KEY: X
<222> LOCATION: (75)..(75)
<223> OTHER INFORMATION: X is an amino acid residue that can be
      biotinylated, such as lysine, ornithine or diaminopropionic acid
      and optionally is biotinylated, optionally via a spacer molecule
      such as PEG, in particular K(PEG-Biotin)

<400> SEQUENCE: 1

Xaa Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Lys Arg Gly
        35                  40                  45

Lys Glu Val Cys Ala Asp Pro Lys Glu Arg Trp Val Arg Asp Ser Met
    50                  55                  60

Lys His Leu Asp Gln Ile Phe Gln Asn Leu Xaa Pro
```

```
                       65                  70                  75

<210> SEQ ID NO 2
<211> LENGTH: 76
<212> TYPE: PRT
<213> ORGANISM: Artificial sequence
<220> FEATURE:
<223> OTHER INFORMATION: Synthetic peptide
<220> FEATURE:
<221> NAME/KEY: X
<222> LOCATION: (1)..(1)
<223> OTHER INFORMATION: X is pyroglutamine or Gln
<220> FEATURE:
<221> NAME/KEY: X
<222> LOCATION: (75)..(75)
<223> OTHER INFORMATION: X is FmocLys(ivDde)

<400> SEQUENCE: 2

Xaa Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Lys Arg Gly
        35                  40                  45

Lys Glu Val Cys Ala Asp Pro Lys Glu Arg Trp Val Arg Asp Ser Met
    50                  55                  60

Lys His Leu Asp Gln Ile Phe Gln Asn Leu Xaa Pro
65                  70                  75

<210> SEQ ID NO 3
<211> LENGTH: 76
<212> TYPE: PRT
<213> ORGANISM: Artificial sequence
<220> FEATURE:
<223> OTHER INFORMATION: Synthetic peptide
<220> FEATURE:
<221> NAME/KEY: X
<222> LOCATION: (1)..(1)
<223> OTHER INFORMATION: X is pyroglutamine
<220> FEATURE:
<221> NAME/KEY: X
<222> LOCATION: (1)..(1)
<223> OTHER INFORMATION: X is pyroglutamine or Gln
<220> FEATURE:
<221> NAME/KEY: X
<222> LOCATION: (75)..(75)
<223> OTHER INFORMATION: X is K(PEG-Biotin)

<400> SEQUENCE: 3

Xaa Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Lys Arg Gly
        35                  40                  45

Lys Glu Val Cys Ala Asp Pro Lys Glu Arg Trp Val Arg Asp Ser Met
    50                  55                  60

Lys His Leu Asp Gln Ile Phe Gln Asn Leu Xaa Pro
65                  70                  75

<210> SEQ ID NO 4
<211> LENGTH: 68
<212> TYPE: PRT
<213> ORGANISM: Artificial sequence
<220> FEATURE:
<223> OTHER INFORMATION: Synthetic peptide
```

<400> SEQUENCE: 4

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
    50                  55                  60

Leu Glu Lys Ser
65

<210> SEQ ID NO 5
<211> LENGTH: 68
<212> TYPE: PRT
<213> ORGANISM: Artificial sequence
<220> FEATURE:
<223> OTHER INFORMATION: Synthetic peptide
<220> FEATURE:
<221> NAME/KEY: X
<222> LOCATION: (67)..(67)
<223> OTHER INFORMATION: X is FmocLys(ivDde)

<400> SEQUENCE: 5

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
    50                  55                  60

Leu Glu Xaa Ser
65

<210> SEQ ID NO 6
<211> LENGTH: 68
<212> TYPE: PRT
<213> ORGANISM: Artificial sequence
<220> FEATURE:
<223> OTHER INFORMATION: Synthetic peptide
<220> FEATURE:
<221> NAME/KEY: X
<222> LOCATION: (67)..(67)
<223> OTHER INFORMATION: X is an amino acid residue that can be
      biotinylated, such as lysine, ornithine or diaminopropionic acid
      and optionally is biotinylated (e.g. K-biotin), optionally via a
      spacer molecule such as PEG, in particular K(PEG-Biotin)

<400> SEQUENCE: 6

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
    50                  55                  60

Leu Glu Xaa Ser
65

<210> SEQ ID NO 7
<211> LENGTH: 70
<212> TYPE: PRT
<213> ORGANISM: Artificial sequence
<220> FEATURE:
<223> OTHER INFORMATION: Synthetic peptide

<400> SEQUENCE: 7

Ala Ser Asn Phe Asp Cys Cys Leu Gly Tyr Thr Asp Arg Ile Leu His
1               5                   10                  15

Pro Lys Phe Ile Val Gly Phe Thr Arg Gln Leu Ala Asn Glu Gly Cys
            20                  25                  30

Asp Ile Asn Ala Ile Ile Phe His Thr Lys Lys Leu Ser Val Cys
        35                  40                  45

Ala Asn Pro Lys Gln Thr Trp Val Lys Tyr Ile Val Arg Leu Leu Ser
    50                  55                  60

Lys Lys Val Lys Asn Met
65                  70

<210> SEQ ID NO 8
<211> LENGTH: 70
<212> TYPE: PRT
<213> ORGANISM: Artificial sequence
<220> FEATURE:
<223> OTHER INFORMATION: Synthetic peptide
<220> FEATURE:
<221> NAME/KEY: X
<222> LOCATION: (68)..(68)
<223> OTHER INFORMATION: X is FmocLys(ivDde)

<400> SEQUENCE: 8

Ala Ser Asn Phe Asp Cys Cys Leu Gly Tyr Thr Asp Arg Ile Leu His
1               5                   10                  15

Pro Lys Phe Ile Val Gly Phe Thr Arg Gln Leu Ala Asn Glu Gly Cys
            20                  25                  30

Asp Ile Asn Ala Ile Ile Phe His Thr Lys Lys Leu Ser Val Cys
        35                  40                  45

Ala Asn Pro Lys Gln Thr Trp Val Lys Tyr Ile Val Arg Leu Leu Ser
    50                  55                  60

Lys Lys Val Xaa Asn Met
65                  70

<210> SEQ ID NO 9
<211> LENGTH: 70
<212> TYPE: PRT
<213> ORGANISM: Artificial sequence
<220> FEATURE:
<223> OTHER INFORMATION: Synthetic peptide
<220> FEATURE:
<221> NAME/KEY: X
<222> LOCATION: (68)..(68)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 9

Ala Ser Asn Phe Asp Cys Cys Leu Gly Tyr Thr Asp Arg Ile Leu His
1               5                   10                  15

Pro Lys Phe Ile Val Gly Phe Thr Arg Gln Leu Ala Asn Glu Gly Cys
            20                  25                  30

Asp Ile Asn Ala Ile Ile Phe His Thr Lys Lys Leu Ser Val Cys
        35                  40                  45

```
Ala Asn Pro Lys Gln Thr Trp Val Lys Tyr Ile Val Arg Leu Leu Ser
 50                  55                  60

Lys Lys Val Xaa Asn Met
 65                  70
```

<210> SEQ ID NO 10
<211> LENGTH: 67
<212> TYPE: PRT
<213> ORGANISM: Artificial sequence
<220> FEATURE:
<223> OTHER INFORMATION: Synthesised peptide

<400> SEQUENCE: 10

```
Lys Pro Val Ser Leu Ser Tyr Arg Cys Pro Cys Arg Phe Phe Glu Ser
  1               5                  10                  15

His Val Ala Arg Ala Asn Val Lys His Leu Lys Ile Leu Asn Thr Pro
             20                  25                  30

Asn Cys Ala Leu Gln Ile Val Ala Arg Leu Lys Asn Asn Asn Arg Gln
         35                  40                  45

Val Cys Ile Asp Pro Lys Leu Lys Trp Ile Gln Glu Tyr Leu Glu Lys
 50                  55                  60

Ala Leu Asn
 65
```

<210> SEQ ID NO 11
<211> LENGTH: 66
<212> TYPE: PRT
<213> ORGANISM: Artificial sequence
<220> FEATURE:
<223> OTHER INFORMATION: Synthetic peptide
<220> FEATURE:
<221> NAME/KEY: X
<222> LOCATION: (64)..(64)
<223> OTHER INFORMATION: X is FmocLys(ivDde)

<400> SEQUENCE: 11

```
Lys Pro Val Ser Leu Ser Tyr Arg Cys Pro Cys Arg Phe Phe Glu Ser
  1               5                  10                  15

His Val Ala Arg Ala Asn Val Lys His Leu Lys Ile Leu Asn Thr Pro
             20                  25                  30

Asn Cys Ala Leu Gln Ile Val Ala Arg Leu Lys Asn Asn Asn Arg Gln
         35                  40                  45

Val Cys Ile Asp Pro Lys Leu Lys Trp Ile Gln Glu Tyr Leu Glu Ala
 50                  55                  60

Leu Asn
 65
```

<210> SEQ ID NO 12
<211> LENGTH: 67
<212> TYPE: PRT
<213> ORGANISM: Artificial sequence
<220> FEATURE:
<223> OTHER INFORMATION: Synthetic peptide
<220> FEATURE:
<221> NAME/KEY: X
<222> LOCATION: (64)..(64)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 12

```
Lys Pro Val Ser Leu Ser Tyr Arg Cys Pro Cys Arg Phe Phe Glu Ser
```

```
  1               5                  10                 15
His Val Ala Arg Ala Asn Val Lys His Leu Lys Ile Leu Asn Thr Pro
             20                  25                 30

Asn Cys Ala Leu Gln Ile Val Ala Arg Leu Lys Asn Asn Asn Arg Gln
             35                  40                 45

Val Cys Ile Asp Pro Lys Leu Lys Trp Ile Gln Glu Tyr Leu Glu Xaa
 50                  55                 60

Ala Leu Asn
 65
```

<210> SEQ ID NO 13
<211> LENGTH: 69
<212> TYPE: PRT
<213> ORGANISM: Artificial sequence
<220> FEATURE:
<223> OTHER INFORMATION: Synthetic peptide

<400> SEQUENCE: 13

```
Gly Pro Tyr Gly Ala Asn Met Glu Asp Ser Val Cys Cys Arg Asp Tyr
 1               5                  10                 15

Val Arg Tyr Arg Leu Pro Leu Arg Val Val Lys His Phe Tyr Trp Thr
             20                  25                 30

Ser Asp Ser Cys Pro Arg Pro Gly Val Val Leu Leu Thr Phe Arg Asp
             35                  40                 45

Lys Glu Ile Cys Ala Asp Pro Arg Val Pro Trp Val Lys Met Ile Leu
 50                  55                 60

Asn Lys Leu Ser Gln
 65
```

<210> SEQ ID NO 14
<211> LENGTH: 69
<212> TYPE: PRT
<213> ORGANISM: Artificial sequence
<220> FEATURE:
<223> OTHER INFORMATION: Synthetic peptide
<220> FEATURE:
<221> NAME/KEY: X
<222> LOCATION: (66)..(66)
<223> OTHER INFORMATION: X is FmocLys(ivDde)

<400> SEQUENCE: 14

```
Gly Pro Tyr Gly Ala Asn Met Glu Asp Ser Val Cys Cys Arg Asp Tyr
 1               5                  10                 15

Val Arg Tyr Arg Leu Pro Leu Arg Val Val Lys His Phe Tyr Trp Thr
             20                  25                 30

Ser Asp Ser Cys Pro Arg Pro Gly Val Val Leu Leu Thr Phe Arg Asp
             35                  40                 45

Lys Glu Ile Cys Ala Asp Pro Arg Val Pro Trp Val Lys Met Ile Leu
 50                  55                 60

Asn Xaa Leu Ser Gln
 65
```

<210> SEQ ID NO 15
<211> LENGTH: 69
<212> TYPE: PRT
<213> ORGANISM: Artificial sequence
<220> FEATURE:
<223> OTHER INFORMATION: Synthetic peptide
<220> FEATURE:
<221> NAME/KEY: X
<222> LOCATION: (66)..(66)
<223> OTHER INFORMATION: X is an amino acid residue that can be -continued biotinylated, such as lysine, ornithine or diaminopropionic acid
and optionally is biotinylated, optionally via a spacer molecule
such as PEG, especially K(PEG-Biotin)

<400> SEQUENCE: 15

Gly Pro Tyr Gly Ala Asn Met Glu Asp Ser Val Cys Cys Arg Asp Tyr
1               5                   10                  15

Val Arg Tyr Arg Leu Pro Leu Arg Val Val Lys His Phe Tyr Trp Thr
                20                  25                  30

Ser Asp Ser Cys Pro Arg Pro Gly Val Val Leu Leu Thr Phe Arg Asp
            35                  40                  45

Lys Glu Ile Cys Ala Asp Pro Arg Val Pro Trp Val Lys Met Ile Leu
    50                  55                  60

Asn Xaa Leu Ser Gln
65

<210> SEQ ID NO 16
<211> LENGTH: 72
<212> TYPE: PRT
<213> ORGANISM: Artificial sequence
<220> FEATURE:
<223> OTHER INFORMATION: Synthetic peptide
<220> FEATURE:
<221> NAME/KEY: X
<222> LOCATION: (72)..(72)
<223> OTHER INFORMATION: X is an amino acid residue that can be
      biotinylated, such as lysine, ornithine or diaminopropionic acid
      and optionally is biotinylated (e.g. K-biotin), optionally via a
      spacer molecule such as PEG, in particular K(PEG-Biotin)

<400> SEQUENCE: 16

Ala Arg Gly Thr Asn Val Gly Arg Glu Cys Cys Leu Glu Tyr Phe Lys
1               5                   10                  15

Gly Ala Ile Pro Leu Arg Lys Leu Lys Thr Trp Tyr Gln Thr Ser Glu
                20                  25                  30

Asp Cys Ser Arg Asp Ala Ile Val Phe Val Thr Val Gln Gly Arg Ala
            35                  40                  45

Ile Cys Ser Asp Pro Asn Asn Lys Arg Val Lys Asn Ala Val Lys Tyr
    50                  55                  60

Leu Gln Ser Leu Glu Arg Ser Xaa
65                  70

<210> SEQ ID NO 17
<211> LENGTH: 72
<212> TYPE: PRT
<213> ORGANISM: Artificial sequence
<220> FEATURE:
<223> OTHER INFORMATION: Synthetic peptide
<220> FEATURE:
<221> NAME/KEY: X
<222> LOCATION: (72)..(72)
<223> OTHER INFORMATION: X is FmocLys(ivDde)

<400> SEQUENCE: 17

Ala Arg Gly Thr Asn Val Gly Arg Glu Cys Cys Leu Glu Tyr Phe Lys
1               5                   10                  15

Gly Ala Ile Pro Leu Arg Lys Leu Lys Thr Trp Tyr Gln Thr Ser Glu
                20                  25                  30

Asp Cys Ser Arg Asp Ala Ile Val Phe Val Thr Val Gln Gly Arg Ala
            35                  40                  45

Ile Cys Ser Asp Pro Asn Asn Lys Arg Val Lys Asn Ala Val Lys Tyr
    50                  55                  60

```
Leu Gln Ser Leu Glu Arg Ser Xaa
 65                  70
```

<210> SEQ ID NO 18
<211> LENGTH: 72
<212> TYPE: PRT
<213> ORGANISM: Artificial sequence
<220> FEATURE:
<223> OTHER INFORMATION: Synthetic peptide
<220> FEATURE:
<221> NAME/KEY: X
<222> LOCATION: (72)..(72)
<223> OTHER INFORMATION: X is K(PEG-Biotin)

<400> SEQUENCE: 18

```
Ala Arg Gly Thr Asn Val Gly Arg Glu Cys Cys Leu Glu Tyr Phe Lys
 1               5                  10                  15

Gly Ala Ile Pro Leu Arg Lys Leu Lys Thr Trp Tyr Gln Thr Ser Glu
             20                  25                  30

Asp Cys Ser Arg Asp Ala Ile Val Phe Val Thr Val Gln Gly Arg Ala
         35                  40                  45

Ile Cys Ser Asp Pro Asn Asn Lys Arg Val Lys Asn Ala Val Lys Tyr
     50                  55                  60

Leu Gln Ser Leu Glu Arg Ser Xaa
 65                  70
```

<210> SEQ ID NO 19
<211> LENGTH: 78
<212> TYPE: PRT
<213> ORGANISM: Artificial sequence
<220> FEATURE:
<223> OTHER INFORMATION: Synthetic peptide
<220> FEATURE:
<221> NAME/KEY: X
<222> LOCATION: (78)..(78)
<223> OTHER INFORMATION: X is an amino acid residue that can be
      biotinylated, such as lysine, ornithine or diaminopropionic acid
      and optionally is biotinylated (e.g. K-biotin), optionally via a
      spacer molecule such as PEG, in particular K(PEG-Biotin)

<400> SEQUENCE: 19

```
Gly Thr Asn Asp Ala Glu Asp Cys Cys Leu Ser Val Thr Gln Lys Pro
 1               5                  10                  15

Ile Pro Gly Tyr Ile Val Arg Asn Phe His Tyr Leu Leu Ile Lys Asp
             20                  25                  30

Gly Cys Arg Val Pro Ala Val Val Phe Thr Thr Leu Arg Gly Arg Gln
         35                  40                  45

Leu Cys Ala Pro Pro Asp Gln Pro Trp Val Glu Arg Ile Ile Gln Arg
     50                  55                  60

Leu Gln Arg Thr Ser Ala Lys Met Lys Arg Arg Ser Ser Xaa
 65                  70                  75
```

<210> SEQ ID NO 20
<211> LENGTH: 78
<212> TYPE: PRT
<213> ORGANISM: Artificial sequence
<220> FEATURE:
<223> OTHER INFORMATION: Synthetic peptide
<220> FEATURE:
<221> NAME/KEY: X
<222> LOCATION: (78)..(78)
<223> OTHER INFORMATION: X is FmocLys(ivDde)

<400> SEQUENCE: 20

```
Gly Thr Asn Asp Ala Glu Asp Cys Cys Leu Ser Val Thr Gln Lys Pro
```

```
                1               5                   10                  15

Ile Pro Gly Tyr Ile Val Arg Asn Phe His Tyr Leu Leu Ile Lys Asp
            20                  25                  30

Gly Cys Arg Val Pro Ala Val Val Phe Thr Thr Leu Arg Gly Arg Gln
        35                  40                  45

Leu Cys Ala Pro Pro Asp Gln Pro Trp Val Glu Arg Ile Ile Gln Arg
    50                  55                  60

Leu Gln Arg Thr Ser Ala Lys Met Lys Arg Arg Ser Ser Xaa
65                  70                  75

<210> SEQ ID NO 21
<211> LENGTH: 78
<212> TYPE: PRT
<213> ORGANISM: Artificial sequence
<220> FEATURE:
<223> OTHER INFORMATION: Synthetic peptide
<220> FEATURE:
<221> NAME/KEY: X
<222> LOCATION: (78)..(78)
<223> OTHER INFORMATION: X is biotinylated lysine

<400> SEQUENCE: 21

Gly Thr Asn Asp Ala Glu Asp Cys Cys Leu Ser Val Thr Gln Lys Pro
1               5                   10                  15

Ile Pro Gly Tyr Ile Val Arg Asn Phe His Tyr Leu Leu Ile Lys Asp
            20                  25                  30

Gly Cys Arg Val Pro Ala Val Val Phe Thr Thr Leu Arg Gly Arg Gln
        35                  40                  45

Leu Cys Ala Pro Pro Asp Gln Pro Trp Val Glu Arg Ile Ile Gln Arg
    50                  55                  60

Leu Gln Arg Thr Ser Ala Lys Met Lys Arg Arg Ser Ser Xaa
65                  70                  75

<210> SEQ ID NO 22
<211> LENGTH: 73
<212> TYPE: PRT
<213> ORGANISM: Artificial sequence
<220> FEATURE:
<223> OTHER INFORMATION: Synthetic peptide

<400> SEQUENCE: 22

Phe Pro Met Phe Lys Arg Gly Arg Cys Leu Cys Ile Gly Pro Gly Val
1               5                   10                  15

Lys Ala Val Lys Val Ala Asp Ile Glu Lys Ala Ser Ile Met Tyr Pro
            20                  25                  30

Ser Asn Asn Cys Asp Lys Ile Glu Val Ile Ile Thr Leu Lys Glu Asn
        35                  40                  45

Lys Gly Gln Arg Cys Leu Asn Pro Lys Ser Lys Gln Ala Arg Leu Ile
    50                  55                  60

Ile Lys Lys Val Glu Arg Lys Asn Phe
65                  70

<210> SEQ ID NO 23
<211> LENGTH: 74
<212> TYPE: PRT
<213> ORGANISM: Artificial sequence
<220> FEATURE:
<223> OTHER INFORMATION: Synthetic peptide
<220> FEATURE:
<221> NAME/KEY: X
<222> LOCATION: (74)..(74)
<223> OTHER INFORMATION: X =a residue that can be biotinylated, such as
``` lysine, ornithine or diaminopropionic acid and optionally is
biotinylated, optionally via a spacer molecule such as PEG. The
amino acid residue may be added via a spacer molecule such as PEG.

<400> SEQUENCE: 23

Phe Pro Met Phe Lys Arg Gly Arg Cys Leu Cys Ile Gly Pro Gly Val
1               5                   10                  15

Lys Ala Val Lys Val Ala Asp Ile Glu Lys Ala Ser Ile Met Tyr Pro
            20                  25                  30

Ser Asn Asn Cys Asp Lys Ile Glu Val Ile Ile Thr Leu Lys Glu Asn
        35                  40                  45

Lys Gly Gln Arg Cys Leu Asn Pro Lys Ser Lys Gln Ala Arg Leu Ile
    50                  55                  60

Ile Lys Lys Val Glu Arg Lys Asn Phe Xaa
65                  70

<210> SEQ ID NO 24
<211> LENGTH: 74
<212> TYPE: PRT
<213> ORGANISM: Artificial sequence
<220> FEATURE:
<223> OTHER INFORMATION: Synthetic peptide
<220> FEATURE:
<221> NAME/KEY: X
<222> LOCATION: (74)..(74)
<223> OTHER INFORMATION: X is PEG-K(ivDde)

<400> SEQUENCE: 24

Phe Pro Met Phe Lys Arg Gly Arg Cys Leu Cys Ile Gly Pro Gly Val
1               5                   10                  15

Lys Ala Val Lys Val Ala Asp Ile Glu Lys Ala Ser Ile Met Tyr Pro
            20                  25                  30

Ser Asn Asn Cys Asp Lys Ile Glu Val Ile Ile Thr Leu Lys Glu Asn
        35                  40                  45

Lys Gly Gln Arg Cys Leu Asn Pro Lys Ser Lys Gln Ala Arg Leu Ile
    50                  55                  60

Ile Lys Lys Val Glu Arg Lys Asn Phe Xaa
65                  70

<210> SEQ ID NO 25
<211> LENGTH: 74
<212> TYPE: PRT
<213> ORGANISM: Artificial sequence
<220> FEATURE:
<223> OTHER INFORMATION: Synthesised peptide
<220> FEATURE:
<221> NAME/KEY: X
<222> LOCATION: (74)..(74)
<223> OTHER INFORMATION: X is PEG-K(Biotin)

<400> SEQUENCE: 25

Phe Pro Met Phe Lys Arg Gly Arg Cys Leu Cys Ile Gly Pro Gly Val
1               5                   10                  15

Lys Ala Val Lys Val Ala Asp Ile Glu Lys Ala Ser Ile Met Tyr Pro
            20                  25                  30

Ser Asn Asn Cys Asp Lys Ile Glu Val Ile Ile Thr Leu Lys Glu Asn
        35                  40                  45

Lys Gly Gln Arg Cys Leu Asn Pro Lys Ser Lys Gln Ala Arg Leu Ile
    50                  55                  60

Ile Lys Lys Val Glu Arg Lys Asn Phe Xaa
65                  70

```
<210> SEQ ID NO 26
<211> LENGTH: 74
<212> TYPE: PRT
<213> ORGANISM: Artificial sequence
<220> FEATURE:
<223> OTHER INFORMATION: Synthesised peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (64)..(64)
<223> OTHER INFORMATION: X = Norleucine
<220> FEATURE:
<221> NAME/KEY: X
<222> LOCATION: (72)..(72)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 26

Xaa Gly Val Phe Glu Asp Cys Cys Leu Ala Tyr His Tyr Pro Ile Gly
1               5                   10                  15

Trp Ala Val Leu Arg Arg Ala Trp Thr Tyr Arg Ile Gln Glu Val Ser
            20                  25                  30

Gly Ser Cys Asn Leu Pro Ala Ala Ile Phe Tyr Leu Pro Lys Arg His
        35                  40                  45

Arg Lys Val Cys Gly Asn Pro Lys Ser Arg Glu Val Gln Arg Ala Xaa
    50                  55                  60

Lys Leu Leu Asp Ala Arg Asn Xaa Val Phe
65                  70

<210> SEQ ID NO 27
<211> LENGTH: 74
<212> TYPE: PRT
<213> ORGANISM: Artificial sequence
<220> FEATURE:
<223> OTHER INFORMATION: Synthesised peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (64)..(64)
<223> OTHER INFORMATION: X = Norleucine
<220> FEATURE:
<221> NAME/KEY: X
<222> LOCATION: (72)..(72)
<223> OTHER INFORMATION: X is K(ivDde)

<400> SEQUENCE: 27

Xaa Gly Val Phe Glu Asp Cys Cys Leu Ala Tyr His Tyr Pro Ile Gly
1               5                   10                  15

Trp Ala Val Leu Arg Arg Ala Trp Thr Tyr Arg Ile Gln Glu Val Ser
            20                  25                  30

Gly Ser Cys Asn Leu Pro Ala Ala Ile Phe Tyr Leu Pro Lys Arg His
        35                  40                  45

Arg Lys Val Cys Gly Asn Pro Lys Ser Arg Glu Val Gln Arg Ala Xaa
    50                  55                  60

Lys Leu Leu Asp Ala Arg Asn Xaa Val Phe
65                  70

<210> SEQ ID NO 28
```

-continued

```
<211> LENGTH: 74
<212> TYPE: PRT
<213> ORGANISM: Artificial sequence
<220> FEATURE:
<223> OTHER INFORMATION: Synthesised peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (64)..(64)
<223> OTHER INFORMATION: X = Norleucine
<220> FEATURE:
<221> NAME/KEY: X
<222> LOCATION: (72)..(72)
<223> OTHER INFORMATION: X is K(PEG-Biotin)

<400> SEQUENCE: 28

Xaa Gly Val Phe Glu Asp Cys Cys Leu Ala Tyr His Tyr Pro Ile Gly
1               5                   10                  15

Trp Ala Val Leu Arg Arg Ala Trp Thr Tyr Arg Ile Gln Glu Val Ser
            20                  25                  30

Gly Ser Cys Asn Leu Pro Ala Ala Ile Phe Tyr Leu Pro Lys Arg His
        35                  40                  45

Arg Lys Val Cys Gly Asn Pro Lys Ser Arg Glu Val Gln Arg Ala Xaa
    50                  55                  60

Lys Leu Leu Asp Ala Arg Asn Xaa Val Phe
65                  70

<210> SEQ ID NO 29
<211> LENGTH: 88
<212> TYPE: PRT
<213> ORGANISM: Artificial sequence
<220> FEATURE:
<223> OTHER INFORMATION: Synthesised peptide
<220> FEATURE:
<221> NAME/KEY: X
<222> LOCATION: (87)..(87)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 29

Phe Leu Leu Pro Pro Ser Thr Ala Cys Cys Thr Gln Leu Tyr Arg Lys
1               5                   10                  15

Pro Leu Ser Asp Lys Leu Leu Arg Lys Val Ile Gln Val Glu Leu Gln
            20                  25                  30

Glu Ala Asp Gly Asp Cys His Leu Gln Ala Phe Val Leu His Leu Ala
        35                  40                  45

Gln Arg Ser Ile Cys Ile His Pro Gln Asn Pro Ser Leu Ser Gln Trp
    50                  55                  60

Phe Glu His Gln Glu Arg Lys Leu His Gly Thr Leu Pro Lys Leu Asn
65                  70                  75                  80

Phe Gly Met Leu Arg Lys Xaa Gly
                85

<210> SEQ ID NO 30
<211> LENGTH: 88
<212> TYPE: PRT
<213> ORGANISM: Artificial sequence
<220> FEATURE:
<223> OTHER INFORMATION: Synthesised peptide
<220> FEATURE:
<221> NAME/KEY: X
```

```
<222> LOCATION: (87)..(87)
<223> OTHER INFORMATION: X is K(ivDde)

<400> SEQUENCE: 30

Phe Leu Leu Pro Pro Ser Thr Ala Cys Cys Thr Gln Leu Tyr Arg Lys
1               5                   10                  15

Pro Leu Ser Asp Lys Leu Leu Arg Lys Val Ile Gln Val Glu Leu Gln
            20                  25                  30

Glu Ala Asp Gly Asp Cys His Leu Gln Ala Phe Val Leu His Leu Ala
        35                  40                  45

Gln Arg Ser Ile Cys Ile His Pro Gln Asn Pro Ser Leu Ser Gln Trp
    50                  55                  60

Phe Glu His Gln Glu Arg Lys Leu His Gly Thr Leu Pro Lys Leu Asn
65                  70                  75                  80

Phe Gly Met Leu Arg Lys Xaa Gly
                    85

<210> SEQ ID NO 31
<211> LENGTH: 88
<212> TYPE: PRT
<213> ORGANISM: Artificial sequence
<220> FEATURE:
<223> OTHER INFORMATION: Synthesised peptide
<220> FEATURE:
<221> NAME/KEY: X
<222> LOCATION: (87)..(87)
<223> OTHER INFORMATION: X is K(PEG-Biotin)

<400> SEQUENCE: 31

Phe Leu Leu Pro Pro Ser Thr Ala Cys Cys Thr Gln Leu Tyr Arg Lys
1               5                   10                  15

Pro Leu Ser Asp Lys Leu Leu Arg Lys Val Ile Gln Val Glu Leu Gln
            20                  25                  30

Glu Ala Asp Gly Asp Cys His Leu Gln Ala Phe Val Leu His Leu Ala
        35                  40                  45

Gln Arg Ser Ile Cys Ile His Pro Gln Asn Pro Ser Leu Ser Gln Trp
    50                  55                  60

Phe Glu His Gln Glu Arg Lys Leu His Gly Thr Leu Pro Lys Leu Asn
65                  70                  75                  80

Phe Gly Met Leu Arg Lys Xaa Gly
                    85

<210> SEQ ID NO 32
<211> LENGTH: 77
<212> TYPE: PRT
<213> ORGANISM: Artificial sequence
<220> FEATURE:
<223> OTHER INFORMATION: Synthesised peptide

<400> SEQUENCE: 32

Val Pro Leu Ser Arg Thr Val Arg Cys Thr Cys Ile Ser Ile Ser Asn
1               5                   10                  15

Gln Pro Val Asn Pro Arg Ser Leu Glu Lys Leu Glu Ile Ile Pro Ala
            20                  25                  30

Ser Gln Phe Cys Pro Arg Val Glu Ile Ile Ala Thr Met Lys Lys Lys
        35                  40                  45

Gly Glu Lys Arg Cys Leu Asn Pro Glu Ser Lys Ala Ile Lys Asn Leu
    50                  55                  60

Leu Lys Ala Val Ser Lys Glu Arg Ser Lys Arg Ser Pro
65                  70                  75
```

```
<210> SEQ ID NO 33
<211> LENGTH: 78
<212> TYPE: PRT
<213> ORGANISM: Artificial sequence
<220> FEATURE:
<223> OTHER INFORMATION: Synthesised peptide
<220> FEATURE:
<221> NAME/KEY: X
<222> LOCATION: (78)..(78)
<223> OTHER INFORMATION: X is K(ivDde), optionally attached via a spacer
      such as PEG, e.g. -PEG-K(ivDde)

<400> SEQUENCE: 33

Val Pro Leu Ser Arg Thr Val Arg Cys Thr Cys Ile Ser Ile Ser Asn
1               5                   10                  15

Gln Pro Val Asn Pro Arg Ser Leu Glu Lys Leu Glu Ile Ile Pro Ala
            20                  25                  30

Ser Gln Phe Cys Pro Arg Val Glu Ile Ile Ala Thr Met Lys Lys Lys
        35                  40                  45

Gly Glu Lys Arg Cys Leu Asn Pro Glu Ser Lys Ala Ile Lys Asn Leu
    50                  55                  60

Leu Lys Ala Val Ser Lys Glu Arg Ser Lys Arg Ser Pro Xaa
65                  70                  75

<210> SEQ ID NO 34
<211> LENGTH: 78
<212> TYPE: PRT
<213> ORGANISM: Artificial sequence
<220> FEATURE:
<223> OTHER INFORMATION: Synthesised peptide
<220> FEATURE:
<221> NAME/KEY: X
<222> LOCATION: (78)..(78)
<223> OTHER INFORMATION: X =a residue that can be biotinylated, such as
      lysine, ornithine or diaminopropionic acid and optionally is
      biotinylated, optionally via a spacer molecule such as PEG. The
      amino acid residue may be added via a spacer molecule such as PEG.

<400> SEQUENCE: 34

Val Pro Leu Ser Arg Thr Val Arg Cys Thr Cys Ile Ser Ile Ser Asn
1               5                   10                  15

Gln Pro Val Asn Pro Arg Ser Leu Glu Lys Leu Glu Ile Ile Pro Ala
            20                  25                  30

Ser Gln Phe Cys Pro Arg Val Glu Ile Ile Ala Thr Met Lys Lys Lys
        35                  40                  45

Gly Glu Lys Arg Cys Leu Asn Pro Glu Ser Lys Ala Ile Lys Asn Leu
    50                  55                  60

Leu Lys Ala Val Ser Lys Glu Arg Ser Lys Arg Ser Pro Xaa
65                  70                  75
```

TREATING CANCER

CROSS-REFERENCE TO RELATED APPLICATION(S)

This application is a continuation divisional of U.S. patent application Ser. No. 14/105,628, filed on Dec. 13, 2013, now issued as U.S. Pat. No. 9,726,666, which is a continuation-in-part of International Patent Application No. PCT/GB2012/051357, filed on Jun. 13, 2012, which claims priority to U.S. Provisional Patent Application No. 61/496,442, filed on Jun. 13, 2011. U.S. patent application Ser. No. 14/105,628 is also a continuation-in-part of International Patent Application No. PCT/GB2012/051349, filed on Jun. 13, 2012, which claims priority to U.S. Provisional Patent Application No. 61/496,167, filed on Jun. 13, 2011. U.S. patent application Ser. No. 14/105,628 is also a continuation-in-part of International Patent Application No. PCT/GB2012/051348, filed on Jun. 13, 2012, which claims priority to U.S. Provisional Patent Application No. 61/496,288, filed on Jun. 13, 2011. U.S. patent application Ser. No. 14/105,628 is also a continuation-in-part of International Patent Application No. PCT/GB2012/051351, filed on Jun. 13, 2012, which claims priority to U.S. Provisional Patent Application No. 61/496,242, filed on Jun. 13, 2011. U.S. patent application Ser. No. 14/105,628 is also a continuation-in-part of International Patent Application No. PCT/GB2012/051350, filed on Jun. 13, 2012, which claims priority to U.S. Provisional Patent Application No. 61/496,209, filed on Jun. 13, 2011. U.S. patent application Ser. No. 14/105,628 is also a continuation-in-part of International Patent Application No. PCT/GB2012/051355, filed on Jun. 13, 2012, which claims priority to U.S. Provisional Patent Application No. 61/496,195, filed on Jun. 13, 2011. U.S. patent application Ser. No. 14/105,628 is also a continuation-in-part of International Patent Application No. PCT/GB2012/051345, filed on Jun. 13, 2012, which claims priority to U.S. Provisional Patent Application No. 61/496,228, filed on Jun. 13, 2011. U.S. patent application Ser. No. 14/105,628 is also a continuation-in-part of International Patent Application No. PCT/GB2012/051352, filed on Jun. 13, 2012, which claims priority to U.S. Provisional Patent Application No. 61/496,264, filed on Jun. 13, 2011. U.S. patent application Ser. No. 14/105,628 is also a continuation-in-part of International Patent Application No. PCT/GB2012/051346, filed on Jun. 13, 2012, which claims priority to U.S. Provisional Patent Application No. 61/496,184, filed on Jun. 13, 2011. U.S. patent application Ser. No. 14/105,628 is also a continuation-in-part of International Patent Application No. PCT/GB2012/051353, filed on Jun. 13, 2012, which claims priority to U.S. Provisional Patent Application No. 61/496,329, filed on Jun. 13, 2011. U.S. patent application Ser. No. 14/105,628 is also a continuation-in-part of International Patent Application No. PCT/GB2012/051356, filed on Jun. 13, 2012, which claims priority to U.S. Provisional Patent Application No. 61/496,377, filed on Jun. 13, 2011. U.S. patent application Ser. No. 14/105,628 is also a continuation-in-part of International Patent Application No. PCT/GB2012/051354, filed on Jun. 13, 2012, which claims priority to U.S. Provisional Patent Application No. 61/496,352, filed on Jun. 13, 2011. The entire contents of each of these applications are fully incorporated herein by reference.

INCORPORATION-BY-REFERENCE OF MATERIAL SUBMITTED ELECTRONICALLY

The instant application contains a Sequence Listing which has been submitted in ASCII format via EFS-Web and is hereby incorporated by reference in its entirety. Said ASCII copy, created on Jun. 21, 2017, is named P81602721US00-211226-9005-US01-SEQ-LIST-06-21-17.txt, and is 30,548 bytes in size.

FIELD OF THE INVENTION

The various embodiments of the present invention relate to products for and methods of treating cancer, in particular by reducing levels of circulating tumour cells, reducing the incidence of tumour metastasis, removing regulatory T lymphocytes from the peripheral blood, or treating leukaemias such as chronic lymphocytic leukaemia and chronic myeloic leukemia. The products and methods may also be used for debulking in Acute Myeloid Leukemia (AML), Acute Lymphoblastic Leukemia (ALL) and before harvest for autologous bone marrow/stem cell transplantation and for treating the leukemic phase of lymphoma. Companion diagnostics are also described.

BACKGROUND OF THE INVENTION

Cancer is a disease characterised by uncontrolled cell growth caused by accumulation of genetic mutations in the cellular DNA. There are over 200 types of different cancer classified according to the cell of origin from which the cancer or tumour first developed. Furthermore, cancers can be classified broadly as either solid tumours, for example breast cancer, colorectal cancer and melanoma, or as haematological malignancies such as leukaemias and lymphomas.

Solid tumours typically initiate and grow as an abnormal mass at a local site. However, during the course of cancer progression, the cells may acquire the ability to invade the underlying tissue and thereby enter the circulatory and/or lymphatic systems. These invasive properties ultimately allow solid tumours to metastasise to distal sites within the body, and it is metastasis combined with growth at secondary sites that accounts for the vast majority of cancer deaths.

In contrast to solid tumours, cancers such as leukaemias and lymphomas derive from cells of haematological origin, and therefore manifest as systemic diseases. In particular, chronic lymphocytic leukaemia, the most common form of leukaemia, develops from malignant lymphocytes originating in the bone marrow.

The body has many intrinsic mechanisms intended to guard against cancer development. In this regard, the immune system is thought to play a key role in eradicating cells harbouring genetic mutations. It follows therefore, that cancer cells often persist by evolving ways to avoid recognition by the cells of the immune system. In particular, it has been shown that elevated levels of T regulatory cells, both within the peripheral circulation and within the tumour microenvironment, underlie the immune suppression seen in cancer patients. The presence of increased numbers of regulatory T cells has also been identified as a barrier to the successful implementation of cancer immunotherapies.

Apheresis is a treatment used for depletion of blood components, such as antibodies, low-density lipoproteins (LDL) and blood cells. Leukapheresis is the apheresis treatment used for removal of white blood cells, leukocytes. The patient is connected to an extracorporeal blood circulating system; the blood is drawn from a vein in one arm, passed through a column device and returned into the other arm of the patient. WO2010/029317 describes apheresis columns useful for treating inflammatory conditions including a chemokine immobilised on a solid support.

SUMMARY OF THE INVENTION

Chemokines are a class of cytokine molecules involved in cell recruitment and activation in inflammation. Chemokines cause chemotaxis and activation of various subpopulations of cells in the immune system. The activity of chemokines is mediated primarily through tight binding to their receptors on the surface of leukocytes. In certain embodiments the present invention is based on the realisation that the interaction between chemokines and cells expressing their receptors may be exploited for the treatment of various cancers and components thereof, such as by reducing levels of circulating tumour cells, reducing the incidence of tumour metastasis, removing regulatory T lymphocytes (which may be referred to herein as "Tregs") from the peripheral blood, or treating leukaemias such as chronic lymphocytic leukaemia, chronic myeloid leukemia, use for debulking in AML, ALL and before harvest for autologous bone marrow/stem cell transplantation and for treating the leukemic phase of lymphoma. The inventors have determined that targeting specific chemokine receptor-expressing cells presents a new therapeutic approach to treat such conditions. Moreover, in such conditions, chemokine receptor expression on each cell may be increased again providing a therapeutic approach to treat such conditions. It is shown herein that cancer patients, in particular subjects suffering from UBC and PC, exhibit an increased frequency of CCR4 expressing circulating Tregs and that this response is specific to Tregs (and does not apply to other T lymphocytes). CCR4 expressing cells may thus be targeted in order to treat cancer. Treatment may rely upon suitable binding reagents such as CCL22 (MDC) and derivatives thereof, as described herein in further detail. It is also shown herein that subject suffering from leukemias, such as CLL, have a highly increased number of circulating (leukemic) B cells. The leukemic B cells express characteristic chemokine receptors, such as CCR7. It is also shown herein that CCR7 expressing B cells may be efficiently depleted using MIP3b as a specific binding reagent in a leukapheresis method.

Thus, in certain embodiments the invention serves to reduce the levels of circulating tumour cells, reduce the incidence of tumour metastasis, remove regulatory T lymphocytes from the peripheral blood or treat leukaemias such as chronic lymphocytic leukaemia, chronic myeloid leukemia. In certain embodiments the invention may also be used for debulking in AML, ALL and before harvest for autologous bone marrow/stem cell transplantation and to treat the leukemic phase of lymphoma. This is achieved using specific binding reagents to capture specific chemokine receptor-expressing cancer cells and regulatory T lymphocytes from the patient. Accordingly, in certain embodiments the invention provides in a first aspect a method for treating cancer comprising applying peripheral blood from a patient to an apheresis column loaded with a solid support comprising one or more binding reagents capable of specifically binding to one or more chemokine receptors, in particular the chemokine receptors CCR5, CCR6, CCR7, CCR8, CXCR4, CXCR7, CCR4, CCR9, CCR10, CXCR3 and/or CXCR5, immobilized directly or indirectly on the support thus removing one or more chemokine receptor, in particular one or more of CCR5, CCR6, CCR7, CCR8, CXCR4, CXCR7, CCR4, CCR9, CCR10, CXCR3 and/or CXCR5, expressing cells from the peripheral blood of the patient. The peripheral blood from which the chemokine receptor expressing cells have been removed may then be returned to the patient in order to complete the treatment. In certain embodiments the invention may thus rely on a continuous extracorporeal circuit in some embodiments. Alternatively, in other embodiments the invention may comprise steps of obtaining peripheral blood from the patient, applying the peripheral blood to the column and subsequently returning the peripheral blood from which the chemokine receptor expressing cells have been removed to the patient.

Herein, reference to CCR5, CCR6, CCR7, CCR8, CXCR4, CXCR7, CCR4, CCR9, CCR10, CXCR3 and/or CXCR5 is intended to encompass selection of any one or more, up to all, of the chemokine receptors listed. In addition, the combination of CCR5, CCR6, CCR7, CCR8, CXCR4 and/or CXCR7 is explicitly contemplated as a separate grouping, to include any one or more of CCR5, CCR6, CCR7, CCR8, CXCR4 and CXCR7.

Thus, the direct treatment of cancer relies upon removal of tumor cells expressing CCRs. The CCRs may be restricted to/accumulated on Leukemic cells. In certain embodiments the invention also reflects (encompasses) the removal of (normal) regulatory T cells that have been induced by the tumor as a tumor escape mechanism as an approach to treatment, which may be performed in addition to or as an alternative to direct treatment.

In certain embodiments the invention therefore also provides a method for treating cancer comprising applying peripheral blood from a patient to an apheresis column loaded with a solid support comprising one or more binding reagents capable of specifically binding to one or more regulatory T cell receptors, which may have been identified as being up-regulated in cancer, in particular the cutaneous lymphocyte antigen (CLA) receptor or chemokine receptors expressed on Tregs such as CCR4 and CCR8, immobilized directly or indirectly on the support thus removing one or more regulatory T cell receptor expressing cells from the peripheral blood of the patient. The peripheral blood from which the regulatory T cell receptor expressing cells have been removed may then be returned to the patient in order to complete the treatment. The invention may thus rely on a continuous extracorporeal circuit in some embodiments. Alternatively, in other embodiments the invention may comprise steps of obtaining peripheral blood from the patient, applying the peripheral blood to the column and subsequently returning the peripheral blood from which the regulatory T cell receptor expressing cells have been removed to the patient.

Herein, reference to CLA, CCR4 and/or CCR8 is intended to encompass selection of any one or more, up to all, of the chemokine receptors listed. In addition, the combination of CLA, CCR4 and/or CCR8 is explicitly contemplated as a separate grouping to the CCR5, CCR6, CCR7, CCR8, CXCR4, CXCR7, CCR4, CCR9, CCR10, CXCR3 and/or CXCR5 grouping also described herein.

Tregs may be recruited to the tumour by chemokines such as CCL17 and CCL22 binding to CCR4 expressed on the Treg, or CCR8 mediated recruitment by CCL1 may occur for example. Thus, in certain embodiments the invention may also rely upon one or more binding reagents capable of specifically binding to one or more chemokine receptors, such as CCR4 and CCR8. As discussed below, the binding reagents may comprise one or more chemokines. CCL17 and CCL22 may be utilised for the removal of CCR4 expressing Tregs and CCL1 may be utilised for the removal of CCR8 expressing Tregs.

The expression of chemokine receptors may vary from leukaemia to leukaemia. For example, the difference between a leukaemia with circulating cells and lymphoma with lymph node malignant cell may lie in the expression of CCR7 allowing entrance into the lymph node. When lymphoma enters into a leukemic phase it is likely due to down-regulation of CCR7. Accordingly, in other embodiments the invention also provides a method for treating leukemia comprising applying peripheral blood from a patient to an apheresis column loaded with a solid support comprising one or more binding reagents capable of specifically binding to one or more chemokine receptors, which have been identified as being linked to leukemia, for example up-regulated in leukemia, immobilized directly or indirectly on the support thus removing one or more chemokine receptor expressing cells from the peripheral blood of the patient. Suitable chemokine receptor expressing cells can be identified by applying the methods described herein.

As shown herein, suitable binding reagents can be immobilized onto a solid support, either directly or indirectly, to generate an apheresis column suitable for capturing relevant chemokine receptor-expressing cells. Where increased levels of chemokine receptor expression are observed, such cells may be preferably removed from the peripheral blood using the columns of the various embodiments of the invention. Thus, the methods of various embodiments of the invention may preferably target one or more of CCR5hi, CCR6hi, CCR7hi, CCR8hi, CXCR4hi, CXCR7hi, CCR4hi, CCR9hi, CCR10hi, CXCR3hi and/or CXCR5hi cells as defined herein for removal from the peripheral blood. "High" expression may be determined according to standard flow cytometry techniques. The level is measured relative to levels of expression of the chemokine receptor in cells taken from a healthy subject. FIG. 5 provides an example of a gating strategy.

In certain embodiments the invention further provides a binding reagent capable of specifically binding to one or more chemokine receptors, in particular to a chemokine receptor/the chemokine receptor CCR5, CCR6, CCR7, CCR8, CXCR4, CXCR7, CCR4, CCR9, CCR10, CXCR3 and/or CXCR5, for use in the treatment of cancer, wherein the one or more binding reagents is immobilized, directly or indirectly, on a solid support contained within an apheresis column, to which is applied peripheral blood from a patient thus removing one or more chemokine receptor/CCR5, CCR6, CCR7, CCR8, CXCR4, CXCR7, CCR4, CCR9, CCR10, CXCR3 and/or CXCR5 expressing cells from the peripheral blood of the patient. In other embodiments the invention also provides for use of one or more binding reagents capable of specifically binding to a chemokine receptor/the chemokine receptor CCR5, CCR6, CCR7, CCR8, CXCR4, CXCR7, CCR4, CCR9, CCR10, CXCR3 and/or CXCR5 (for use) in the manufacture of an apheresis column for treatment of cancer, wherein the one or more binding reagents is immobilized on a solid support contained within the apheresis column, to which is applied peripheral blood from a patient thus removing one or more of chemokine receptor/CCR5, CCR6, CCR7, CCR8, CXCR4, CXCR7, CCR4, CCR9, CCR10, CXCR3 and/or CXCR5 expressing cells from the peripheral blood of the patient.

Similarly, as shown herein, suitable binding reagents can be immobilized onto a solid support, either directly or indirectly, to generate an apheresis column suitable for capturing relevant Treg receptor-expressing cells. Where increased levels of Treg receptor expression are observed, such cells may be preferably removed from the peripheral blood using the columns of the various embodiments of the invention. Thus, in certain embodiments the methods of the various embodiments of the invention may preferably target one or more of $CLA^{hi}$, $CCR4^{hi}$ and/or $CCR8^{hi}$ cells as defined herein for removal from the peripheral blood. "High" expression may be determined according to standard flow cytometry techniques. The level is measured relative to levels of expression of the Treg receptor in cells taken from a healthy subject. FIG. 5 provides an example of a gating strategy.

In other embodiments the invention further provides a binding reagent capable of specifically binding to one or more Treg receptors, in particular to the Treg receptor CLA, CCR4 and/or CCR8, for use in the treatment of cancer, wherein the one or more binding reagents is immobilized, directly or indirectly, on a solid support contained within an apheresis column, to which is applied peripheral blood from a patient thus removing one or more Treg receptor expressing cells from the peripheral blood of the patient. In certain embodiments the invention also provides for use of one or more binding reagents capable of specifically binding to a Treg receptor/the Treg receptor CLA, CCR4 and/or CCR8 (for use) in the manufacture of an apheresis column for treatment of cancer, wherein the one or more binding reagents is immobilized on a solid support contained within the apheresis column, to which is applied peripheral blood from a patient thus removing one or more of Treg receptor/CLA, CCR4 and/or CCR8 expressing cells from the peripheral blood of the patient.

All embodiments described in respect of the methods of treatment of the various embodiments of the invention apply to these aspects mutatis mutandis and are not repeated for reasons of conciseness. Thus, the following discussion made with reference to the methods of treatment is also applicable to the medical use aspects of the various embodiments of the invention.

In certain embodiments the invention aims to treat a range of specific cancer, or cancer-related, conditions. Specific conditions may be selected from reducing levels of circulating tumour cells, reducing the incidence of tumour metastasis, removing regulatory T lymphocytes from the peripheral blood, or treating leukaemias such as chronic lymphocytic leukaemia, chronic myeloid leukemia, use for debulking in AML, ALL and before harvest for autologous bone marrow/stem cell transplantation and treating the leukemic phase of lymphoma. Reducing levels of circulating tumour cells may be applicable to a range of cancers. This aspect may be relevant to certain solid tumours such as breast cancer, colon cancer or lung cancer. Reducing the incidence of tumour metastasis may rely upon preventing metastatic cell entry at specific locations, since this may be driven via chemokine-chemokine receptor interactions. Thus, in certain embodiments the methods of the invention may be utilized to prevent entry of metastatic cells into any one or more of bone, lungs, lymph nodes, skin and small intestine. In specific embodiments, CXCR4 expressing cells are targeted to prevent metastatic cell entry into the bone and/or lungs. In other embodiments, CCR7 expressing cells are targeted to prevent metastatic cell entry into the lymph nodes. In further embodiments, CCR10 expressing cells are targeted to prevent metastatic cell entry into the skin. In yet further embodiments, CCR9 expressing cells are targeted to prevent metastatic cell entry into the small intestine.

Removal of regulatory T lymphocytes (which may be referred to herein as "Tregs") from the peripheral blood may assist with immune system recognition of the cancer or tumour. T regulatory cells (Tregs) are a subpopulation of T cells that suppress the immune system in order to maintain immune homeostasis. In cancer, the Tregs can inhibit an effective immune response against the tumor and thus removal of the Tregs may lead to an improved immune activation against the cancer cells. In certain embodiments this aspect of the invention may thus be applicable to treating any cancer. Specific examples include pancreatic cancer and bladder cancer, in particular urinary bladder cancer.

In certain embodiments the methods of the invention may also be utilized in combination with other forms of therapy, such as chemotherapies. Debulking using the leukaphereis procedure may decrease the need for chemotherapy and therefore diminish side effects.

Treating leukaemias such as chronic lymphocytic leukaemia and chronic myeloid leukemia may be based upon direct removal of cancerous cells in the peripheral blood. Use for debulking in AML and ALL may rely upon the targeted cytoreductive effects achieved by the various embodiments of the present invention. Similarly, removal of cancerous cells or cells contributing to the cancerous condition (such as Tregs) may be useful prior to harvest of bone marrow or stem cells from a subject or patient for autologous bone marrow/stem cell transplantation. In certain embodiments the invention may also be useful for treating the leukemic phase of lymphoma, when excess lymphocytes are found in the peripheral blood. The excess lymphocytes, which may include Tregs, can be removed on the basis of the cells expressing particular receptors, especially chemokine receptors.

Leukemia, in particular Acute lymphoblastic leukemia (ALL), may be treated by targeting CXCR4 and/or CXCR3 expressing cells. Leukemia, in particular Chronic myelogenous leukemia (CML), may be treated by targeting CXCR4, CXCR5 and/or CXCR3 expressing cells.

By treatment is meant a reduction in the specific chemokine receptor expressing cells in the peripheral blood of the patient. The reduction may comprise a reduction in cells that express chemokine receptors, in particular one or more of CCR5, CCR6, CCR7, CCR8, CXCR4, CXCR7, CCR4, CCR9, CCR10, CXCR3 and/or CXCR5, at increased levels in diseased patients. The patient is typically a human patient but the term patient may include both human and non-human animal subjects in some embodiments. In the context of the various embodiments of the present invention, this typically involves a reduction in one or more of CCR5, CCR6, CCR7, CCR8, CXCR4, CXCR7, CCR4, CCR9, CCR10, CXCR3 and/or CXCR5 expressing cells, such as one or more of $CCR5^{hi}$, $CCR6^{hi}$, $CCR7^{hi}$, $CCR8^{hi}$, $CXCR4^{hi}$, $CXCR7^{hi}$, $CCR4^{hi}$, $CCR9^{hi}$, $CCR10^{hi}$, $CXCR3^{hi}$ and/or $CXCR5^{hi}$ expressing cells, in the peripheral blood of the patient. The CCR5, CCR6, CCR7, CCR8, CXCR4, CXCR7, CCR4, CCR9, CCR10, CXCR3 and/or CXCR5 expressing cells comprise, consist essentially of or consist of tumour cells, central memory T lymphocytes and regulatory T lymphocytes, in certain embodiments. Tumour cells may be derived from leukemia in certain embodiments, such as chronic lymphocytic leukaemia, in particular B-CLL (B-cell chronic lymphocytic leukemia), chronic myeloid leukemia, AML, ALL and the leukemic phase of lymphoma. In certain embodiments the invention may, for example, rely generally upon the removal of leukemic B-cells. B-cells may be characterised as CD19 posivtive cells.

Treatment in the context of Treg focused applications specifically relies upon a reduction in the specific Treg receptor expressing cells in the peripheral blood of the patient. The reduction may comprise a reduction in cells that express Treg receptors, in particular one or more of CLA, CCR4 and/or CCR8, at increased levels in diseased patients. The patient is typically a human patient but the term patient may include both human and non-human animal subjects in some embodiments. In the context of the present invention, this typically involves a reduction in one or more of CLA, CCR4 and/or CCR8 expressing cells, such as one or more of "$CLA^{hi}$, $CXCR4^{hi}$ and/or $CXCR8^{hi}$" expressing cells, in the peripheral blood of the patient. It is shown herein that cancer patients exhibit an increased frequency of CCR4 expressing circulating Tregs and that this response is specific to Tregs (and does not apply to other T lymphocytes). CCR4 expressing cells may be targeted using suitable binding reagents such as CCL22 (MDC) and derivatives thereof, as described herein in further detail.

The three major types of lymphocyte are T cells, B cells and natural killer (NK) cells. The term "T-lymphocyte" includes $CD4^+$ T cells such as T helper cells (Th1 cells and Th2 cells), and $CD8^+$ T cells such as cytotoxic T cells. Th1 cells may be characterized by expression of CCR5 and/or by production of IFN-γ. Th2 cells may be characterized by expression of CCR3 and/or by production of IL-4. Regulatory T cells (Tregs) express the transcription factor FoxP3 and express high levels of the IL-2Ra (CD25) on the cell surface. In addition they have down-regulated levels of the IL-7a receptor CD127. Thus, Tregs can be defined as CD4+ CD25hiCD127lo/− and Foxp3 positive. The function of Tregs is to regulate and modulate T effector cell responses by direct and indirect contacts mediated by cytokines. Thus, tumors induce Tregs in order to avoid recognition and elimination by T effector cells as a tumor escape mechanism.

In certain embodiments the methods of the invention may involve specific binding interactions with any one or more of these further cell-surface (and cell-specific) markers in addition to the removal based upon binding to chemokine receptors such as CCR5, CCR6, CCR7, CCR8, CXCR4, CXCR7, CCR4, CCR9, CCR10, CXCR3 and/or CXCR5 and/or Treg receptors such as CLA, CCR4 and/or CCR8. Suitable binding reagents can be prepared to specifically bind to these cell-surface markers. The discussion of (chemokine receptor, in particular CCR5, CCR6, CCR7, CCR8, CXCR4, CXCR7, CCR4, CCR9, CCR10, CXCR3 and/or CXCR5; and/or Treg receptor) specific binding reagents thus applies mutatis mutandis.

CCR5 is the gene symbol approved by the HUGO Gene Nomenclature Committee for chemokine (C-C motif) receptor 5. The HGNC ID for this gene is 1605. The gene is located at chromosome position 3p21. The previous symbol and name for the gene is CMKBR5. Synonyms for this gene include CC-CKR-5, CD195 CKR-5, IDDM22 and CKR5. The Entrez Gene reference sequence for CCR5 is 1234 as available on 13 Jun. 2011, which is incorporated herein by reference in its entirety.

CCR6 is the gene symbol approved by the HUGO Gene Nomenclature Committee for chemokine (C-C motif) receptor 6. The HGNC ID for this gene is 1607. The gene is located at chromosome position 6q27. The previous symbol and name for the gene is STRL22. Synonyms for this gene include BN-1, CD196, CKR-L3, CMKBR6, DCR2, DRY-6, GPR-CY4, GPR29. The Genbank reference sequence for CCR6 is U68030.1 as available on 13 Jun. 2011, which is incorporated herein by reference in its entirety.

CCR7 is the gene symbol approved by the HUGO Gene Nomenclature Committee for chemokine (C-C motif) receptor 7. The HGNC ID for this gene is 1608. The gene is located at chromosome position 17q12-q21.2. The previous symbol and name for the gene is CMKBR7, EBI1. Synonyms for this gene include BLR2, CD197 and CDw197.

The RefSeq reference sequence for CCR1 is NM_001838.3 as available on 13 Jun. 2011, which is incorporated herein by reference in its entirety.

CCR8 is the gene symbol approved by the HUGO Gene Nomenclature Committee for chemokine (C-C motif) receptor 8. The HGNC ID for this gene is 1609. The gene is located at chromosome position 3p22. The previous symbol and name for the gene is CMKBR8, CMK. Synonyms for this gene include CDw198, CKR-L1, CY6, GPR-CY6, TER1. The Genbank reference sequence for CCR8 is D49919.1 as available on 13 Jun. 2011, which is incorporated herein by reference in its entirety.

CXCR4 is the gene symbol approved by the HUGO Gene Nomenclature Committee for chemokine (C-X-C motif) receptor 4. The HGNC ID for this gene is 2561. The gene is located at chromosome position 2q21. The previous symbol and name for the gene is "chemokine (C-X-C motif), receptor 4 (fusin)". Synonyms for this gene include CD184, D2S201E, fusin, HM89, HSY3RR, LESTR, NPY3R, NPYR, NPYY3R. The Genbank reference sequence for CXCR4 is AJ132337.1 as available on 13 Jun. 2011, which is incorporated herein by reference in its entirety.

CXCR7 is the gene symbol approved by the HUGO Gene Nomenclature Committee for chemokine (C-X-C motif) receptor 7. The HGNC ID for this gene is 23692. The gene is located at chromosome position 2q37.3. The previous symbol and name for the gene is "chemokine orphan receptor 1", CMKOR1. Synonyms for this gene include GPR159 and RDC1. The Genbank reference sequence for CXCR7 is BC008459.1 as available on 13 Jun. 2011, which is incorporated herein by reference in its entirety.

CCR4 is the gene symbol approved by the HUGO Gene Nomenclature Committee for chemokine (C-C motif) receptor 4. The HGNC ID for this gene is 1605. The gene is located at chromosome position 3p24-p21.3. Synonyms for this gene include CC-CKR-4, CD194, ChemR13, CKR4, CMKBR4, k5-5. The Genbank reference sequence for CCR4 is X85740.1 as available on 4 Apr. 2012, which is incorporated herein by reference in its entirety.

Cutaneous lymphocyte antigen (CLA herein) is a specialized form of PSGL-1 expressed on skin-homing T cells, see Fuhlbrigge et al., Nature 389, 978-981 (30 Oct. 1997)|doi: 10.1038/40166 (incorporated herein by reference in its entirety). Memory T cells that infiltrate the skin express a unique skin-homing receptor called cutaneous lymphocyte-associated antigen (CLA), a carbohydrate epitope that facilitates the targeting of T cells to inflamed skint, CLA is an inducible carbohydrate modification of P-selectin glycoprotein ligand-1 (PSGL-1), a known surface glycoprotein that is expressed constitutively on all human peripheral-blood T cells.

CXCR3 is the gene symbol approved by the HUGO Gene Nomenclature Committee for chemokine (C-X-C motif) receptor 3. The HGNC ID for this gene is 4540. The gene is located at chromosome position Xq13. The previous symbol and name for the gene is "G protein-coupled receptor 9", GPR9. Synonyms for this gene include CD183, CKR-L2, CMKAR3, IP10-R and MigR. The Genbank reference sequence for CXCR3 is U32674.1 as available on 13 Jun. 2011, which is incorporated herein by reference in its entirety.

CXCR5 is the gene symbol approved by the HUGO Gene Nomenclature Committee for chemokine (C-X-C motif) receptor 5. The HGNC ID for this gene is 1060. The gene is located at chromosome position 11q23.3. The previous symbol and name for the gene is BLR1, "Burkitt lymphoma receptor 1, GTP binding protein (chemokine (C-X-C motif) receptor 5)", "Burkitt lymphoma receptor 1, GTP-binding protein". Synonyms for this gene include CD185, MDR15. The Genbank reference sequence for CXCR4 is X68829.1 as available on 29 May 2012, which is incorporated herein by reference in its entirety.

CCR9 is the gene symbol approved by the HUGO Gene Nomenclature Committee for chemokine (C-C motif) receptor 9. The HGNC ID for this gene is 1610. The gene is located at chromosome position 3p22. The previous symbol and name for the gene is GPR28. Synonyms for this gene include CDw199, GPR-9-6. The Genbank reference sequence for CCR9 is AJ132337.1 as available on 13 Jun. 2011, which is incorporated herein by reference in its entirety.

CCR10 is the gene symbol approved by the HUGO Gene Nomenclature Committee for chemokine (C-C motif) receptor 10. The HGNC ID for this gene is 4474. The gene is located at chromosome position 17p21.1-q21.3. The previous symbol and name for the gene is "G protein-coupled receptor 2", GPR2. The Genbank reference sequence for CCR9 is AF215981.1 as available on 29 May 2012, which is incorporated herein by reference in its entirety.

Treatment according to the various embodiments of the invention may result in alleviation or amelioration of symptoms, prevention of progression, regression of the condition, or complete recovery. Measurable parameters of successful treatment include one or more, up to all, of: The number of circulating CD4+CD25hiCD127lo/− and Foxp3 positive cells will decrease and the functional activation of T effector cells in peripheral blood will increase as a sign of effective treatment. The number of circulating chemokine receptor expressing leukemic or tumor cells may decrease as a sign of effective leukapheresis. In specific embodiments, a single treatment is sufficient to cause a depletion of around 10%, 20%, 30%, 40%, 50%, 60% or 70%, or higher up to 80%, 90%, 95% or more, or any range of values between and including these amounts, of one or more of a specific chemokine receptor, in particular one or more of CCR5, CCR6, CCR7, CCR8, CXCR4, CXCR7, CCR4, CCR9, CCR10, CXCR3 and/or CXCR5, expressing cells from the peripheral blood of the patient. In specific embodiments, at least around 50% depletion is achieved in a single treatment. Thus, successful treatment may be defined with reference to depletion of one or more of CCR5, CCR6, CCR7, CCR8, CXCR4, CXCR7, CCR4, CCR9, CCR10, CXCR3 and/or CXCR5 expressing cells. Treatment may lead to depletion of between approximately 100 and 500 million CCR5, CCR6, CCR7, CCR8, CXCR4, CXCR7, CCR4, CCR9, CCR10, CXCR3 and/or CXCR5 expressing cells, such as cancer cells and regulatory T-lymphocytes, in certain embodiments, and more particularly to about 100, 150, 200, 250, 300, 350, 400, 450, or 500 million CCR5, CCR6, CCR7, CCR8, CXCR4, CXCR7, CCR4, CCR9, CCR10, CXCR3 and/or CXCR5 expressing cells. Similar depletion levels may apply to methods in which Treg receptor expressing cells (CLA, CCR4 and/or CCR8) are targeted.

By binding to the column through the binding reagent-chemokine receptor interaction, chemokine receptor expressing cells are immobilized. These immobilized cells may express further unoccupied chemokine receptors, which may be of the same or different type to those used for capture. These additional chemokine receptors may permit circulating chemokines which may contribute to the condition to be captured from the peripheral blood. Thus, a reduction in circulating (specific) chemokine levels may provide a measure of successful treatment, since for example chemokine down-regulation may diminish Treg recruitment.

The duration of treatment may be readily determined by one skilled in the art and will depend upon factors such as the flow rate of the peripheral blood. Duration of treatment may be tied into monitoring of the treatment itself, with the treatment considered complete once a measurable parameter of treatment has reached a defined threshold. Any suitable parameter may be employed as discussed herein. Thus, for example, treatment may be considered complete when a reduction in one or more of CCR5, CCR6, CCR7, CCR8, CXCR4, CXCR7, CCR4, CCR9, CCR10, CXCR3 and/or CXCR5 expressing cells, such as a 50% reduction in one or more of CCR5, CCR6, CCR7, CCR8, CXCR4, CXCR7, CCR4, CCR9, CCR10, CXCR3 and/or CXCR5 expressing cells, has been achieved. The apheresis system may be operated at a flow rate of around 10-80 mL/min, or more specifically between around 20-70 mL/min, or between around 30-60 mL/min. In specific embodiments, the treatment is performed for a period of around 10, 20, 30, 40, 50, 60, 70, 80, 90, 100, 110, 120 etc., or any range of values between and including these amounts, minutes. The treatment is typically not aimed to remove all of the cells expressing the chemokine receptor in the peripheral blood, as a basal level of those cells is required in healthy subjects. However, it has been found that only low blood volumes need to be applied to the columns of the invention in order to achieve effective levels of depletion of the chemokine receptor-expressing cells. Thus, in certain embodiments, around 10-90% or more specifically around 20, 30, 40, 50, 60, 70, 80 or 90%, or any range of values between and including these amounts, of the patient's blood is applied to the column in a single treatment. The volume of blood circulated through the apheresis column or system may be in the region of around 1000-3000 ml, such as around 1000, 1200, 1400, 1600, 1800 or 2000 ml or any range of values between and including these amounts. The treatment may be considered complete once this volume of blood has been circulated. The patient may be administered anticoagulants prior to each treatment session. A suitable solution, such as a sterile saline solution, optionally including an anticoagulant such as Heparin, may be used for priming the apheresis (extracorporeal) system. An additional volume of anticoagulant may be added to the circuit at the start of each treatment session, for example as a bolus injection. The same factors may be applied mutatis mutandis to aspects of the invention where Treg expressing cells are targeted (such as CLA, CCR4 and/or CCR8 expressing cells).

In certain embodiments the invention relies upon a binding reagent which is capable of specifically binding to a chemokine receptor, or to a regulatory T cell receptor in some embodiments. This specific binding reaction permits cells expressing the chemokine receptor or regulatory T cell receptor to be removed from the peripheral blood of the patient when the blood is passed over the solid support upon or within which the binding reagent is immobilized. Specific chemokine receptors of interest include CCR5, CCR6, CCR7, CCR8, CXCR4, CXCR7, CCR4, CCR9, CCR10, CXCR3 and/or CXCR5 (when treating cancers such as leukemias) and/or regulatory T cell receptors such as CLA, CCR4 and CCR8 (when specifically aiming to remove Tregs). The binding reagent can be any binding reagent capable of specifically binding to the receptor in question. By "specific binding" is meant that the binding reagent displays sufficient specificity of binding and appropriate binding affinity/kinetics to permit removal of cells expressing one or more of CCR5, CCR6, CCR7, CCR8, CXCR4, CXCR7, CCR4, CCR9, CCR10, CXCR3 and/or CXCR5, or a regulatory T cell receptor such as CLA, CCR4 and CCR8 from the peripheral blood (as appropriate). Whilst it is not precluded that the binding reagent is capable of binding to other molecules, such as other chemokine receptors, the binding reagent will preferentially bind to cells expressing one or more of CCR5, CCR6, CCR7, CCR8, CXCR4, CXCR7, CCR4, CCR9, CCR10, CXCR3 and/or CXCR5, or a regulatory T cell receptor such as CLA, CCR4 and CCR8 and in particular to cells expressing increased levels of one or more of CCR5, CCR6, CCR7, CCR8, CXCR4, CXCR7, CCR4, CCR9, CCR10, CXCR3 and/or CXCR5, or a regulatory T cell receptor such as CLA, CCR4 and CCR8 (as defined further herein). The binding reagent capable of specifically binding to CCR5, CCR6, CCR7, CCR8, CXCR4, CXCR7, CCR4, CCR9, CCR10, CXCR3 and/or CXCR5, or a regulatory T cell receptor such as CLA, CCR4 and CCR8 may be either an agonist or an antagonist of CCR5, CCR6, CCR7, CCR8, CXCR4, CXCR7, CCR4, CCR9, CCR10, CXCR3 and/or CXCR5, or a regulatory T cell receptor such as CLA, CCR4 and CCR8, respectively. As the disease condition may rely upon up-regulation of expression of, or signaling via, CCR5, CCR6, CCR7, CCR8, CXCR4, CXCR7, CCR4, CCR9, CCR10, CXCR3 and/or CXCR5, or a regulatory T cell receptor such as CLA, CCR4 and CCR8, in certain embodiments the binding reagent capable of specifically binding to CCR5, CCR6, CCR7, CCR8, CXCR4, CXCR7, CCR4, CCR9, CCR10, CXCR3 and/or CXCR5, or a regulatory T cell receptor such as CLA, CCR4 and CCR8 is an antagonist of CCR5, CCR6, CCR7, CCR8, CXCR4, CXCR7, CCR4, CCR9, CCR10, CXCR3 and/or CXCR5, or a regulatory T cell receptor such as CLA, CCR4 and CCR8, respectively. Chemokines are typically, although not necessarily exclusively (particularly in the case of truncated or modified forms) agonists of their cognate receptor and serve to activate the cells expressing the relevant receptor, as would be appreciated by one skilled in the art. Antibodies against the relevant chemokine receptor are generally considered to be antagonists, as would be appreciated by one skilled in the art. Specific examples of binding reagents include proteins or polypeptides, such as antibodies and receptor ligands, in particular chemokines. The binding reagent may be a nucleic acid molecule in certain embodiments. In some embodiments, the nucleic acid is an aptamer. Nucleic acid aptamers are polynucleotides of approximately 15-40 nucleotides long. Nucleic acid aptamers can be made using the SELEX process (systemic evolution of ligands by exponential enrichment) or any other process known to those of skill in the art. For CLA the binding reagent may be based upon a known binding agent such as vascular lectin endothelial cell-leukocyte adhesion molecule 1 (ELAM-1). The discussion of modified truncated chemokines herein applies mutandis mutandis to the ELAM-1 binding reagent for CLA.

In other embodiments, the binding reagent may be a peptide, and in certain instances, a peptide aptamer. Peptide aptamers are artificial recognition molecules that consist of a variable peptide sequence inserted into a constant scaffold protein (Baines I C, Colas P. Peptide aptamers as guides for small molecule drug discovery. Drug Discov Today. 2006; 11:334-341, incorporated herein by reference). A number of methodologies, such as phage display, ribosome display and yeast two-hybrid screening systems are available for screening a library of potential peptide-based binding agents. Similarly protein scaffolds based on domains such as fibronectins, ankyrin repeats, protein A, SH3 domains, lipocalins and ubiquitin can be used as the binding agent. Again a number of technologies such as phage display and ribosome display are available for screening a library of protein-based binding agents. Similarly, libraries of candidate chemical compounds can be screened for specific binding to the relevant chemokine receptor using suitable screening techniques known in the art, which may be high throughput screens in certain embodiments. The candidate binding agent may be immobilized on a solid support and the ability of the agent to specifically retain cells expressing the chemokine receptor of interest or labelled chemokine receptors determined. A range of cell types may be applied to the solid supports to confirm specificity of binding, or alternatively a mixed sample (such as peripheral blood) may be applied to the solid support. Retention of the cell type of interest (expressing the appropriate chemokine receptor) can be confirmed to identify suitable binding agents.

In the context of the various embodiments of the present invention the term "chemokine" also comprises biotinylated or otherwise labelled chemokines. The term "chemokine" also comprises modified and truncated versions of the chemokine and chemokine fragments with the proviso that the modified or truncated form retains its ability to bind to its cognate receptor (and thus remains functional in the context of the invention). The chemokine does not necessarily need to retain biological activity as it is specific binding affinity for CCR5, CCR6, CCR7, CCR8, CXCR4, CXCR7, CCR4, CCR9, CCR10, CXCR3 and/or CXCR5 and/or for CCR4 and CCR8 where Tregs are specifically targeted that is required. In certain embodiments, the chemokine lacks biological activity, for example in terms of activation of the (CCR5, CCR6, CCR7, CCR8, CXCR4, CXCR7, CCR4, CCR9, CCR10, CXCR3 and/or CXCR5; or CCR4 or CCR8 when specifically targeting Tregs) receptor.

Modifications may be made to improve protein synthesis, for example uniformity of product and yield. As known to those skilled in the art, exemplary modifications may comprise amino acid additions, substitutions, deletions or other modifications to one or more amino acids in the chemokine. Modifications may comprise substitution of the wild type amino acid with non-natural amino acids such as norleucine (NLeu) and derivatized amino acids such as pyroglutamic acid (pyroGlu). Such modifications may be made to minimize side-product formation during storage and use of the columns of the various embodiments of the invention. Modifications may be made to improve labelling, for example inclusion of a polyethylene glycol (PEG) spacer to facilitate biotinylation. The biotinylation and/or conjugation with fluorochromes or other labelling groups of the chemokine is performed in a manner which does not substantially affect the receptor binding capacity. Site specific biotinylation or other labelling is preferred as non-selective labelling of chemokines may compromise receptor binding activity. Bioinylation or other labelling is generally preferred at or towards the C-terminus of the protein as the inventors have found that modifications in this area are generally well tolerated (in terms of a minimal effect on receptor binding capability). Biotinylation may be carried out site-specifically at any suitable amino acid. Examples of suitable amino acids include lysine and ornithine. Generally, reference may be made to Natarajan S et al, Int. J. Pept. Protein Res., 1992, 40, 567-74; Baumeister B, Int. J. Peptide Res. And Therapeutics, 2005, 11, 139-141; Bioconjugate techniques $2^{nd}$ edition, Greg T. Hermanson, incorporated by reference herein in its entirety.

Truncations may involve deletion of either N or C terminal amino acids as appropriate, or both. Typically, the truncated version will retain the residues required for the chemokine to fold correctly, for example to retain a chemokine fold structure, consistent with the requirement that a truncated version must retain the ability to bind to the relevant receptor (expressed by (on the surface of) a leukocyte). Chemokine molecules typically include disulphide bonds between the $1^{st}$ and $3^{rd}$ and $2^{nd}$ and $4^{th}$ cysteine residues respectively, as would be understood by one skilled in the art. Where sequences are presented herein, it is assumed that these disulphide bonds will form in the folded protein (unless otherwise stated). Truncated versions may comprise anywhere between 1 and 100 less amino acids, such as 1, 2, 3, 4, 5 etc amino acids, than the wild type amino acid sequence in certain embodiments. Of course, truncated versions may comprise further modification as detailed herein. The modified or truncated version may have 40%, 45%, 50%, 55%, 60%, 65%, 70%, 75%, 80%, 85%, 90%, 95% or more overall amino acid sequence identity with the full length wild type chemokine (where a deletion is counted as a difference in amino acid sequence) in certain embodiments. Over the common sequence between the molecules (i.e the amino acids that have not been deleted), there may be 80%, 85%, 90%, 91%, 92%, 93%, 94%, 95%, 96%, 97%, 98% or 99% amino acid sequence identity in certain embodiments. Sequence identity may be determined using known algorithms, such as BLAST or GAP analysis (GCG Program) (applying default settings), which are freely available. Chemokines may lack the N-terminal signal peptide which is cleaved off during synthesis in vivo.

Specific chemokines useful in the various embodiments of the present invention for binding to CCR5, CCR6, CCR7, CCR8, CXCR4, CXCR7, CCR4, CCR9, CCR10, CXCR3 and/or CXCR5 include MIP-3alpha (CCL20), CCL19, CCL21, CCL1, CXCL11, CXCL12, CCL25 (TECK), CCL27 (CTACK), CCL28 (MEC), CXCL9 (MIG), CXCL10 (IP10), CXCL13 (BCA-1), CCL17 (TARC) and CCL22 (MDC). Herein, reference to MIP-3alpha (CCL20), CCL19, CCL21, CCL1, CXCL11, CXCL12, CCL25 (TECK), CCL27 (CTACK), CCL28 (MEC), CXCL9 (MIG), CXCL10 (IP10), CXCL13 (BCA-1), CCL17 (TARC) and CCL22 (MDC) is intended to encompass selection of any one or more, up to all, of the chemokines listed. In addition, the combination of MIP-3alpha (CCL20), CCL19, CCL21, CCL1, CXCL11 and CXCL12 is explicitly contemplated as a separate grouping, to include any one or more of MIP-3alpha (CCL20), CCL19, CCL21, CCL1, CXCL11 and CXCL12. In addition, the combination of CCL25 (TECK), CCL27 (CTACK), CCL28 (MEC), CXCL9 (MIG), CXCL10 (IP10), CXCL11 (ITAC), CXCL13 (BCA-1), CCL17 (TARC) and CCL22 (MDC) is explicitly contemplated as a separate grouping, to include any one or more of CCL25 (TECK), CCL27 (CTACK), CCL28 (MEC), CXCL9 (MIG), CXCL10 (IP10), CXCL11 (ITAC), CXCL13 (BCA-1), CCL17 (TARC) and CCL22 (MDC).

CCL3, CCL4, CCL5 and CCL8 bind CCR5. CCL20 binds CCR6 (only). CCL19 and CCL21 bind CCR7. CXCL12 bind CXCR4. CCL1 binds CCR8. CXCL11 and CXCL12 bind CXCR7. CCL17 and CCL22 each bind to CCR4. CCL25 (TECK) binds to CCR9. CCL27 (CTACK) and CCL28 (MEC) each bind CCR10. CXCL9 (MIG), CXCL10 (IP10) and CXCL11 (ITAC) bind CXCR3. CXCL13 (BCA-1) binds CXCR5. CCL17 (TARC) and CCL22 (MDC) bind CCR4 only.

The modified and truncated chemokines described in greater detail herein (with reference to the relevant amino acid sequences, as set forth in the SEQ ID NOs and accompanying experimental examples) may each be applied according to the various embodiments of the present invention. Such modified forms may instruct the skilled person regarding additional modified forms of the same and other chemokines which may be suitable for use in the various embodiments of the invention. Chemokines show variable sequence homology varying from less than 20% to over 90% but all share very similar tertiary structures consisting of a disordered N-terminus, followed by a long loop (the N-loop) that ends in a $3_{10}$ helix, a 3-stranded β-sheet and a C-terminal helix. The overall topology is stabilized by disulphide bonds. This common tertiary structure is a common feature of the chemokine protein family (Fernandez E J and Lolis E., Annu. Rev. Pharmacol. Toxicol., 202, 42, 469-99; Allen S J et al, Annu. Rev. Immunol., 2007, 25, 787-820, incorporated herein by reference).

Truncations within this N-terminal region can maintain binding to the receptor but can lead to a change or loss of function (for examples Zhang Y J et al, J. Biol. Chem., 1994, 269, 15918; Gong J-H and Clark-Lewis I., J. Exp. Med., 1995, 181, 631-640; Fernandez E J and Lolis E., Annu. Rev. Pharmacol. Toxicol., 202, 42, 469-99; Allen S J et al, Annu. Rev. Immunol., 2007, 25, 787-820, each of which is incorporated herein by reference).

Truncations at the C-terminus of the chemokine can also be made and maintain receptor binding activity (Treating Inflammatory Disorders, Ola Winqvist and Graham Cotton, WO2010/029317, incorporated herein by reference in its entirety).

In other embodiments, fragments and variants of chemokines are used in the devices and methods as disclosed herein. More particularly, such fragments and variants retain the ability to specifically bind to their cognate chemokine receptor. Chemokines are known by those skilled in the art to share specific receptor binding domains, including a similar monomeric fold, characterized, for example, by a disordered amino-terminal domain, followed by a conserved core region, consisting of the so called "N-loop," three antiparallel β-strands, and a carboxyl-terminal α-helix. While not being bound by theory, it is believed that the chemokine-chemokine receptor interaction is a two-step mechanism, in which the core of the chemokine interacts first with a binding site formed by the extracellular domains of the receptor, while another interaction is formed between the chemokine N terminus and a second binding site on the receptor in order to trigger receptor activation. Thus, a "fragment," such as a functional fragment of a chemokine is intended to mean a portion of the amino acid sequence of the protein that retains binding for its cognate receptor. The fragment may include, for example, the monomeric fold region, or portions thereof such as the amino-terminal domain, the conserved core region and/or the "N-loop," the anti-parallel β-strands, and/or the carboxyl-terminal α-helix or combinations and portions thereof.

Further, it is recognized that a polypeptide can be considerably mutated without materially altering one or more of the polypeptide's functions, for example, without altering specific binding and/or the folding of the protein. The genetic code is well known to be degenerate, and thus different codons encode the same amino acids. Even where an amino acid substitution is introduced, the mutation can be conservative and have no material impact on the essential functions of a protein (see for example, Stryer, Biochemistry 4th Ed., W. Freeman & Co., New York, N.Y., 1995). This includes, for example, the ability of the protein to bind and interact with other proteins, such as a truncated chemokine binding to its cognate receptor.

In some examples, part of a polypeptide chain can be deleted without impairing or eliminating all of its functions. For example, the deletion of between about 1 and about 20 amino acids on the C- and/or N-terminus, such as deletions of about 1, 2, 3, 4, 5, 6, 7, 8, 9, 10, 11, 12, 13, 14, 15, 16, 17, 18, 19, or 20 amino acids at the C- and/or N-terminus, can result in a chemokine that retains function, such as specific binding of its cognate receptor. Such truncations can retain the full function of an entire protein, and/or can allow for retained functions such as protein-protein interactions as in the case of ligand-receptor interactions. Chemokines having deletions of a small number of amino acids, for example, less than about 20% (such as less than about 18%, less than about 15%, less than about 10%, less than about 8%, less than about 5%, less than about 2%, or less than about 1%) of the total number of amino acids in the wild type chemokine can also be used in the methods and devices disclosed herein. Moreover, insertions or additions can be made in the polypeptide chain for example, adding epitope tags, without impairing or eliminating its functions (Ausubel et al., Current Protocols in Molecular Biology, Greene Publ. Assoc. and Wiley-Intersciences, 1998). Other modifications that can be made without materially impairing one or more functions of a polypeptide include, for example, in vivo or in vitro chemical and biochemical modifications or the incorporation of unusual amino acids. In some examples, a functional fragment of a chemokine may consist of about 10 or more, about 25 or more, about 50 or more, about 75 or more, about 100 or more, about 125 or more, about 150, about 175 or more, or about more or 200 or more amino acid residues of a chemokine amino acid sequence.

In some examples, the chemokine or a functional fragment thereof has an amino acid that has at least about 60% or 65% sequence identity, about 70% or 75% sequence identity, about 80% or 85% sequence identity, about 90%, 91%, 92%, 93%, 94%, 95%, 96%, 97%, 98% or 99% sequence identity over its full length as compared to a reference sequence, such as those detailed herein, for example using the NCBI Blast 2.0 gapped BLAST set to default parameters. Alignment may also be performed manually by inspection. One or more conservative amino acid modifications can also be made in the chemokine amino acid sequence, whether an addition, deletion or modification, that does not substantially alter the 3-dimensional structure of the polypeptide or its ability to bind to the cognate receptor. For example, a conservative amino acid substitution does not affect the ability of the chemokine to specifically bind its cognate receptor. Conservative substitution tables providing functionally similar amino acids are well known in the art. The following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

Peptides, such as chemokines and fragments thereof, can be modified by a variety of chemical techniques to produce derivatives having essentially the same activity or function—such as binding to a cognate receptor—as the unmodified peptides, and optionally having other desirable properties. For example, carboxylic acid groups of the protein, whether carboxyl-terminal or side chain, may be provided in the form of a salt of a pharmaceutically-acceptable cation or esterified to form a C1-C16 ester, or converted to an amide of formula NR1R2 wherein R1 and R2 are each independently H or C1-C16 alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to C1-C16 alkyl or dialkyl amino or further converted to an amide.

Hydroxyl groups of the peptide side chains can be converted to C1-C16 alkoxy or to a C1-C16 ester using well-recognized techniques. Phenyl and phenolic rings of the peptide side chains can be substituted with one or more halogen atoms, such as F, Cl, Br or I, or with C1-C16 alkyl, C1-C16 alkoxy, carboxylic acids and esters thereof, or amides of such carboxylic acids. Methylene groups of the peptide side chains can be extended to homologous C2-C4 alkylenes. Thiols can be protected with any one of a number of well-recognized protecting groups, such as acetamide groups. Those skilled in the art will also recognize methods for introducing cyclic structures into the peptides of this disclosure to select and provide conformational constraints to the structure that result in enhanced stability. For example, a C- or N-terminal cysteine can be added to the peptide, so that when oxidized the peptide will contain a disulfide bond, generating a cyclic peptide. Other peptide cyclizing methods include the formation of thioethers and carboxyl- and amino-terminal amides and esters.

Peptidomimetic and organomimetic embodiments are also within the scope of the present disclosure, whereby the three-dimensional arrangement of the chemical constituents of such peptido- and organomimetics mimic the three-dimensional arrangement of the peptide backbone and component amino acid side chains, resulting in such peptido- and organomimetics of the proteins of this disclosure. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs", in Klegerman & Groves, eds., 1993, Pharmaceutical Biotechnology, Interpharm Press: Buffalo Grove, Ill., pp. 165 174 and Principles of Pharmacology Munson (ed.) 1995, Ch. 102, for descriptions of techniques used in CADD. Also included within the scope of the disclosure are mimetics prepared using such techniques.

Amino acids in a peptide, polypeptide, or protein generally are chemically bound together via amide linkages (CONN). Additionally, amino acids may be bound together by other chemical bonds. For example, linkages for amino acids or amino acid analogs can include CH2NH—, —CH2S—, —CH2-CH2-, —CH═CH— (cis and trans), —COCH2-, —CH(OH)CH2-, and —CHH2SO— (These and others can be found in Spatola, in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci pp. 463-468, 1980; Hudson, et al., Int J Pept Prot Res 14:177-185, 1979; Spatola et al. Life Sci 38:1243-1249, 1986; Harm J. Chem. Soc Perkin Trans. 1307-314, 1982; Almquist et al. J. Med. Chem. 23:1392-1398, 1980; Jennings-White et al. Tetrahedron Lett 23:2533, 1982; Holladay et al. Tetrahedron. Lett 24:4401-4404, 1983; and Hruby Life Sci 31:189-199, 1982.

CCL20 is the gene symbol approved by the HUGO Gene Nomenclature Committee for chemokine (C-C motif) ligand 20, also known as MIP-3alpha. The HGNC ID for this gene is 10619. The gene is located at chromosome position 2q33-q37. The previous symbol and name for the gene is SCYA20, "small inducible cytokine subfamily A (Cys-Cys), member 20". Synonyms for this gene include CKb4, exo-dus-1, LARC, MIP-3a, ST38. The Genbank reference sequence for CCL20 is D86955.1 as available on 13 Jun. 2011, which is incorporated herein by reference in its entirety.

CCL19 is the gene symbol approved by the HUGO Gene Nomenclature Committee for chemokine (C-C motif) ligand 19, also known as MIP-3b. The HGNC ID for this gene is 10617. The gene is located at chromosome position 9p13. The previous symbol and name for the gene is SCYA19, "small inducible cytokine subfamily A (Cys-Cys), member 19". Synonyms for this gene include "beta chemokine exodus-3", "CC chemokine ligand 19", "CK beta-11", CKb11, "EB11-ligand chemokine", ELC, exodus-3, "macrophage inflammatory protein 3-beta", MIP-3b. The Genbank reference sequence for CCL19 is AB000887.1 as available on 13 Jun. 2011, which is incorporated herein by reference in its entirety.

CCL21 is the gene symbol approved by the HUGO Gene Nomenclature Committee for chemokine (C-C motif) ligand 21. The HGNC ID for this gene is 10620. The gene is located at chromosome position 9p13. The previous symbol and name for the gene is SCYA21, "small inducible cytokine subfamily A (Cys-Cys), member 21". Synonyms for this gene include 6Ckine, "beta chemokine exodus-2", CKb9, ECL, "Efficient Chemoattractant for Lymphocytes", exodus-2, "secondary lymphoid tissue chemokine", SLC, TCA4. The Genbank reference sequence for CCL21 is AB002409.1 as available on 13 Jun. 2011, which is incorporated herein by reference in its entirety.

CCL1 is the gene symbol approved by the HUGO Gene Nomenclature Committee for chemokine (C-C motif) ligand 1. The HGNC ID for this gene is 10609. The gene is located at chromosome position 17q11.2. The previous symbol and name for the gene is SCYA1, "small inducible cytokine A1 (1-309, homologous to mouse Tca-3)". Synonyms for this gene include 1-309, "inflammatory cytokine 1-309", P500, SISe, "T lymphocyte-secreted protein I-309", TCA3. The Genbank reference sequence for CCL1 is M57506.1 as available on 13 Jun. 2011, which is incorporated herein by reference in its entirety.

CXCL11 is the gene symbol approved by the HUGO Gene Nomenclature Committee for chemokine (C-X-C motif) ligand 11. The HGNC ID for this gene is 10638. The gene is located at chromosome position 4q21. The previous symbol and name for the gene is SCYB9B, SCYB11, "small inducible cytokine subfamily B (Cys-X-Cys), member 11". Synonyms for this gene include b-R1, H174, I-TAC, IP-9. The Genbank reference sequence for CXCL11 is U66096.1 as available on 13 Jun. 2011, which is incorporated herein by reference in its entirety.

CXCL12 is the gene symbol approved by the HUGO Gene Nomenclature Committee for chemokine (C-X-C motif) ligand 12. The HGNC ID for this gene is 10672. The gene is located at chromosome position 10q11.1. The previous symbol and name for the gene is SDF1, SDF1A, SDF1B, "stromal cell-derived factor 1". Synonyms for this gene include PBSF, SCYB12, SDF-1a, SDF-1b, TLSF-a, TLSF-b, TPAR1. The Genbank reference sequence for CXCL12 is L36033.1 as available on 13 Jun. 2011, which is incorporated herein by reference in its entirety.

SELE is the gene symbol approved by the HUGO Gene Nomenclature Committee for selectin E, also known as ELAM-1. The HGNC ID for this gene is 10718. The gene is located at chromosome position 1q22-q25. Synonyms for this gene include CD26E, ESEL.

The Genbank reference sequence for SELE is M30640.1 as available on 13 Jun. 2011, which is incorporated herein by reference in its entirety.

CCL17 is the gene symbol approved by the HUGO Gene Nomenclature Committee for chemokine (C-C motif) ligand 17. The HGNC ID for this gene is 10615. The gene is located at chromosome position 16q13. The previous symbol and name for the gene is SCYA17, "small inducible cytokine subfamily A (Cys-Cys), member 17". Synonyms for this gene include ABCD-2, TARC. The Genbank reference sequence for CCL17 is D43767.1 as available on 4 Apr. 2012, which is incorporated herein by reference in its entirety.

CCL22 is the gene symbol approved by the HUGO Gene Nomenclature Committee for chemokine (C-C motif) ligand 22. The HGNC ID for this gene is 10621. The gene is located at chromosome position 16q13. The previous symbol and name for the gene is SCYA22, "small inducible cytokine subfamily A (Cys-Cys), member 22". Synonyms for this gene include A-152E5.1, ABCD-1, DC/B-CK, MDC, MGC34554, STCP-1. The Genbank reference sequence for CCL22 is U83171.1 as available on 4 Apr. 2012, which is incorporated herein by reference in its entirety.

CCL25 is the gene symbol approved by the HUGO Gene Nomenclature Committee for chemokine (C-C motif) ligand 25. The HGNC ID for this gene is 10624. The gene is located at chromosome position 19p13.2. The previous symbol and name for the gene is SCYA25, "small inducible cytokine subfamily A (Cys-Cys), member 25". Synonyms for this gene include "Ck beta-15", Ckb15, TECK, "TECKvar", "thymus expressed chemokine". The Genbank reference sequence for CCL25 is U86358.1 as available on 13 Jun. 2011, which is incorporated herein by reference in its entirety.

CCL27 is the gene symbol approved by the HUGO Gene Nomenclature Committee for chemokine (C-C motif) ligand 27. The HGNC ID for this gene is 10626. The previous symbol and name for the gene is SCYA27, "small inducible cytokine subfamily A (Cys-Cys), member 27". The gene is located at chromosome position 9p13. Synonyms for this gene include ALP, "CC chemokine ILC", CTACK, CTAK, "cutaneous T-cell attracting chemokine", ESkine, "IL-11 Ralpha-locus chemokine", ILC, PESKY, skinkine. The Genbank reference sequence for CCL27 is AJ2433542.1 as available on 29 May 2012, which is incorporated herein by reference in its entirety.

CCL28 is the gene symbol approved by the HUGO Gene Nomenclature Committee for chemokine (C-C motif) ligand 28, also known as MEC and CCK1. The HGNC ID for this gene is 17700. The gene is located at chromosome position 5p12. Synonyms for this gene include "CC chemokine CCL28", CCK1, MEC, "mucosae-associated epithelial chemokine", SCYA28, "small inducible cytokine A28", "small inducible cytokine subfamily A (Cys-Cys), member 28". The Genbank reference sequence for CCL28 is AF110384.1 as available on 13 Jun. 2011, which is incorporated herein by reference in its entirety.

CXCL9 is the gene symbol approved by the HUGO Gene Nomenclature Committee for chemokine (C-X-C motif) ligand 9. The HGNC ID for this gene is 7098. The gene is located at chromosome position 4q21. The previous symbol and name for the gene is CMK, MIG, "monokine induced by gamma interferon". Synonyms for this gene include crg-10, Humig, SCYB9. The Genbank reference sequence for CXCL10 is X72755.1 as available on 13 Jun. 2011, which is incorporated herein by reference in its entirety.

CXCL10 is the gene symbol approved by the HUGO Gene Nomenclature Committee for chemokine (C-X-C motif) ligand 10. The HGNC ID for this gene is 10637. The gene is located at chromosome position 4q21. The previous symbol and name for the gene is INP10, SCYB10, "small inducible cytokine subfamily B (Cys-X-Cys), member 10". Synonyms for this gene include C7, crg-2, gIP-10, IF110, IP-10, mob-1. The Genbank reference sequence for CXCL10 is X02530.1 as available on 13 Jun. 2011, which is incorporated herein by reference in its entirety.

CXCL13 is the gene symbol approved by the HUGO Gene Nomenclature Committee for chemokine (C-X-C motif) ligand 13. The HGNC ID for this gene is 10639. The gene is located at chromosome position 4q21. The previous symbol and name for the gene is SCYB13, "small inducible cytokine B subfamily (Cys-X-Cys motif), member 13 (B-cell chemoattractant)". Synonyms for this gene include ANGIE, ANGIE2, "B-cell chemoattractant", BCA-1, BLC, BLR1L. The Genbank reference sequence for CXCL13 is AJ002211.1 as available on 29 May 2012, which is incorporated herein by reference in its entirety.

An example of a chemokine of the various embodiments of the invention containing modifications and specifically adapted for use in the invention is described in detail herein (see Example 3 below). The modified CCL8 (MCP-2) corresponds to residues 1 to 76 of the full length mature protein (and lacks the N-terminal signal peptide of 23 amino acids, which is cleaved off) and thus retains the chemokine fold. The Gln at the N-terminus of the protein is subject to pyroGlu formation under physiological conditions. Thus Gln1 of the sequence is substituted with pyroglutamine to prevent mixed species of N-terminal Gln and pyroGlu being generated (SEQ ID NO: 1). This improves the yield of synthesis and ensures a homogeneous chemokine preparation through column manufacture and use. FmocLys (ivDde)-OH is incorporated as residue 75 to facilitate site-specific labelling at this position of the protein (SEQ ID NO: 2). The naturally occurring lysine at position 75 is modified through biotinylation. A PEG spacer may be incorporated between the ε-amino functionality and the biotin (SEQ ID NO: 3).

Thus, in certain embodiments the invention also relates to a modified chemokine comprising, consisting essentially of or consisting of the amino acid sequence of SEQ ID NO: 1:

XPDSVSIPITCCFNVINRKIPIQRLESYTRITNIQCPKEAVIFKTKRGKE

VCADPKERWVRDSMKHLDQIFQNLXP

X1=pyroGlu (but may remain as Gln in some embodiments)

X75=an amino acid residue that can be biotinylated, such as lysine, ornithine or diaminopropionic acid and optionally is biotinylated, optionally via a spacer molecule such as PEG, e.g. K(PEG-Biotin).

Or SEQ ID NO: 3

XPDSVSIPITCCFNVINRKIPIQRLESYTRITNIQCPKEAVIFKTKRGKE

VCADPKERWVRDSMKHLDQIFQNLXP

X1=pyroGlu (but may remain as Gln in some embodiments)

X75=K(PEG-Biotin).

A further example of a chemokine of the various embodiments of the invention containing modifications and specifically adapted for use in the invention is described in detail herein (see Example 4 below). The modified CCL5 (RANTES) corresponds to residues 1 to 68 of the full length mature protein (and lacks the N-terminal signal peptide of 23 amino acids, which is cleaved off) and thus retains the chemokine fold. The single methionine (Met67) within the sequence is mutated to lysine, to mitigate against oxidation of this residue during the chain assembly (SEQ ID NO: 4). This Met to Lys substitution provides a lysine at position 67 which can be modified through biotinylation. FmocLys (ivDde)-OH is incorporated as residue 67 to facilitate site-specific labelling at this position of the protein (SEQ ID NO: 5). The biotinylated version comprises, consists essentially of or consists of the amino acid sequence of SEQ ID NO: 6.

Thus, in certain embodiments the invention also relates to a modified chemokine comprising, consisting essentially of or consisting of the amino acid sequence of SEQ ID NO: 6:

SPYSSDTTPCCFAYIARPLPRAHIKEYFYTSGKCSNPAVVFVTRKNRQVC

ANPEKKWVREYINSLEXS

X is an amino acid residue that can be biotinylated, such as lysine, ornithine or diaminopropionic acid and optionally is biotinylated, optionally via a spacer molecule such as PEG (e.g. K(Biotin))

A further example of a chemokine of the various embodiments of the invention containing modifications and specifically adapted for use in the invention is described in detail herein (see Example 5 below). The modified CCL20 (MIP-3α) corresponds to residues 1 to 70 of the full length mature protein (and lacks the N-terminal signal peptide of 26 amino acids, which is cleaved off) and thus retains the chemokine fold (SEQ ID NO: 7). FmocLys(ivDde)-OH is incorporated as residue 68 to facilitate site-specific labelling at this position of the protein (SEQ ID NO: 8). The naturally occurring lysine at position 68 is modified through biotinylation. A PEG spacer may be incorporated between the ε-amino functionality and the biotin. The final protein may thus comprise, consist essentially of or consist of the amino acid sequence of SEQ ID NO: 9.

Thus, in certain embodiments the invention also relates to a modified chemokine comprising, consisting essentially of or consisting of the amino acid sequence of SEQ ID NO: 9:

ASNFDCCLGYTDRILHPKFIVGFTRQLANEGCDINAIIFHTKKKLSVCAN

PKQTWVKYIVRLLSKKVXNM

X is an amino acid residue that can be biotinylated, such as lysine, ornithine or diaminopropionic acid and optionally is biotinylated, optionally via a spacer molecule such as PEG, in particular K(PEG-Biotin)

A further example of a chemokine of the various embodiments of the invention containing truncation and modifications and specifically adapted for use in the invention is described in detail herein (see Example 6 below). The truncated CXCL12 (SDF-1α) corresponds to residues 1 to 67 of the full length mature protein (and lacks the N-terminal signal peptide of 21 amino acids, which is cleaved off from an immature protein of total length 93 amino acids) and thus retains the chemokine fold (SEQ ID NO: 10). FmocLys (ivDde)-OH is incorporated as residue 64 to facilitate site-specific labelling at this position of the protein (SEQ ID NO: 11). The naturally occurring lysine at position 64 is modified through biotinylation. The final protein may thus comprise, consist essentially of or consist of the amino acid sequence of SEQ ID NO: 12.

Thus, in certain embodiments the invention also relates to a truncated/modified chemokine comprising, consisting essentially of or consisting of the amino acid sequence of SEQ ID NO: 12:

KPVSLSYRCPCRFFESHVARANVKHLKILNTPNCALQIVARLKNNNRQVC

IDPKLKWIQEYLEXALN

X is an amino acid residue that can be biotinylated, such as lysine, ornithine or diaminopropionic acid and optionally is biotinylated, optionally via a spacer molecule such as PEG, especially K(Biotin)

Or SEQ ID NO: 10:

KPVSLSYRCPCRFFESHVARANVKHLKILNTPNCALQIVARLKNNNRQVC

IDPKLKWIQEYLEKALN

A further example of a chemokine of the various embodiments of the invention containing modifications and specifically adapted for use in the invention is described in detail herein (see Example 7 below). The modified CCL22 (MDC) corresponds to residues 1 to 69 of the full length mature protein (and lacks the N-terminal signal peptide of 24 amino acids, which is cleaved off) and thus retains the chemokine fold (SEQ ID NO: 13). FmocLys(ivDde)-OH is incorporated as residue 66 to facilitate site-specific labelling at this position of the protein (SEQ ID NO: 14). The naturally occurring lysine at position 66 is modified through biotinylation. A PEG spacer may be incorporated between the ε-amino functionality and the biotin. The final protein may thus comprise, consist essentially of or consist of the amino acid sequence of SEQ ID NO: 15.

Thus, in certain embodimentsin certain embodiments the invention also relates to a modified chemokine comprising, consisting essentially of or consisting of the amino acid sequence of SEQ ID NO: 15:

GPYGANMEDSVCCRDYVRYRLPLRVVKHFYWTSDSCPRPGVVLLTFRDKE

ICADPRVPWVKMILNXLSQ

X is an amino acid residue that can be biotinylated, such as lysine, ornithine or diaminopropionic acid and optionally is biotinylated, optionally via a spacer molecule such as PEG, especially K(PEG-Biotin)

A further example of a chemokine of the various embodiments of the invention containing modifications and specifically adapted for use in the invention is described in detail herein (see Example 8 below). The modified CCL17 (TARC) corresponds to residues 1 to 71 of the full length mature protein (and lacks the N-terminal signal peptide of 23 amino acids, which is cleaved off) and thus retains the chemokine fold. An additional lysine or equivalent residue may be inserted at the C-terminus, at position 72. The chemokine may thus comprise, consist essentially of or consist of the amino acid sequence of SEQ ID NO: 16. FmocLys(ivDde)-OH is incorporated as residue 72 to facilitate site-specific labelling at this position of the protein (SEQ ID NO: 17). The ε-amino side chain functionality of Lys(72) is modified through biotinylation. A PEG spacer may be incorporated between the ε-amino functionality and the biotin. The final protein may thus comprise, consist essentially of or consist of the amino acid sequence of SEQ ID NO: 18.

Thus, in certain embodiments the invention also relates to a modified chemokine comprising, consisting essentially of or consisting of the amino acid sequence of SEQ ID NO: 16 or 18:

SEQ ID NO: 16
ARGTNVGRECCLEYFKGAIPLRKLKTWYQTSEDCSRDAIVFVTVQGRAIC

SDPNNKRVKNAVKYLQSLERSX

X is an amino acid residue that can be biotinylated, such as lysine, ornithine or diaminopropionic acid and optionally is biotinylated (e.g. K-biotin), optionally via a spacer molecule such as PEG, in particular K(PEG-Biotin)

SEQ ID NO: 18
ARGTNVGRECCLEYFKGAIPLRKLKTWYQTSEDCSRDAIVFVTVQGRAIC

SDPNNKRVKNAVKYLQSLERSK(PEG-Biotin)

A further example of a chemokine of the various embodiments of the invention containing modifications and specifically adapted for use in the invention is described in detail herein (see Example 9 below). The modified CCL19 (MIP-3β) corresponds to residues 1 to 77 of the full length mature protein (and lacks the N-terminal signal peptide of 21 amino acids, which is cleaved off) and thus retains the chemokine fold. An additional lysine is inserted at the C-terminus, at position 78. The chemokine may thus comprise, consist essentially of or consist of the amino acid sequence of SEQ ID NO: 19. FmocLys(ivDde)-OH is incorporated as residue 78 to facilitate site-specific labelling at this position of the protein (SEQ ID NO: 20). The ε-amino side chain functionality of Lys(78) is modified through biotinylation. The final protein may thus comprise, consist essentially of or consist of the amino acid sequence of SEQ ID NO: 21.

Thus, in certain embodiments the invention also relates to a modified chemokine comprising, consisting essentially of or consisting of the amino acid sequence of SEQ ID NO: 19 or 21:

SEQ ID NO: 19
GTNDAEDCCLSVTQKPIPGYIVRNFHYLLIKDGCRVPAVVFTTLRGRQLC

APPDQPWVERIIQRLQRTSAKMKRRSSX

X is an amino acid residue that can be biotinylated, such as lysine, ornithine or diaminopropionic acid and optionally is biotinylated (e.g. K-biotin), optionally via a spacer molecule such as PEG, in particular K(PEG-Biotin)

SEQ ID NO: 21
GTNDAEDCCLSVTQKPIPGYIVRNFHYLLIKDGCRVPAVVFTTLRGRQL

CAPPDQPWVERIIQRLQRTSAKMKRRSSX

X is K(Biotin)

A further example of a chemokine of the various embodiments of the invention containing modifications and specifically adapted for use in the invention is described in detail herein (see Example 10 below). The modified CXCL11 (ITAC) corresponds to residues 1 to 73 of the full length mature protein (and lacks the N-terminal signal peptide of 21 amino acids, which is cleaved off) and thus retains the chemokine fold (SEQ ID NO: 22). An additional lysine is inserted at the C-terminus, optionally via a PEG spacer, at position 74. The chemokine may thus comprise, consist essentially of or consist of the amino acid sequence of SEQ ID NO: 23.

SEQ ID NO: 23:
FPMFKRGRCLCIGPGVKAVKVADIEKASIMYPSNNCDKIEVIITLKENK

GQRCLNPKSKQARLIIKKVERKNFX

X is an amino acid residue that can be biotinylated, such as lysine, ornithine or diaminopropionic acid and optionally is biotinylated, optionally via a spacer molecule such as PEG. The amino acid residue may be added via a spacer molecule such as PEG and may thus be "PEG-K".

FmocLys(ivDde)-OH is incorporated, following Fmoc-12-amino-4,7,10-trioxadodecanoic acid, as residue 74 to facilitate site-specific labelling at this position of the protein (SEQ ID NO: 24). The ε-amino side chain functionality of the additional Lys(74) is modified through biotinylation. The final protein may thus comprise, consist essentially of or consist of the amino acid sequence of SEQ ID NO: 25.

SEQ ID NO: 25:
FPMFKRGRCLCIGPGVKAVKVADIEKASIMYPSNNCDKIEVIITLKENK

GQRCLNPKSKQARLIIKKVERKNFX

X is PEG-K(biotin).

Thus, in certain embodiments the invention also relates to a modified chemokine comprising, consisting essentially of or consisting of the amino acid sequence of SEQ ID NO: 23 or 25.

A further example of a chemokine of the various embodiments of the invention containing truncation and modifications and specifically adapted for use in the invention is described in detail herein (see Example 11 below). The truncated form of human CCL25 (TECK) corresponds to residues 1-74 of the mature protein, which encompasses the sequence corresponding to the chemokine fold. The full length mature protein is 127 amino acids (the signal peptide is 23 amino acids in a 150 amino acid immature protein). The single methionine within the sequence is altered to Norleucine, to mitigate against oxidation of this residue during the chain assembly, which was observed during the synthesis of the natural sequence derivative. The Gln at the N-terminus of the proteins is subject to pyroGlu formation under physiological conditions. Thus Gln1 of the sequence was substituted with pyroglutamine to prevent mixed species of N-terminal Gln and pyroGlu being generated. This improves the yield of synthesis and ensures a homogeneous chemokine preparation through column manufacture and use. The naturally occurring lysine at position 72 was modified through biotinylation on the resin. A PEG spacer was incorporated between the ε-amino functionality and the biotin.

Thus, in certain embodiments the invention also relates to a modified chemokine comprising, consisting essentially of or consisting of the amino acid sequence of SEQ ID NO: 26:

XGVFEDCCLAYHYPIGWAVLRRAWTYRIQEVSGSCNLPAAIFYLPKRHRK

VCGNPKSREVQRAXKLLDARNXVF

X1=pyroGlu or Gln
X64=Norleucine
X72=an amino acid residue that can be biotinylated, such as lysine, ornithine or diaminopropionic acid and optionally is biotinylated, optionally via a spacer molecule such as PEG, e.g. K(PEG-Biotin)

XGVFEDCCLAYHYPIGWAVLRRAWTYRIQEVSGSCNLPAAIFYLPKRHRK

VCGNPKSREVQRAXKLLDARNXVF

X1=pyroGlu or Gln
X64=Norleucine
X72=K(ivDde)

FmocLys(ivDde)-OH may be incorporated as residue 72 to facilitate site-specific labelling at this position of the protein (SEQ ID NO: 27). Subsequent removal of the ivDde protecting group, followed by coupling of the PEG spacer and Biotin, may be carried out as described in the general protocol section. The desired active chemokine may thus comprise, consist essentially of or consist of the amino acid sequence of SEQ ID NO: 28:

XGVFEDCCLAYHYPIGWAVLRRAWTYRIQEVSGSCNLPAAIFYLPKRHRK

VCGNPKSREVQRAXKLLDARNXVF

X1=pyroGlu or Gln
X64=Norleucine
X72 is K(PEG-Biotin)

A further example of a chemokine of the various embodiments of the invention containing modifications and specifically adapted for use in the invention is described in detail herein (see Example 12 below). Human CCL27 (CTAC) corresponding to residues 1-88, is initially expressed as 112 amino acids comprising the chemokine fold, and a 24 amino acid signal peptide which is cleaved off. The Met(87) within the sequence was mutated to lysine to provide a lysine at position 87 which was modified through biotinylation on the resin. A PEG spacer was incorporated between the ε-amino functionality and the biotin.

Thus, in certain embodiments the invention also relates to a modified chemokine comprising, consisting essentially of or consisting of the amino acid sequence of SEQ ID NO: 29:

FLLPPSTACCTQLYRKPLSDKLLRKVIQVELQEADGDCHLQAFVLHLAQR

SICIHPQNPSLSQWFEHQERKLHGTLPKLNFGMLRKXG

X is an amino acid residue that can be biotinylated, such as lysine, ornithine or diaminopropionic acid and optionally is biotinylated, optionally via a spacer molecule such as PEG, e.g. K(PEG-Biotin)

FLLPPSTACCTQLYRKPLSDKLLRKVIQVELQEADGDCHLQAFVLHLAQR

SICIHPQNPSLSQWFEHQERKLHGTLPKLNFGMLRKXG

X=K(ivDde)

FmocLys(ivDde)-OH is incorporated as residue 87 to facilitate site-specific labelling at this position of the protein (SEQ ID NO: 30). Subsequent removal of the ivDde protecting group, followed by coupling of the PEG spacer and Biotin, was carried out as described in the general protocol section. The desired active chemokine may thus comprise, consist essentially of or consist of the amino acid sequence of SEQ ID NO: 31:

FLLPPSTACCTQLYRKPLSDKLLRKVIQVELQEADGDCHLQAFVLHLAQR

SICIHPQNPSLSQWFEHQERKLHGTLPKLNFGMLRKXG

X=K(PEG-Biotin)

A further example of a chemokine of the various embodiments of the invention containing modifications and specifically adapted for use in the invention is described in detail herein (see Example 13 below). The modified CXCL10 (IP-10) corresponds to residues 1 to 78 of the full length mature protein (and lacks the N-terminal signal peptide of 21 amino acids, which is cleaved off) and thus retains the chemokine fold. An amino acid which is capable of biotinylation, such as lysine or ornithine for example, may be inserted as residue 78. Insertion may be via a spacer, such as a PEG spacer. The linear amino acid sequence (SEQ ID NO: 32) is shown, prior to attachment of the PEG spacer, additional lysine and biotin molecules:

VPLSRTVRCTCISISNQPVNPRSLEKLEIIPASQFCPRVEIIATMKKKG

EKRCLNPESKAIKNLLKAVSKERSKRSP

Thus, position 78 may be modified through biotinylation. FmocLys(ivDde)-OH may be incorporated as residue 78 to facilitate site-specific labelling at this position of the protein (SEQ ID NO: 33). A suitable spacer, such as a PEG spacer, may be incorporated between the ε-amino functionality and the biotin. The biotinylated version comprises, consists essentially of or consists of the amino acid sequence of SEQ ID NO: 34.

Thus, in certain embodiments the invention also relates to a modified chemokine comprising, consisting essentially of or consisting of the amino acid sequence of SEQ ID NO: 34:

VPLSRTVRCTCISISNQPVNPRSLEKLEIIPASQFCPRVEIIATMKKKG

EKRCLNPESKAIKNLLKAVSKERSKRSPX

X is an amino acid residue that can be biotinylated, such as lysine, ornithine or diaminopropionic acid and optionally is biotinylated, optionally via a spacer molecule such as PEG, e.g. K(PEG-Biotin) and may be attached via a spacer molecule, e.g. PEG-K(Biotin)

The specific chemokines, including derivatives thereof as described herein, newly synthesised for use in the methods of the various embodiments of the invention may in certain embodimentsin certain embodiments represent separate aspects of the invention. Biotinylation is positioned so as to permit immobilisation whilst retaining receptor binding capability.

Chemokines useful in the various embodiments of the invention may be synthesised through any suitable means known in the art. Preferably, the chemokines are chemically synthesised as this facilitates modification and labelling etc. However, recombinant DNA based approaches may also be employed in combination with appropriate labelling and modification technologies as required. Thus, in certain embodiments the invention also provides a nucleic acid molecule encoding the chemokines of the various embodiments of the invention. In other embodiments the invention also relates to a vector containing such a nucleic acid molecule and a host cell containing the vector. The vector may additionally comprise a suitable promoter operably linked to the nucleic acid molecule, to facilitate transcription of the corresponding mRNA molecule. The host cell may be capable of expressing the protein by transcription and translation of the nucleic acid molecule encoding a chemokine of the various embodiments of the invention.

The chemokines useful in the various embodiments of the invention can be biotinylated by methods known in the art such as described in WO 00/50088 A2, which is incorporated herein by reference in its entirety. As indicated above, site-specific labelling of the chemokines of the various embodiments of the invention is preferable, although any labelling technique which does not significantly affect the receptor-binding capacity of the chemokine may be employed. Various site-specifically biotinylated chemokines and native chemokines are available commercially, for instance from Almac, Craigavon, UK. In specific embodiments the one or more chemokines are biotinylated via a spacer group. The spacer may be employed to prevent the biotin group from impacting on the activity of the chemokine, in particular binding of the chemokine to its cognate receptor. Any suitable spacer that facilitates retention of receptor binding properties of the chemokine may be employed in the various embodiments of the invention. Thus, in the specific embodiments described above, spacers other than PEG spacers may be employed as appropriate. In specific embodiments, the spacer is a polyethylene glycol (PEG) spacer. PEG has been shown to be an effective spacer permitting attachment of biotin to the chemokine (which can then be immobilized on the solid support through interaction with streptavidin) without compromising receptor binding capability.

In the context of the various embodiments of the present invention the term "antibody" includes all immunoglobulins or immunoglobulin-like molecules with specific binding affinity for the relevant chemokine receptor (including by way of example and without limitation, IgA, IgD, IgE, IgG and IgM, combinations thereof, and similar molecules produced during an immune response in any vertebrate, for example, in mammals such as humans, goats, rabbits and mice). Specific immunoglobulins useful in the various embodiments of the invention include IgG isotypes. The antibodies useful in the various embodiments of the invention may be monoclonal or polyclonal in origin, but are typically monoclonal antibodies. Antibodies may be human antibodies, non-human antibodies, humanized versions of non-human antibodies, or chimeric antibodies. Various techniques for antibody humanization are well established and any suitable technique may be employed. The term "antibody" also refers to a polypeptide ligand comprising at least a light chain or heavy chain immunoglobulin variable region which specifically recognizes and binds an epitope of an antigen, and it extends to all antibody derivatives and fragments that retain the ability to specifically bind to the relevant chemokine receptor. These derivative and fragments may include Fab fragments, F(ab')$_2$ fragments, Fv fragments, single chain antibodies, single domain antibodies, Fc fragments etc. The term antibody encompasses antibodies comprised of both heavy and light chains, but also heavy chain (only) antibodies. In specific embodiments, the antibodies may be engineered so as to be specific for more than one chemokine receptor, for example bi-specific to permit binding to two different chemokine receptors. Suitable commercially available antibodies which bind to the chemokine receptors of interest are listed in table 1 below. They may or may not be labelled. General reference may be made to "Antibodies a laboratory manual: By E Harlow and D Lane. pp 726. Cold Spring Harbor Laboratory. 1988", which reference is incorporated herein in its entirety.

TABLE 1

Commercially available fluorophore labelled antibodies against specific chemokine receptors

| Antibody | Fluorophore | Supplier |
|---|---|---|
| CCR5 | PE | Biolegend |
| CXCR7 | PE | Biolegend |
| CCR6 | PE | BD Biosciences |
| CCR4 | PerCP Cy5.5 | BD Biosciences |
| CCR7 | PerCP Cy5.5 | Biolegend |
| CCR6 | PerCP Cy5.5 | BD Biosciences |
| CXCR4 | APC | R&D Systems |
| CCR8 | APC | R&D Systems |

The chemokine receptor expressing cells may thus be targeted using alternative binding agents, such as antibodies or other chemical compounds, as defined herein, rather than the natural chemokine binding partner. This approach is a new approach to treating inflammatory conditions.

Thus, in certain embodiments the invention also provides an apheresis column loaded with a solid support comprising a binding reagent capable of specifically binding to a chemokine receptor immobilized directly or indirectly on the support to permit removal of a cell expressing the chemokine receptor from the peripheral blood of a patient/subject, wherein the binding reagent is not a chemokine. The binding reagent capable of specifically binding to the chemokine receptor may be an agonist or an antagonist of the chemokine receptor. In specific embodiments, the binding reagent capable of specifically binding to the chemokine receptor is selected from an antibody and a chemical compound.

In other embodiments the invention thus also provides a method for treating an inflammatory condition comprising applying peripheral blood from a patient/subject to an apheresis column as defined above (an apheresis column loaded with a solid support comprising a binding reagent capable of specifically binding to a chemokine receptor immobilized directly or indirectly on the support to permit removal of a cell expressing the chemokine receptor from the peripheral blood of a patient, wherein the binding reagent is not a chemokine) thus removing chemokine receptor expressing cells from the peripheral blood of the patient/subject. The method may comprise returning the blood depleted of the chemokine receptor expressing cells to the patient/subject.

Similarly, in other embodiments the invention provides a binding reagent capable of specifically binding to a chemokine receptor for use in the treatment of an inflammatory condition, wherein the binding reagent is immobilized on a solid support contained within an apheresis column as defined above (an apheresis column loaded with a solid support comprising a binding reagent capable of specifically binding to a chemokine receptor immobilized directly or indirectly on the support to permit removal of a cell expressing the chemokine receptor from the peripheral blood of a patient/subject, wherein the binding reagent is not a chemokine), to which is applied peripheral blood from a patient thus removing chemokine receptor expressing cells from the peripheral blood of the patient.

These aspects of the various embodiments of the invention may be integrated into the more focussed therapeutic aspects of the various embodiments of the invention (i.e. treating cancer and various aspects thereof) and thus the remainder of the disclosure, including all specific embodiments, applies mutatis mutandis.

Solid support materials for immobilizing the binding reagents of the various embodiments of the invention are known in the art. "Solid support" refers to, for example, materials having a rigid or semi-rigid surface or surfaces, and may take the form of beads, resins, gels, microspheres, or other geometric configurations. A useful support material is one that does not activate blood cells so as to make them coagulate or adhere to the support as peripheral whole blood is applied to the device. In certain embodiments, a support treated with an agent to provide it with anti-coagulation properties, in particular a heparinized support is employed. Alternatively, the blood of the patient may be treated with an anti-coagulant such as heparin prior to application to the support. Useful support materials comprise high molecular weight carbohydrates, in particular carbohydrates having a molecular weight of 100 kDa or more, such as agarose, in particulate form, optionally cross-linked, and cellulose. Other preferred support materials are polymers, such as carboxylated polystyrene, and glass. The support of the various embodiments of the invention may be provided in the form of particles or fibres. The support particles may have regular form, such as spheres or beads, or irregular form. They may be porous or non-porous. A preferred average particle size of the support is from 50 μm to 2 mm. In certain embodiments Sepharose™, a cross linked, beaded-form of agarose, is used as the column matrix. It is chosen for its optimal distribution capacity and can provide a large available area for affinity binding. Solid supports may be provided in the form of magnetic beads, with the specific binding reagent immobilized on the magnetic beads. Following capture of the (CCR5, CCR6, CCR7, CCR8, CXCR4, CXCR7, CCR4, CCR9, CCR10, CXCR3 and/or CXCR5; or CCR4, CCR8 or CLA where Tregs are specifically targeted) chemokine receptor and/or Treg receptor expressing cells from the blood, the beads can be removed from the blood with the aid of an appropriate magnetic separator.

Methods for immobilizing binding reagents on a solid support are known in the art. A binding reagent, such as a chemokine, antibody, peptide, nucleic acid or chemical compound, can be immobilized on the support in a direct or indirect manner. Immobilization can be by means of a suitable linker in some embodiments. A preferred method of indirect immobilization of a binding reagent, such as a chemokine, relies upon the interaction between biotin and avidin molecules. "Avidin" or "avidin molecule" refers to any type of protein that specifically binds biotin to the substantial exclusion of other (small) molecules that might be present in a biological sample. Examples of avidin include avidins that are naturally present in egg white, oilseed protein (e.g., soybean meal), and grain (e.g., corn/maize), and streptavidin, which is a protein of bacterial origin. Thus, biotinylation of the binding reagent and use of an avidin molecule such as streptavidin immobilized on the solid support allows reliable attachment of the binding reagent to the solid support according to methods known in the art. Specifically, such a method may comprise providing the binding reagent in biotinylated form, providing a solid support having streptavidin immobilized on its surface, contacting the support with an aqueous solution of the biotinylated binding reagent, and rinsing the support with an aqueous solvent. In addition, binding pair interactions, such as antibody-antigen interactions, may also be utilised for indirect immobilisation of binding reagent onto a support. In such embodiments the support may be derivatised with one member of a binding pair, such as an antibody or fragment or derivative thereof, as defined herein, which has known affinity for a particular peptide sequence or small molecule hapten. Incorporating the other member of the binding pair, such as an antigen, peptide sequence or the hapten onto or into the binding reagent facilitates immobilisation onto a solid support coated with the corresponding antibody or fragment or derivative thereof. Thus, the binding reagent may be modified to include the peptide sequence or hapten into the linear molecule or may be added as a side chain or label. Any suitable antibody-antigen pair may be employed. The antibody fragment or derivative may be any fragment or derivative that retains specific binding affinity for the appropriate antigen. Examples include Fab, F(ab')$_2$ fragments, scFV, VH domains, single domain antibodies (such as nanobodies), heavy chain antibodies and humanized version of non-human antibodies etc. Other high affinity interactions can be utilised for immobilisation of binding reagents, as long as the binding reagent can be synthesised or derivatised with one of the interacting partners and the solid support synthesised or derivatised with the other interacting partner without loss of binding activity (i.e. binding of the binding reagent to the appropriate chemokine receptor). Immobilization may occur via essentially the same interaction in reverse in some embodiments. Thus, the binding reagent which may be a chemokine for example, may be attached to an antibody as defined herein, and the solid support derivatised with the antigen. The chemokine may be produced as a fusion protein with the antibody.

Alternatively binding reagents, such as chemokines and antibodies, can be immobilised directly onto a solid support using bioconjugation techniques established in the field. For example direct immobilisation of proteins onto cyanogen bromide activated solid supports via amino functionalities within the primary sequence of the protein. Alternatively, sulphydryl functionalities within proteins can be used to directly immobilise the protein to alkyl halide derivatised supports or supports containing free thiol functionalities. In further embodiments, proteins containing α-thioester functionalities can be directly immobilised on supports containing 1,2 amino thiol moieties (eg N-terminal cysteine) using the native chemical ligation reaction. Alternatively proteins modified with ketones and aldehydes can be immobilised on solid supports derivatised with hydrazinyl, hydrazide and aminoxy functionalities using hydrazone/oxime bond forming ligation reactions (and vice versa). Alternatively 'Click' chemistry can be used to immobilise proteins onto solid supports, whereby the protein and the support are derivatised with the appropriate mutually reactive chemical functionalities (azides and alkynes). In other embodiments Staudinger ligation chemistry can be used to immobilise appropriately derivatised proteins onto the appropriately derivatised solid supports.

The solid support is contained within or carried by the apheresis column. Thus, by "loaded" is meant that the column carries or contains the solid support in a manner such that (peripheral) blood can flow through the column in contact with the solid support. Thus, the solid support provides a matrix within the column through which blood flows, in continuous fashion in certain embodiments. This permits cells expressing the specific chemokine receptor to be removed from the blood passing through the column, such that blood exiting the column is depleted of the specific chemokine receptor-expressing cells. In specific embodiments, the apheresis column is loaded with a support comprising streptavidin immobilized on the support and one or more biotinylated binding reagents, such as chemokines, bound to the streptavidin on the support. The solid support may be comprised of a high-molecular weight carbohydrate, optionally cross-linked, such as agarose.

As discussed above, the binding reagent is coupled to the solid support. The relative amounts of binding reagent may be controlled to ensure that coupling between the solid support and the binding reagent will be immediate, minimising the risk of binding reagent decoupling from the solid support. Thus, it may be ensured that there is a relative excess of immobilization sites for the binding reagent on the solid support. Alternatively, or additionally, following immobilization of the binding reagent on the solid support, the solid support may be washed to remove any unbound binding reagent.

The apheresis column utilised in the various embodiments of the present invention acts as a leukapheresis treatment for cancer. The column acts to specifically remove one or more of CCR5, CCR6, CCR7, CCR8, CXCR4, CXCR7, CCR4, CCR9, CCR10, CXCR3 and/or CXCR5-expressing cells, by exploiting the interaction between CCR5, CCR6, CCR7, CCR8, CXCR4, CXCR7, CCR4, CCR9, CCR10, CXCR3 and/or CXCR5 expressed on the cell surface and a specific binding reagent immobilised on a solid support contained within or carried by the column. In other embodiments, the column acts to specifically remove one or more of Treg receptor expressing cells, in particular CLA, CCR4 and/or CCR8 expressing cells, by exploiting the interaction between Treg receptors such as CLA, CCR4 and CCR8 expressed on the cell surface and a specific binding reagent immobilised on a solid support contained within or carried by the column. The overall column typically comprises, consists of, or consists essentially of three combined components; 1) a housing which contains or carries 2) the solid support and 3) one or more binding reagents (immobilized thereon) which specifically bind one or more chemokine receptors. The housing may be manufactured from any suitable material for clinical use. In certain embodiments the housing is composed of a plastic material. The housing includes an in flow site for entry of blood and an out flow site for blood (depleted of target cells) to exit the column. The housing may be designed to maintain a continuous blood flow through the solid support matrix. The housing (as shown for example in FIG. 1) may include a top portion which comprises a distribution plate (2) at the inflow site (1) to spread the blood evenly over the entire matrix area. The distribution plate may act as a first safety barrier preventing larger particles flowing through the column and into the patient. However, the distribution plate is not essential and may be removed in some embodiments to decrease the overall resistance in the system. The column may contain one or more safety filter units (3 and 4) placed at the inflow (1) and/or outflow (5) sites of the plastic housing. Such filter units may act to prevent particles larger than blood cells passing in and/or out of the column. The safety filter units may contain a plurality of filters, such as two, three or four filters designed to be a robust barrier and stop all particles larger than blood cells passing through the column. Inclusion of safety filters (3 and 4) at both ends of the column serves to minimize the risk of leakage of particles into the patient, including in the event that the device is incorrectly connected resulting in blood flow in the opposite direction to that intended. The safety filters may comprise of any suitable pore size to prevent particles larger than blood cells from passing through the column, as would be readily understood by one skilled in the art. Suitable filters are commercially available. In specific embodiments, the pore size of the filter(s) is between approximately 60 μm and 100 μm, more specifically approximately 80 μm. The solid support and binding reagent components are discussed in further detail herein.

The volume of the housing may be varied depending upon the blood volumes intended to pass through the column. Typically, the volume of the housing is between approximately 40 ml and 200 ml, more specifically 50 ml to 150 ml or 60 ml to 120 ml. For leukemia treatments housing volumes tend to be higher, due to the large number of cells which are to be removed from the blood. In such embodiments, the housing volume is typically in the region of approximately 100 ml to 500 ml, such as 100 ml to 300 ml or 120 ml to 150 ml. In specific embodiments, the housing volume is approximately 120 ml.

The column is generally applied in the form of an apheresis circuit. In this context, the overall system includes the apheresis column, tubing and an appropriate pump to pump the blood around the circuit. The system is illustrated in FIG. 2. The patient (1) is connected to the extracorporeal circuit via sterile needles to veins in the right and the left arms. A saline bag (3) is also connected and the saline solution is pumped with a suitable pump (2). Blood is drawn from one arm of the patient through the sterile tubing system by the blood pump (4) and passed through the column (6) and back to the patient. The tubing system may be connected to the column via any suitable coupling, such as standard dialysis luer-lock couplings. The couplings on the column may be colour-coded for correct assembly. For example, red tubing for inflow to the red column top and blue tubing for outflow back to the patient. An air detector (8) may be present in the circuit. Inlet pressure (5) and/or Pven sensors (7) may additionally be employed to monitor the pressure in the circuit.

An apheresis pump, such as the 4008 ADS pump manufactured by Fresenius Medical Care or the Adamonitor pump, may monitor the patient's inflow and outflow. The pump may also monitor the pressure in the extracorporeal circulation. The pump may be able to discriminate air by a bubble catcher and air detector. A clot catcher filter may be positioned inside the bubble catcher. The pump may also incorporate an optical detector to distinguish between light, e.g. saline solution or air present in the tubing system and dark e.g. blood present in the tubing system.

A schematic diagram of a suitable pump, showing the air detector and optical filter is shown in FIG. 3. If the pump system detects air bubbles and optical fluctuations or if extracorporeal pressure values are out of the set range, then the pump may stop immediately. Alternatively or additionally a visual/audible alarm may be emitted.

The treatment methods of the various embodiments of the invention may thus rely upon an extracorporeal circuit. The methods may be considered as ex vivo or in vitro methods and be defined solely with reference to steps performed outside of the patient. In some embodiments, however, the method further comprises, prior to application of the blood to the column, collecting peripheral blood from the patient. In a further embodiment, the method further comprises, following the application of the blood to the column, infusing the blood depleted of (CCR5, CCR6, CCR7, CCR8, CXCR4, CXCR7, CCR4, CCR9, CCR10, CXCR3 and/or CXCR5) chemokine receptor expressing cells or of Treg receptor, such as CLA, CCR4 or CCR8 expressing cells (Tregs) to the patient. This is then a complete leukapheresis treatment method. Thus, a leukaphereis method, for treating cancer, comprises collecting peripheral blood from the patient; applying the peripheral blood to an apheresis column loaded with a solid support comprising one or more binding reagents capable of specifically binding to one or more chemokine receptors, in particular the chemokine receptor CCR5, CCR6, CCR7, CCR8, CXCR4, CXCR7, CCR4, CCR9, CCR10, CXCR3 and/or CXCR5; or the Treg receptors CLA, CCR4 and/or CCR8, immobilized directly or indirectly on the support thus removing one or more of CCR5, CCR6, CCR7, CCR8, CXCR4, CXCR7, CCR4, CCR9, CCR10, CXCR3 and/or CXCR5 expressing cells, or specifically Tregs in some embodiments, from the peripheral blood of the patient; and infusing the depleted blood (of chemokine receptor expressing cells) to the patient.

The peripheral blood may be continuously collected from the patient. Similarly, the depleted blood may be continuously infused to the patient, through use of an appropriate circuit as described herein. Thus, the support may be disposed in a column through which the blood is made to flow. This may be achieved using a suitable pump for example, as also described herein. Blood flow through the column enables the binding reagent(s) immobilized on the solid support to capture the cells expressing the chemokine receptor, thus depleting them from the blood and preventing their contribution to the cancer linked condition.

The methods of the various embodiments of the invention and binding reagents for use in the methods of the various embodiments of the invention may require that the patient has been selected for treatment on the basis of detecting an increase in the level of chemokine receptor, in particular, one or more of CCR5, CCR6, CCR7, CCR8, CXCR4, CXCR7, CCR4, CCR9, CCR10, CXCR3 and/or CXCR5 expressing cells and/or Treg receptor expressing cells, for example CLA, CCR4 and/or CCR8 expressing cells in a sample obtained from the patient. Such companion diagnostic methods are described in greater detail herein and are based, for example, on the observation that CCR5, CCR6, CCR7, CCR8, CXCR4, CXCR7, CCR4, CCR9, CCR10, CXCR3 and/or CXCR5 expression may be present on circulating tumour cells and CLA, CCR4 and/or CCR8 expression may be present specifically on regulatory T cells (that contribute to immune system avoidance by a cancer).

Thus, (in this context) in certain embodiments the invention also provides a method of diagnosing, monitoring progression of, or monitoring treatment of cancer comprising determining:

a) the levels of one or more of the chemokine receptor CCR5, CCR6, CCR7, CCR8, CXCR4, CXCR7, CCR4, CCR9, CCR10, CXCR3 and/or CXCR5 expressing cells b) levels of expression of one or more of CCR5, CCR6, CCR7, CCR8, CXCR4, CXCR7, CCR4, CCR9, CCR10, CXCR3 and/or CXCR5; and/or c) levels of cells with high expression of one or more of CCR5, CCR6, CCR7, CCR8, CXCR4, CXCR7, CCR4, CCR9, CCR10, CXCR3 and/or CXCR5 in a sample obtained from a subject, wherein high levels of one or more of CCR5, CCR6, CCR7, CCR8, CXCR4, CXCR7, CCR4, CCR9, CCR10, CXCR3 and/or CXCR5 expressing cells, high levels of expression of one or more of CCR5, CCR6, CCR7, CCR8, CXCR4, CXCR7, CCR4, CCR9, CCR10, CXCR3 and/or CXCR5 or high levels of cells with high expression of one or more of CCR5, CCR6, CCR7, CCR8, CXCR4, CXCR7, CCR4, CCR9, CCR10, CXCR3 and/or CXCR5 or increased levels of one or more of CCR5, CCR6, CCR7, CCR8, CXCR4, CXCR7, CCR4, CCR9, CCR10, CXCR3 and/or CXCR5 expressing cells compared to control, increased levels of expression of one or more of CCR5, CCR6, CCR7, CCR8, CXCR4, CXCR7, CCR4, CCR9, CCR10, CXCR3 and/or CXCR5 compared to a control or increased levels of cells with high expression of one or more of CCR5, CCR6, CCR7, CCR8, CXCR4, CXCR7, CCR4, CCR9, CCR10, CXCR3 and/or CXCR5 compared to a control indicate the presence or progression of cancer. Levels of chemokine receptor expression, as opposed to cell numbers, may also be investigated as increased levels of chemokine receptor expression per cell may also be diagnostically relevant.

Similarly, in other embodiments the invention also provides a method of diagnosing, monitoring progression of, or monitoring treatment of cancer comprising determining:

a) the levels of one or more Treg receptor expressing cells, in particular CLA, CCR4 and/or CCR8 expressing cells b) levels of expression of one or more of Treg receptors in particular CLA, CCR4 and/or CCR8; and/or c) levels of cells with high expression of one or more of Treg receptors in particular CLA, CCR4 and/or CCR8 in a sample obtained from a subject, wherein high levels of one or more of Treg receptors in particular CLA, CCR4 and/or CCR8 expressing cells, high levels of expression of one or more Treg receptors in particular CLA, CCR4 and/or CCR8 or high levels of cells with high expression of one or more of Treg receptors in particular CLA, CCR4 and/or CCR8 or increased levels of one or more of Treg receptors in particular CLA, CCR4 and/or CCR8 expressing cells compared to control, increased levels of expression of one or more of Treg receptors in particular CLA, CCR4 and/or CCR8 compared to a control or increased levels of cells with high expression of one or more of Treg receptors in particular CLA, CCR4 and/or CCR8 compared to a control indicate the presence or progression of cancer. Levels of Treg receptor expression, as opposed to cell numbers, may also be investigated as increased levels of Treg receptor expression per cell may also be diagnostically relevant. For the avoidance of doubt "Treg receptor expressing cells" may comprise, consist essentially of or consist of Tregs, in particular Tregs that express the specific receptor or receptors. This applies to all relevant aspects of the various embodiments of the invention.

"Diagnosing" is defined herein to include screening for a disease/condition or pre-indication of a disease/condition, identifying a disease/condition or pre-indication of a disease/condition and checking for recurrence of disease/condition following treatment. The methods of the various embodiments of the invention may also have prognostic value, and this is included within the definition of the term "diagnosis". The prognostic value of the methods of the various embodiments of the invention may be used as a marker of potential susceptibility to cancer by identifying levels of one or more of CCR5, CCR6, CCR7, CCR8, CXCR4, CXCR7, CCR4, CCR9, CCR10, CXCR3 and/or CXCR5; and/or of Treg receptors in particular CLA, CCR4 and/or CCR8. Thus patients at risk may be identified before the disease has a chance to manifest itself in terms of symptoms identifiable in the patient. In certain embodiments, diagnosis may be made in conjunction with other objective indicators of cancer. Thus, in specific embodiments, diagnosis is made in conjunction with one or more of the following indicators: clinical indications as known in the art. Also increased number of Tregs (CD4+ CD25hiCD127lo/− and Foxp3 positive) is a diagnostic indicator of poor prognosis in cancer. Determining the number of circulating leukemic or tumor cells and their chemokine receptor profile expression may be a further technique used in conjunction with the methods of the various embodiments of the invention.

"Monitoring progression of" includes performing the methods to monitor the stage and/or the state and progression of the cancer. Monitoring progression may involve performing the diagnostic methods multiple times on the same patient to determine whether the levels of one or more of CCR5, CCR6, CCR7, CCR8, CXCR4, CXCR7, CCR4, CCR9, CCR10, CXCR3 and/or CXCR5; and/or Treg receptors in particular CLA, CCR4 and/or CCR8 expressing cells are increasing, decreasing or remaining stable over a certain time period. This may be in the context of a treatment regime.

"Monitoring the success of a particular treatment" is defined to include determining the levels of one or more of CCR5, CCR6, CCR7, CCR8, CXCR4, CXCR7, CCR4, CCR9, CCR10, CXCR3 and/or CXCR5 expressing cells; and/or Treg receptor in particular CLA, CCR4 and/or CCR8 expressing cells before and after a treatment. The treatment is generally one aimed at treating cancer and may be a treatment according to one of the methods of the various embodiments of the invention as defined herein. Successful treatment may be determined with reference to a decrease in one or more of CCR5, CCR6, CCR7, CCR8, CXCR4, CXCR7, CCR4, CCR9, CCR10, CXCR3 and/or CXCR5 expressing cells; and/or Treg receptor in particular CLA, CCR4 and/or CCR8 expressing cells as a result of, or following, the treatment. Thus, in such methods a level of one or more of CCR5, CCR6, CCR7, CCR8, CXCR4, CXCR7, CCR4, CCR9, CCR10, CXCR3 and/or CXCR5 expressing cells; and/or Treg receptor in particular CLA, CCR4 and/or CCR8 expressing cells is determined prior to treatment. This level is recorded and a further assessment made at a predetermined time following the treatment. The comparison of levels of one or more of CCR5, CCR6, CCR7, CCR8, CXCR4, CXCR7, CCR4, CCR9, CCR10, CXCR3 and/or CXCR5 expressing cells; and/or Treg receptor in particular CLA, CCR4 and/or CCR8 expressing cells permits the success of the treatment to be monitored. In specific embodiments, a single treatment is sufficient to cause a depletion of around 10%, 20%, 30%, 40%, 50%, 60% or 70%, or higher, up to 80%, 90%, 95% or more, or any range of values between and including these amounts, of one or more specific chemokine receptors, in particular one or more of CCR5, CCR6, CCR7, CCR8, CXCR4, CXCR7, CCR4, CCR9, CCR10, CXCR3 and/or CXCR5 expressing cells; and/or Treg receptor in particular CLA, CCR4 and/or CCR8 expressing cells from the peripheral blood of the patient. In specific embodiments, at least around 50% depletion is achieved in a single treatment. Thus, successful treatment may be defined with reference to depletion of one or more of CCR5, CCR6, CCR7, CCR8, CXCR4, CXCR7, CCR4, CCR9, CCR10, CXCR3 and/or CXCR5 expressing cells; and/or Treg receptor in particular CLA, CCR4 and/or CCR8 expressing cells. Treatment may lead to depletion of between approximately 100 and 500 million of one of more of CCR5, CCR6, CCR7, CCR8, CXCR4, CXCR7, CCR4, CCR9, CCR10, CXCR3 and/or CXCR5 expressing cells, such as regulatory T lymphocytes and cancer cells; and/or Treg receptor in particular CLA, CCR4 and/or CCR8 expressing cells, in certain embodiments. Additional factors may be included to determine successful treatment. For example, a lack of increase in one or more of CCR5, CCR6, CCR7, CCR8, CXCR4, CXCR7, CCR4, CCR9, CCR10, CXCR3 and/or CXCR5 expressing cells; and/or Treg receptor in particular CLA, CCR4 and/or CCR8 expressing cells following treatment may indicate successful treatment in terms of preventing further progression of the condition, optionally combined with an improvement in other markers or staging of the cancer. By binding to the column through the binding reagent-chemokine receptor interaction, chemokine receptor expressing cells are immobilized. These immobilized cells express further unoccupied chemokine receptors, which may be of the same or different type to those used for capture. These additional chemokine receptors may permit circulating chemokines which contribute to the cancer to be captured from the peripheral blood. Thus, a reduction in circulating (specific) chemokine levels may provide a measure of successful treatment.

In specific embodiments, the condition associated with cancer or cancer treatment is selected from reducing levels of circulating tumour cells, reducing the incidence of tumour metastasis, removing regulatory T lymphocytes from the peripheral blood, or treating leukaemias such as chronic lymphocytic leukaemia, chronic myeloid leukemia, use for debulking in AML, ALL and before harvest for autologous bone marrow/stem cell transplantation and (treating the) leukemic phase of lymphoma.

The sample in which one or more of CCR5, CCR6, CCR7, CCR8, CXCR4, CXCR7, CCR4, CCR9, CCR10, CXCR3 and/or CXCR5 expressing cell levels, levels of expression of one or more of CCR5, CCR6, CCR7, CCR8, CXCR4, CXCR7, CCR4, CCR9, CCR10, CXCR3 and/or CXCR5 and/or levels of cells with high expression of one or more of CCR5, CCR6, CCR7, CCR8, CXCR4, CXCR7, CCR4, CCR9, CCR10, CXCR3 and/or CXCR5 (defined as $CCR5^{hi}$, $CCR6^{hi}$, $CCR7^{hi}$, $CCR8^{hi}$, $CXCR4^{hi}$, $CXCR7^{hi}$, $CCR4^{hi}$, $CCR9^{hi}$, $CCR10^{hi}$, $CXCR3^{hi}$ and/or $CXCR5^{hi}$) are determined may comprise any suitable tissue sample or body fluid sample. Generally, the test sample is obtained from a human subject. Typically, the sample is a blood sample, in particular a peripheral blood sample. The methods may involve determining levels of one or more of CCR5, CCR6, CCR7, CCR8, CXCR4, CXCR7, CCR4, CCR9, CCR10, CXCR3 and/or CXCR5 expressing tumour cells or regulatory T lymphocytes in certain embodiments.

Similarly, the sample in which one or more of Treg receptor in particular CLA, CCR4 and/or CCR8 expressing cell levels, levels of expression of one or more of Treg receptors in particular CLA, CCR4 and/or CCR8 and/or levels of cells with high expression of one or more of Treg receptors in particular CLA, CCR4 and/or CCR8 (defined as $CLA^{hi}$, $CCR4^{hi}$, and/or $CCR8^{hi}$) are determined may comprise any suitable tissue sample or body fluid sample.

Generally, the test sample is obtained from a human subject. Typically, the sample is a blood sample, in particular a peripheral blood sample. The methods may involve determining levels of one or more of Treg receptors in particular CLA, CCR4 and/or CCR8 expressing regulatory T lymphocytes in certain embodiments.

Levels of CCR5, CCR6, CCR7, CCR8, CXCR4, CXCR7, CCR4, CCR9, CCR10, CXCR3 and/or CXCR5 expressing cells, levels of expression of CCR5, CCR6, CCR7, CCR8, CXCR4, CXCR7, CCR4, CCR9, CCR10, CXCR3 and/or CXCR5 and/or levels of cells with high expression of CCR5, CCR6, CCR7, CCR8, CXCR4, CXCR7, CCR4, CCR9, CCR10, CXCR3 and/or CXCR5 (defined as $CCR5^{hi}$, $CCR6^{hi}$, $CCR7^{hi}$, $CCR8^{hi}$, $CXCR4^{hi}$, $CXCR7^{hi}$, $CCR4^{hi}$, $CCR9^{hi}$, $CCR10^{hi}$, $CXCR3^{hi}$ and/or $CXCR5^{hi}$) may be determined according to any suitable method. Similarly, levels of Treg receptors in particular CLA, CCR4 and/or CCR8 expressing cells, levels of expression of Treg receptors in particular CLA, CCR4 and/or CCR8 and/or levels of cells with high expression of Treg receptors in particular CLA, CCR4 and/or CCR8 (defined as $CLA^{hi}$, $CCR4^{hi}$, and/or $CCR8^{hi}$) may be determined according to any suitable method.

For example, flow cytometry may be employed in order to determine the number of cells expressing CCR5, CCR6, CCR7, CCR8, CXCR4, CXCR7, CCR4, CCR9, CCR10, CXCR3 and/or CXCR5; and/or Treg receptors in particular CLA, CCR4 and/or CCR8 expressing cells in the sample, to determine levels of CCR5, CCR6, CCR7, CCR8, CXCR4, CXCR7, CCR4, CCR9, CCR10, CXCR3 and/or CXCR5 expression; and/or Treg receptors in particular CLA, CCR4 and/or CCR8 expression and/or to identify levels of $CCR5^{hi}$, $CCR6^{hi}$, $CCR7^{hi}$, $CCR8^{hi}$, $CXCR4^{hi}$ and/or $CXCR7^{hi}$, optionally and/or $CCR4^{hi}$; and/or $CLA^{hi}$, $CCR4^{hi}$, and/or $CCR8^{hi}$ cells. Flow cytometric techniques are described herein and examples of commercially available antibodies suitably labelled for use in flow cytometry are set out in Table 1 for example. Alternatively, the method may involve steps of collecting and fixing the cells in the sample, followed by incubation with a suitable binding reagent that binds specifically to the CCR5, CCR6, CCR7, CCR8, CXCR4, CXCR7, CCR4, CCR9, CCR10, CXCR3 and/or CXCR5 chemokine receptor expressing cells; and/or Treg receptors in particular CLA, CCR4 and/or CCR8 expressing cells in the sample. Any suitable binding reagent, as defined herein, may be employed. For example, a CCR5, CCR6, CCR7, CCR8, CXCR4, CXCR7, CCR4, CCR9, CCR10, CXCR3 and/or CXCR5; and/or Treg receptor in particular CLA, CCR4 and/or CCR8 specific antibody may be employed. A wash step may be adopted following an incubation period to remove any unbound reagent. Suitable wash steps and incubation conditions would be well known to one skilled in the art. The binding reagent may be directly labeled in order to permit antibody binding to be directly determined. Alternatively a secondary binding reagent, such as an antibody, may be employed which binds to the first binding reagent and carries a label. Again, suitable incubation conditions and wash steps would be apparent to one skilled in the art. The primary and secondary binding reagents may form two halves of a binding pair. The binding interaction should not prevent the primary binding reagent binding to the CCR5, CCR6, CCR7, CCR8, CXCR4, CXCR7, CCR4, CCR9, CCR10, CXCR3 and/or CXCR5; and/or Treg in particular CLA, CCR4 and/or CCR8 receptor expressing cells, unless a competition assay is being employed. The two halves of a binding pair may comprise an antigen-antibody, antibody-antibody, receptor-ligand, biotin-streptavidin pair etc. in certain embodiments. Other techniques used to quantify chemokine (CCR5, CCR6, CCR7, CCR8, CXCR4, CXCR7, CCR4, CCR9, CCR10, CXCR3 and/or CXCR5; and/or Treg receptors in particular CLA, CCR4 and/or CCR8) receptor expressing cell levels, to quantify levels of CCR5, CCR6, CCR7, CCR8, CXCR4, CXCR7, CCR4, CCR9, CCR10, CXCR3 and/or CXCR5; and/or Treg receptor in particular CLA, CCR4 and/or CCR8 expression and/or to quantify levels of $CCR5^{hi}$, $CCR6^{hi}$, $CCR7^{hi}$, $CCR8^{hi}$, $CXCR4^{hi}$ or $CXCR7^{hi}$, optionally and/or $CCR4^{hi}$ cells; and/or $CLA^{hi}$, $CCR4^{hi}$, and/or $CCR8^{hi}$ cells include PCR-based techniques such as QT-PCR and protein based methods such as western blot. Quantitation may be achieved with reference to fixed cell lines carrying known numbers of various receptor expressing cells and/or known levels of receptor expression per cell. Such fixed cell lines are available commercially (for example ChemiScreen™ cell lines from Millipore). Methods analogous to the treatment methods of the various embodiments of the invention may also be employed, with binding of CCR expressing cells to the solid support being determined following peripheral blood being passed through the column.

The levels of CCR5, CCR6, CCR7, CCR8, CXCR4, CXCR7, CCR4, CCR9, CCR10, CXCR3 and/or CXCR5 expressing cells, levels of expression of CCR5, CCR6, CCR7, CCR8, CXCR4, CXCR7, CCR4, CCR9, CCR10, CXCR3 and/or CXCR5 and/or levels of cells with high expression of CCR5, CCR6, CCR7, CCR8, CXCR4, CXCR7, CCR4, CCR9, CCR10, CXCR3 and/or CXCR5 (defined as $CCR5^{hi}$, $CCR6^{hi}$, $CCR7^{hi}$, $CCR8^{hi}$, $CXCR4^{hi}$, $CXCR7^{hi}$, $CCR4^{hi}$, $CCR9^{hi}$, $CCR10^{hi}$, $CXCR3^{hi}$ and/or $CXCR5^{hi}$) may be determined relative to a suitable control. Similarly, levels of Treg receptor in particular CLA, CCR4 and/or CCR8 expressing cells, levels of expression of Treg receptors in particular CLA, CCR4 and/or CCR8 and/or levels of cells with high expression of Treg receptors in particular CLA, CCR4 and/or CCR8 (defined as $CLA^{hi}$, $CCR4^{hi}$, and/or $CCR8^{hi}$) may be determined relative to a suitable control. When diagnosing a condition associated with cancer, a threshold level of cells, level of expression of CCR5, CCR6, CCR7, CCR8, CXCR4, CXCR7, CCR4, CCR9, CCR10, CXCR3 and/or CXCR5; and/or Treg receptors in particular CLA, CCR4 and/or CCR8 and/or level of cells with high expression of CCR5, CCR6, CCR7, CCR8, CXCR4, CXCR7, CCR4, CCR9, CCR10, CXCR3 and/or CXCR5 (defined as $CCR5^{hi}$, $CCR6^{hi}$, $CCR7^{hi}$, $CCR8^{hi}$, $CXCR4^{hi}$, $CXCR7^{hi}$, $CCR4^{hi}$, $CCR9^{hi}$, $CCR10^{hi}$, $CXCR3^{hi}$ and/or $CXCR5^{hi}$); and/or Treg receptors in particular CLA, CCR4 and/or CCR8 expressing cells (defined as $CLA^{hi}$, $CCR4^{hi}$, and/or $CCR8^{hi}$) may be set at or over which a positive diagnosis is made. This threshold may be determined based upon measuring levels of CCR5, CCR6, CCR7, CCR8, CXCR4, CXCR7, CCR4, CCR9, CCR10, CXCR3 and/or CXCR5 expressing cells, levels of expression of CCR5, CCR6, CCR7, CCR8, CXCR4, CXCR7, CCR4, CCR9, CCR10, CXCR3 and/or CXCR5 and/or levels of cells with high expression of CCR5, CCR6, CCR7, CCR8, CXCR4, CXCR7, CCR4, CCR9, CCR10, CXCR3 and/or CXCR5 (defined as $CCR5^{hi}$, $CCR6^{hi}$, $CCR7^{hi}$, $CCR8^{hi}$, $CXCR4^{hi}$, $CXCR7^{hi}$, $CCR4^{hi}$, $CCR9^{hi}$, $CCR10^{hi}$, $CXCR3^{hi}$ and/or $CXCR5^{hi}$, optionally and/or $CCR4^{hi}$) in samples obtained from diseased patients and comparing these levels with levels of CCR5, CCR6, CCR7, CCR8, CXCR4, CXCR7, CCR4, CCR9, CCR10, CXCR3 and/or CXCR5 expressing cells, levels of expression of CCR5, CCR6, CCR7, CCR8, CXCR4, CXCR7, CCR4, CCR9, CCR10, CXCR3 and/or CXCR5 and/or levels of cells with high expression of CCR5, CCR6, CCR7, CCR8, CXCR4, CXCR7, CCR4, CCR9, CCR10, CXCR3 and/or CXCR5 (defined as $CCR5^{hi}$, $CCR6^{hi}$, $CCR7^{hi}$, $CCR8^{hi}$, $CXCR4^{hi}$, $CXCR7^{hi}$, $CCR4^{hi}$, $CCR9^{hi}$, $CCR10^{hi}$, $CXCR3^{hi}$ and/or $CXCR5^{hi}$) in samples obtained from healthy subjects. Similarly, where diagnosis is based upon Tregs specifically, this threshold may be determined based upon measuring levels of Treg receptors in particular CLA, CCR4 and/or CCR8 expressing cells, levels of expression of Treg receptors in particular CLA, CCR4 and/or CCR8 and/or levels of cells with high expression of Treg receptors in particular CLA, CCR4 and/or CCR8 (defined as $CLA^{hi}$, $CCR4^{hi}$, and/or $CCR8^{hi}$) in samples obtained from diseased patients and comparing these levels with levels of Treg receptor in particular CLA, CCR4 and/or CCR8 expressing cells, levels of expression of Treg receptors in particular CLA, CCR4 and/or CCR8 and/or levels of cells with high expression of Treg receptors in particular CLA, CCR4 and/or CCR8 (defined as $CLA^{hi}$, $CCR4^{hi}$, and/or $CCR8^{hi}$) in samples obtained from healthy subjects.

In certain embodiments, cancer is diagnosed on the basis of levels of chemokine receptor expressing cells. A positive diagnosis may be made in subjects based upon the presence of greater than about 10%, greater than about 20%, greater than about 30%, greater than about 40%, greater than about 50%, greater than about 55%, greater than about 60%, greater than about 65%, greater than about 70%, greater than about 75%, greater than about 80%, greater than about 85%, greater than about 90%, greater than about 95%, or more chemokine receptor expressing cells in the sample, as a percentage of total cells in the sample. In other embodiments, cancer is diagnosed on the basis of the presence of a about a 1.2 fold or greater increase, such as about a 1.5, 2, 2.5, 3, 3.5, 4, 4.5, 5, 10, 20, 50 or 100 or greater fold increase in chemokine receptor expressing cells, relative to healthy controls.

In specific embodiments, leukemias such as CLL are diagnosed on the basis of levels of CCR7 expressing cells. A positive diagnosis may be made in subjects where the levels of CCR7 expressing cells are sufficient to interfere with normal hematopoiesis. This may be when the majority of circulating cells are leukemic, and in addition are CCR7 positive. Thus, diagnosis may be made based upon the presence of greater than about 50%, such as greater than about 55%, greater than about 60%, greater than about 65%, greater than about 70%, greater than about 75%, greater than about 80%, greater than about 85%, greater than about 90%, greater than about 95% or more CCR7 expressing cells in the sample, as a percentage of total cells in the sample.

In other embodiments, cancer is diagnosed on the basis of measuring levels of Treg receptor expressing cells. Thus, a positive diagnosis according to the various embodiments of the invention may be made based upon the presence of a about a 1.2 fold or greater increase, such as about a 1.5, 2, 2.5, 3, 3.5, 4, 4.5, 5, 10, 20, 50 or 100 or greater fold increase in Treg receptor expressing cells, relative to healthy controls. In specific embodiments, cancers such as pancreatic cancer and urinary bladder cancer are diagnosed on the basis of measuring levels of CCR4 expressing cells. A positive diagnosis may be made in subjects where the levels of CCR4 expressing cells, in particular CCR4 expressing Tregs, are increased relative to healthy controls. Thus, a diagnosis according to the various embodiments of the invention may be made based upon the presence of about a 1.2-fold or greater increase, such as about a 1.5, 2, 2.5, 3, 3.5, 4, 4.5, 5, 10, 20, 50 or 100 or greater fold increase in CCR4 expressing cells, in particular CCR4 expressing Tregs, relative to healthy controls.

In certain embodiments, progression of cancer, which may be in the context of a treatment regime, is monitored on the basis of levels of chemokine receptor expressing cells at different time points. Progression of cancer may be indicated in subjects based upon an increase of greater than about 10%, such as an increase of greater than about 15%, greater than about 20%, greater than about 25%, greater than about 30%, greater than about 35%, greater than about 40%, greater than about 45%, greater than about 50%, greater than about 55%, greater than about 60%, greater than about 65%, greater than about 70%, greater than about 75% or more chemokine receptor expressing cells in the sample, as a percentage of total cells in the sample, compared to a sample taken from the same subject at an earlier time point. In other embodiments, progression of cancer is confirmed on the basis of the presence of a about a 1.2 fold or greater increase, such as about a 1.5, 2, 2.5, 3, 3.5, 4, 4.5, 5, 10, 20, 50 or 100 or greater fold increase in chemokine receptor expressing cells, relative to a sample taken from the same subject at an earlier time point.

In specific embodiments, leukemias such as CLL are monitored on the basis of levels of CCR7 expressing cells. Progression of the disease, which may be in the context of a treatment regime, may be indicated in subjects where the levels of CCR7 expressing cells become sufficient to interfere with normal hematopoiesis. This may be when the majority of circulating cells are leukemic, and in addition are CCR7 positive. Thus, progression, which may be in the context of a treatment regime, may be indicated based upon the presence of greater than about 50%, such as greater than about 55%, greater than about 60%, greater than about 65%, greater than about 70%, greater than about 75%, greater than about 80%, greater than about 85%, greater than about 90%, greater than about 95% or more CCR7 expressing cells in the sample, as a percentage of total cells in the sample or by an increase of greater than about 10%, such as greater than about 15%, greater than about 20%, greater than about 25%, greater than about 30%, greater than about 35%, greater than about 40%, greater than about 45%, greater than about 50%, greater than about 55%, greater than about 60%, greater than about 65%, greater than about 70%, greater than about 75% or more chemokine receptor expressing cells in the sample, as a percentage of total cells in the sample, compared to a sample taken from the same subject at an earlier time point.

Regression or successful treatment may be monitored based upon similar decreases over various time points. For example, regression or successful treatment may be indicated in subjects based upon a decrease of about 10%, such as a decrease of about 15%, about 20%, about 25%, about 30%, about 35%, about 40%, about 45%, about 50%, about 55%, about 60%, about 65%, about 70%, about 75% or more chemokine receptor expressing cells in the sample, as a percentage of total cells in the sample, compared to a sample taken from the same subject at an earlier time point. In other embodiments, regression of cancer is confirmed on the basis of the presence of a about a 1.2 fold or greater decrease, such as about a 1.5, 2, 2.5, 3, 3.5, 4, 4.5, 5, 10, 20, 50 or 100 or greater fold decrease in chemokine receptor expressing cells, relative to a sample taken from the same subject at an earlier time point.

In specific embodiments, leukemias such as CLL are monitored on the basis of levels of CCR7 expressing cells. Regression or successful treatment of the disease may be made in subjects where the levels of CCR7 expressing cells are no longer sufficient to interfere with normal hematopoiesis. This may be when the majority of circulating cells are no longer leukemic (and in addition are CCR7 positive). Thus, regression or successful treatment may be indicated based upon a decrease of about 50%, such as such as a decrease of about 55%, about 60%, about 65%, about 70%, about 75%, about 80%, about 85%, about 90%, about 95% or more CCR7 expressing cells in the sample, as a percentage of total cells in the sample or by a decrease of about 10%, such as a decrease of about 15%, about 20%, about 25%, about 30%, about 35%, about 40%, about 45%, about 50%, about 55%, about 60%, about 65%, about 70%, about 75% or more chemokine receptor expressing cells in the sample, as a percentage of total cells in the sample, compared to a sample taken from the same subject at an earlier time point.

In other embodiments, progression of cancer, which may be in the context of a treatment regime, is monitored on the basis of measuring levels of Treg receptor expressing cells.

Progression of cancer may be indicated based upon the presence of about a 1.2-fold or greater increase, such as about a 1.5, 2, 2.5, 3, 3.5, 4, 4.5, 5, 10, 20, 50 or 100 or greater fold increase in Treg receptor expressing cells, relative to a sample taken from the same subject at an earlier time point. In specific embodiments, cancers such as pancreatic cancer and urinary bladder cancer are monitored on the basis of measuring levels of CCR4 expressing cells. In certain embodiments, progression of cancer, which may be in the context of a treatment regime, is monitored on the basis of levels of Treg receptor expressing cells at different time points. Progression of cancer may be indicated in subjects based upon an increase of greater than about 10%, such as an increase of greater than about 15%, greater than about 20%, greater than about 25%, greater than about 30%, greater than about 35%, greater than about 40%, greater than about 45%, greater than about 50%, greater than about 55%, greater than about 60%, greater than about 65%, greater than about 70%, greater than about 75% or more Treg receptor expressing cells in the sample, as a percentage of total cells in the sample, compared to a sample taken from the same subject at an earlier time point.

Progression of cancer, which may be in the context of a treatment regime, may be identified in subjects where the levels of CCR4 expressing cells, in particular CCR4 expressing Tregs, are increased relative to a sample taken from the same subject at an earlier time point. Thus, progression according to the various embodiments of the invention may be indicated based upon the presence of a about a 1.2-fold or greater increase, such as about a 1.5, 2, 2.5, 3, 3.5, 4, 4.5, 5, 10, 20, 50 or 100 or greater fold increase in CCR4 expressing cells, in particular CCR4 expressing Tregs, relative to a sample taken from the same subject at an earlier time point.

Regression or successful treatment may be monitored based upon similar decreases over various time points. For example, in some embodiments regression or successful treatment of cancer may be indicated based upon a 1.2-fold or greater decrease, such as about a 1.5, 2, 2.5, 3, 3.5, 4, 4.5, 5, 10, 20, 50 or 100 or greater fold decrease in Treg receptor expressing cells, relative to a sample taken from the same subject at an earlier time point. In other embodiments, regression or successful treatment may be indicated in subjects based upon a decrease of about 10%, such as a decrease of about 15%, about 20%, about 25%, about 30%, about 35%, about 40%, about 45%, about 50%, about 55%, about 60%, about 65%, about 70%, about 75% or more Treg receptor expressing cells in the sample, as a percentage of total cells in the sample, compared to a sample taken from the same subject at an earlier time point.

In specific embodiments, cancers such as pancreatic cancer and urinary bladder cancer are monitored on the basis of measuring levels of CCR4 expressing cells. Regression or successful treatment may be identified in subjects where the levels of CCR4 expressing cells, in particular CCR4 expressing Tregs, are decreased relative to a sample taken from the same subject at an earlier time point. Thus, regression or successful treatment according to the various embodiments of the invention may be indicated based upon the presence of about a 1.2-fold or greater decrease, such as about a 1.5, 2, 2.5, 3, 3.5, 4, 4.5, 5, 10, 20, 50 or 100 or greater fold decrease in CCR4 expressing cells, in particular CCR4 expressing Tregs, relative to a sample taken from the same subject at an earlier time point.

Suitable software is freely available (such as the R project for statistical computing) to perform the necessary statistical analysis of the data obtained to calculate a useful threshold. The threshold may be set to maximize sensitivity and/or specificity of the test. Performance of the test in these respects may be measured by plotting a receiver operating characteristics (ROC) curve (sensitivity versus specificity). The area under the curve provides an indication of the overall performance of the test. Thus, once thresholds have been set for diagnosing the condition, a separate control experiment does not necessarily have to be run each time a sample is tested. Rather reference can simply be made to the pre-existing thresholds to determine the diagnosis. However, in certain embodiments, the sample is tested together with a control sample taken from a healthy subject to provide a comparator based upon essentially identical experimental conditions. The test sample is generally tested in parallel with the control sample. The test sample level of CCR5, CCR6, CCR7, CCR8, CXCR4, CXCR7, CCR4, CCR9, CCR10, CXCR3 and/or CXCR5 expressing cells; and/or Treg receptors in particular CLA, CCR4 and/or CCR8 expressing cells, levels of expression of CCR5, CCR6, CCR7, CCR8, CXCR4, CXCR7, CCR4, CCR9, CCR10, CXCR3 and/or CXCR5; and/or Treg receptor in particular CLA, CCR4 and/or CCR8 and/or levels of cells with high expression of CCR5, CCR6, CCR7, CCR8, CXCR4, CXCR7, CCR4, CCR9, CCR10, CXCR3 and/or CXCR5 (defined as $CCR5^{hi}$, $CCR6^{hi}$, $CCR7^{hi}$, $CCR8^{hi}$, $CXCR4^{hi}$, $CXCR7^{hi}$, $CCR4^{hi}$, $CCR9^{hi}$, $CCR10^{hi}$, $CXCR3^{hi}$ and/or $CXCR5^{hi}$); and/or Treg receptors in particular CLA, CCR4 and/or CCR8 (defined as $CLA^{hi}$, $CCR4^{hi}$, and/or $CCR8^{hi}$) can then be compared with that of the control sample to make the diagnosis. A control sample from a disease patient may also be tested in certain embodiments. Reference to controls permits relative levels ("high", "low" etc.) of CCR5, CCR6, CCR7, CCR8, CXCR4, CXCR7, CCR4, CCR9, CCR10, CXCR3 and/or CXCR5 expressing cells; and/or Treg receptors in particular CLA, CCR4 and/or CCR8 expressing cells in the test sample to be readily identified and the significance thereof interpreted. Reference to controls also permits relative levels of CCR5, CCR6, CCR7, CCR8, CXCR4, CXCR7, CCR4, CCR9, CCR10, CXCR3 and/or CXCR5 expression; and/or Treg receptors in particular CLA, CCR4 and/or CCR8 expression ("high", "low" etc.) within the cell population to be determined and the significance thereof interpreted.

Such determination may, for example, indicate the average levels of CCR5, CCR6, CCR7, CCR8, CXCR4, CXCR7, CCR4, CCR9, CCR10, CXCR3 and/or CXCR5 expression per cell; and/or Treg receptors in particular CLA, CCR4 and/or CCR8 expression per cell in the test sample.

Thus, in specific embodiments, high or higher levels of one or more of CCR5, CCR6, CCR7, CCR8, CXCR4, CXCR7, CCR4, CCR9, CCR10, CXCR3 and/or CXCR5 expressing cells; and/or Treg receptors in particular CLA, CCR4 and/or CCR8 expressing cells or high or higher levels of one or more of CCR5, CCR6, CCR7, CCR8, CXCR4, CXCR7, CCR4, CCR9, CCR10, CXCR3 and/or CXCR5 expression; and/or Treg receptors in particular CLA, CCR4 and/or CCR8 expression, for example average CCR5, CCR6, CCR7, CCR8, CXCR4, CXCR7, CCR4, CCR9, CCR10, CXCR3 and/or CXCR5 expression per cell; and/or Treg receptors in particular CLA, CCR4 and/or CCR8 expression per cell, or high or higher levels of one or more of $CCR5^{hi}$, $CCR6^{hi}$, $CCR7^{hi}$, $CCR8^{hi}$, $CXCR4^{hi}$, $CXCR7^{hi}$, $CCR4^{hi}$, $CCR9^{hi}$, $CCR10^{hi}$, $CXCR3^{hi}$ and/or $CXCR5^{hi}$ cells; and/or $CLA^{hi}$, $CCR4^{hi}$, and/or $CCR8^{hi}$ cells correlate with active disease or more active cancer. More active disease is generally related to higher levels of cellular proliferation in the case of cancer and so high or higher levels of one or more of CCR5, CCR6, CCR7, CCR8, CXCR4, CXCR7, CCR4, CCR9, CCR10, CXCR3 and/or CXCR5 expressing cells; and/or Treg receptors in particular CLA, CCR4 and/or CCR8 expressing cells or high or higher levels of one or more of CCR5, CCR6, CCR7, CCR8, CXCR4, CXCR7, CCR4, CCR9, CCR10, CXCR3 and/or CXCR5 expression; and/or Treg receptors in particular CLA, CCR4 and/or CCR8 expression, for example average CCR5, CCR6, CCR7, CCR8, CXCR4, CXCR7, CCR4, CCR9, CCR10, CXCR3 and/or CXCR5 expression per cell; and/or Treg receptors in particular CLA, CCR4 and/or CCR8 expression per cell, or high or higher levels of one or more of $CCR5^{hi}$, $CCR6^{hi}$, $CCR7^{hi}$, $CCR8^{hi}$, $CXCR4^{hi}$, $CXCR7^{hi}$, $CCR4^{hi}$, $CCR9^{hi}$, $CCR10^{hi}$, $CXCR3^{hi}$ and/or $CXCR5^{hi}$ cells; and/or $CLA^{hi}$, $CCR4^{hi}$, and/or $CCR8^{hi}$ cells may be expected to correlate with progression of the disease. Similarly, lower or low levels of one or more of CCR5, CCR6, CCR7, CCR8, CXCR4, CXCR7, CCR4, CCR9, CCR10, CXCR3 and/or CXCR5 expressing cells; and/or Treg receptors in particular CLA, CCR4 and/or CCR8 expressing cells, or low or lower levels of one or more of CCR5, CCR6, CCR7, CCR8, CXCR4, CXCR7, CCR4, CCR9, CCR10, CXCR3 and/or CXCR5 expression; and/or Treg receptors in particular CLA, CCR4 and/or CCR8 expression, for example average CCR5, CCR6, CCR7, CCR8, CXCR4, CXCR7, CCR4, CCR9, CCR10, CXCR3 and/or CXCR5 expression per cell; and/or Treg receptors in particular CLA, CCR4 and/or CCR8 expression per cell, or low or lower levels of one or more of $CCR5^{hi}$, $CCR6^{hi}$, $CCR7^{hi}$, $CCR8^{hi}$, $CXCR4^{hi}$, $CXCR7^{hi}$, $CCR4^{hi}$, $CCR9^{hi}$, $CCR10^{hi}$, $CXCR3^{hi}$ and/or $CXCR5^{hi}$ cells; and/or $CLA^{hi}$, $CCR4^{hi}$, and/or $CCR8^{hi}$ cells may correlate with a lack of active inflammation or cancer. This may be defined as "less active disease". It can readily be envisaged that control samples may be assessed and levels of CCR5, CCR6, CCR7, CCR8, CXCR4, CXCR7, CCR4, CCR9, CCR10, CXCR3 and/or CXCR5 expressing cells; and/or Treg receptor in particular CLA, CCR4 and/or CCR8 expressing cells, levels of expression of CCR5, CCR6, CCR7, CCR8, CXCR4, CXCR7, CCR4, CCR9, CCR10, CXCR3 and/or CXCR5; and/or Treg receptors in particular CLA, CCR4 and/or CCR8 expression and/or levels of cells with high expression of CCR5, CCR6, CCR7, CCR8, CXCR4, CXCR7, CCR4, CCR9, CCR10, CXCR3 and/or CXCR5 (defined as $CCR5^{hi}$, $CCR6^{hi}$, $CCR7^{hi}$, $CCR8^{hi}$, $CXCR4^{hi}$, $CXCR7^{hi}$, $CCR4^{hi}$, $CCR9^{hi}$, $CCR10^{hi}$, $CXCR3^{hi}$ and/or $CXCR5^{hi}$); and/or Treg receptors in particular CLA, CCR4 and/or CCR8 (defined as $CLA^{hi}$, $CCR4^{hi}$, and/or $CCR8^{hi}$) determined across the range of severities of cancer. This may assist in correlating the levels of CCR5, CCR6, CCR7, CCR8, CXCR4, CXCR7, CCR4, CCR9, CCR10, CXCR3 and/or CXCR5 expressing cells; and/or Treg receptors in particular CLA, CCR4 and/or CCR8 expressing cells, levels of expression of CCR5, CCR6, CCR7, CCR8, CXCR4, CXCR7, CCR4, CCR9, CCR10, CXCR3 and/or CXCR5; and/or Treg receptors in particular CLA, CCR4 and/or CCR8 and/or levels of cells with high expression of CCR5, CCR6, CCR7, CCR8, CXCR4, CXCR7, CCR4, CCR9, CCR10, CXCR3 and/or CXCR5 (defined as $CCR5^{hi}$, $CCR6^{hi}$, $CCR7^{hi}$, $CCR8^{hi}$, $CXCR4^{hi}$, $CXCR7^{hi}$, $CCR4^{hi}$, $CCR9^{hi}$, $CCR10^{hi}$, $CXCR3^{hi}$ and/or $CXCR5^{hi}$); and/or Treg receptors in particular CLA, CCR4 and/or CCR8 (defined as $CLA^{hi}$, $CCR4^{hi}$, and/or $CCR8^{hi}$) in the test sample with the relative severity of the condition.

When monitoring progression of, or monitoring treatment of cancer, the control samples may be taken from the subject at an earlier time point. They may, however, be based upon known reference values as discussed above. Thus, relative levels of CCR5, CCR6, CCR7, CCR8, CXCR4, CXCR7, CCR4, CCR9, CCR10, CXCR3 and/or CXCR5 expressing cells; and/or Treg receptor in particular CLA, CCR4 and/or CCR8 expressing cells, relative levels of CCR5, CCR6, CCR7, CCR8, CXCR4, CXCR7, CCR4, CCR9, CCR10, CXCR3 and/or CXCR5 expression; and/or Treg receptors in particular CLA, CCR4 and/or CCR8 expression including relative levels of average CCR5, CCR6, CCR7, CCR8, CXCR4, CXCR7, CCR4, CCR9, CCR10, CXCR3 and/or CXCR5 expression per cell; and/or Treg receptors in particular CLA, CCR4 and/or CCR8 expression per cell or relative levels of $CCR5^{hi}$, $CCR6^{hi}$, $CCR7^{hi}$, $CCR8^{hi}$, $CXCR4^{hi}$ or $CXCR7^{hi}$, optionally and/or $CCR4^{hi}$ cells; and/or $CLA^{hi}$, $CCR4^{hi}$, and/or $CCR8^{hi}$ cells may be with reference to samples taken from the same subject at a different point in time. In certain embodiments, decreased levels of one or more of CCR5, CCR6, CCR7, CCR8, CXCR4, CXCR7, CCR4, CCR9, CCR10, CXCR3 and/or CXCR5 expressing cells; and/or Treg receptors in particular CLA, CCR4 and/or CCR8 expressing cells, decreased relative levels of one or more of CCR5, CCR6, CCR7, CCR8, CXCR4, CXCR7, CCR4, CCR9, CCR10, CXCR3 and/or CXCR5 expression; and/or Treg receptors in particular CLA, CCR4 and/or CCR8 expression including decreased relative levels of average CCR5, CCR6, CCR7, CCR8, CXCR4, CXCR7, CCR4, CCR9, CCR10, CXCR3 and/or CXCR5 expression per cell; and/or Treg receptors in particular CLA, CCR4 and/or CCR8 expression per cell, or decreased relative levels of one or more of $CCR5^{hi}$, $CCR6^{hi}$, $CCR7^{hi}$, $CCR8^{hi}$, $CXCR4^{hi}$, $CXCR7^{hi}$, $CCR4^{hi}$, $CCR9^{hi}$, $CCR10^{hi}$, $CXCR3^{hi}$ and/or $CXCR5^{hi}$ cells; and/or $CLA^{hi}$, $CCR4^{hi}$, and/or $CCR8^{hi}$ cells correlate with successful treatment. The treatment may be any suitable treatment, but in specific embodiments is a treatment according to the various embodiments of the invention.

When monitoring progression of cancer, increased levels of one or more of CCR5, CCR6, CCR7, CCR8, CXCR4, CXCR7, CCR4, CCR9, CCR10, CXCR3 and/or CXCR5 expressing cells; and/or Treg receptors in particular CLA, CCR4 and/or CCR8 expressing cells increased relative levels of one or more of CCR5, CCR6, CCR7, CCR8, CXCR4, CXCR7, CCR4, CCR9, CXCR3 and/or CXCR5 expression; and/or Treg receptors in particular CLA, CCR4 and/or CCR8 expression including increased relative levels of average CCR5, CCR6, CCR7, CCR8, CXCR4, CXCR7, CCR4, CCR9, CCR10, CXCR3 and/or CXCR5 expression per cell; and/or Treg receptors in particular CLA, CCR4 and/or CCR8 expression per cell or increased relative levels of one or more of $CCR5^{hi}$, $CCR6^{hi}$, $CCR7^{hi}$, $CCR8^{hi}$, $CXCR4^{hi}$, $CXCR7^{hi}$, $CCR4^{hi}$, $CCR9^{hi}$, $CCR10^{hi}$, $CXCR3^{hi}$ and/or $CXCR5^{hi}$ cells; and/or $CLA^{hi}$, $CCR4^{hi}$, and/or $CCR8^{hi}$ cells may indicate the progression of condition or disease. Thus, if levels of one or more of CCR5, CCR6, CCR7, CCR8, CXCR4, CXCR7, CCR4, CCR9, CCR10, CXCR3 and/or CXCR5 expressing cells; and/or Treg receptors in particular CLA, CCR4 and/or CCR8 expressing cells, levels of expression of one or more of CCR5, CCR6, CCR7, CCR8, CXCR4, CXCR7, CCR4, CCR9, CCR10, CXCR3 and/or CXCR5; and/or Treg receptors in particular CLA, CCR4 and/or CCR8 and/or levels of cells with high expression of one or more of CCR5, CCR6, CCR7, CCR8, CXCR4, CXCR7, CCR4, CCR9, CCR10, CXCR3 and/or CXCR5 (defined as $CCR5^{hi}$, $CCR6^{hi}$, $CCR7^{hi}$, $CCR8^{hi}$, $CXCR4^{hi}$, $CXCR7^{hi}$, $CCR4^{hi}$, $CCR9^{hi}$, $CCR10^{hi}$, $CXCR3^{hi}$ and/or $CXCR5^{hi}$); and/or Treg receptors in particular CLA, CCR4 and/or CCR8 expressing cells (defined as CLA$^{hi}$, CCR4$^{hi}$, and/or CCR8$^{hi}$) are increased in a sample taken later than a sample from the same patient this may indicate progression of the condition.

Since the levels of one or more of CCR5, CCR6, CCR7, CCR8, CXCR4, CXCR7, CCR4, CCR9, CCR10, CXCR3 and/or CXCR5 expressing cells, levels of one or more of CCR5, CCR6, CCR7, CCR8, CXCR4, CXCR7, CCR4, CCR9, CCR10, CXCR3 and/or CXCR5 expression or levels of one or more of CCR5$^{hi}$, CCR6$^{hi}$, CCR7$^{hi}$, CCR8$^{hi}$, CXCR4$^{hi}$, CXCR7$^{hi}$, CCR4$^{hi}$, CCR9$^{hi}$, CCR10$^{hi}$, CXCR3$^{hi}$ and/or CXCR5$^{hi}$ cells are diagnostically relevant, determining such levels in a sample obtained from a subject may influence treatment selection for that subject. Accordingly, in certain embodiments the invention provides a method of selecting a suitable treatment for cancer comprising determining:

a) the levels of one or more of the chemokine receptor CCR5, CCR6, CCR7, CCR8, CXCR4, CXCR7, CCR4, CCR9, CCR10, CXCR3 and/or CXCR5 expressing cells b) levels of expression of one or more of CCR5, CCR6, CCR7, CCR8, CXCR4, CXCR7, CCR4, CCR9, CCR10, CXCR3 and/or CXCR5; and/or c) levels of cells with high expression of one or more of CCR5, CCR6, CCR7, CCR8, CXCR4, CXCR7, CCR4, CCR9, CCR10, CXCR3 and/or CXCR5 in a sample obtained from a subject, wherein high levels of one or more of CCR5, CCR6, CCR7, CCR8, CXCR4, CXCR7, CCR4, CCR9, CCR10, CXCR3 and/or CXCR5 expressing cells, high levels of expression of one or more of CCR5, CCR6, CCR7, CCR8, CXCR4, CXCR7, CCR4, CCR9, CCR10, CXCR3 and/or CXCR5 or high levels of cells with high expression of CCR5, CCR6, CCR7, CCR8, CXCR4, CXCR7, CCR4, CCR9, CCR10, CXCR3 and/or CXCR5 or increased levels of one or more of CCR5, CCR6, CCR7, CCR8, CXCR4, CXCR7, CCR4, CCR9, CCR10, CXCR3 and/or CXCR5 expressing cells compared to control, increased levels of expression of one or more of CCR5, CCR6, CCR7, CCR8, CXCR4, CXCR7, CCR4, CCR9, CCR10, CXCR3 and/or CXCR5 compared to a control or increased levels of cells with high expression of one or more of CCR5, CCR6, CCR7, CCR8, CXCR4, CXCR7, CCR4, CCR9, CCR10, CXCR3 and/or CXCR5 compared to a control, result in selection of a treatment as defined herein for treatment of the (condition associated with) cancer. In certain embodiments, the chemokine receptor expressing cells are high chemokine receptor expressing cells, in particular, high CCR5, CCR6, CCR7, CCR8, CXCR4, CXCR7, CCR4, CCR9, CCR10, CXCR3 and/or CXCR5 expressing cells.

In specific embodiments, cancer is treated on the basis of measuring levels of chemokine receptor expressing cells. Thus, a treatment according to the various embodiments of the invention may be applied based upon the presence of greater than about 10%, greater than about 20%, greater than about 30%, greater than about 40%, greater than about 50%, greater than about 55%, greater than about 60%, greater than about 65%, greater than about 70%, greater than about 75%, greater than about 80%, greater than about 85%, greater than about 90%, greater than about 95%, or more chemokine receptor expressing cells in the sample, as a percentage of total cells in the sample. In other embodiments, cancer is treated according to the various embodiments of the invention on the basis of the presence of a about a 1.5 fold or greater increase, such as about a 2, 2.5, 3, 3.5, 4, 4.5, 5, 10, 20, 50 or 100 or greater fold increase in chemokine receptor expressing cells, relative to healthy controls.

In specific embodiments, leukemias such as CLL are treated on the basis of measuring levels of CCR7 expressing cells. A positive decision to treat the subject may be made in subjects where the levels of CCR7 expressing cells are sufficient to interfere with normal hematopoiesis. This may be when the majority of circulating cells are leukemic, and in addition are CCR7 positive. Thus, a treatment according to the various embodiments of the invention may be applied based upon the presence of greater than about 50%, such as greater than about 55%, greater than about 60%, greater than about 65%, greater than about 70%, greater than about 75%, greater than about 80%, greater than about 85%, greater than about 90%, greater than about 95% or more CCR7 expressing cells in the sample, as a percentage of total cells in the sample.

Similarly, since the levels of one or more of Treg receptors in particular CLA, CCR4 and/or CCR8 expressing cells, levels of one or more of Treg receptors in particular CLA, CCR4 and/or CCR8 expression or levels of one or more of CLA$^{hi}$, CCR4$^{hi}$, and/or CCR8$^{hi}$ cells are diagnostically relevant, determining such levels in a sample obtained from a subject may influence treatment selection for that subject. Accordingly, in a related aspect the invention provides a method of selecting a suitable treatment for cancer comprising determining:

a) the levels of one or more Treg receptor expressing cells, in particular CLA, CCR4 and/or CCR8 expressing cells b) levels of expression of one or more of Treg receptors in particular CLA, CCR4 and/or CCR8; and/or c) levels of cells with high expression of one or more of Treg receptors in particular CLA, CCR4 and/or CCR8 in a sample obtained from a subject, wherein high levels of one or more of Treg receptors in particular CLA, CCR4 and/or CCR8 expressing cells, high levels of expression of one or more Treg receptors in particular CLA, CCR4 and/or CCR8 or high levels of cells with high expression of one or more of Treg receptors in particular CLA, CCR4 and/or CCR8 or increased levels of one or more of Treg receptors in particular CLA, CCR4 and/or CCR8 expressing cells compared to control, increased levels of expression of one or more of Treg receptors in particular CLA, CCR4 and/or CCR8 compared to a control or increased levels of cells with high expression of one or more of Treg receptors in particular CLA, CCR4 and/or CCR8 compared to a control result in selection of a treatment as defined herein for treatment of the (condition associated with) cancer. In certain embodiments, the chemokine receptor expressing cells are high chemokine receptor expressing cells, in particular, high Treg receptor in particular CLA, CCR4 and/or CCR8 expressing cells.

In some embodiments, cancer is treated on the basis of measuring levels of Treg receptor expressing cells. Thus, a treatment according to the various embodiments of the invention may be applied based upon the presence of about a 1.5-fold or greater increase, such as about a 2, 2.5, 3, 3.5, 4, 4.5, 5, 10, 20, 50 or 100 or greater fold increase in Treg receptor expressing cells, relative to healthy controls. In other embodiments, cancer is treated according to the various embodiments of the invention based upon the presence of greater than about 10%, greater than about 20%, greater than about 30%, greater than about 40%, greater than about 50%, greater than about 55%, greater than about 60%, greater than about 65%, greater than about 70%, greater than about 75%, greater than about 80%, greater than about 85%, greater than about 90%, greater than about 95%, or more Treg receptor expressing cells in the sample, as a percentage of total cells in the sample.

In specific embodiments, cancers such as pancreatic cancer and urinary bladder cancer are treated on the basis of measuring levels of CCR4 expressing cells. A positive decision to treat the subject may be made in subjects where the levels of CCR4 expressing cells, in particular CCR4 expressing Tregs, are increased relative to healthy controls. Thus, a treatment according to the various embodiments of the invention may be applied based upon the presence of about a 1.5-fold or greater increase, such as about a 2, 2.5, 3, 3.5, 4, 4.5, 5, 10, 20, 50 or 100 or greater fold increase in CCR4 expressing cells, in particular CCR4 expressing Tregs, relative to healthy controls.

For the avoidance of doubt, all embodiments described in respect of the methods of the various embodiments of the invention apply to these aspects mutatis mutandis and are not repeated for reasons of conciseness. Specifically, cancer may be indicated in conjunction with one or more clinical indications as known in the art. Also increased number of Tregs (CD4+CD25hiCD127lo/− and Foxp3 positive) is a diagnostic indicator of poor prognosis in cancer. Determining the number of circulating leukemic or tumor cells and their chemokine receptor profile expression may be a further technique used in conjunction with the methods of the various embodiments of the invention.

The cancer or cancer treatment may be selected from reducing levels of circulating tumour cells, reducing the incidence of tumour metastasis, removing regulatory T lymphocytes from the peripheral blood, or treating leukaemias such as chronic lymphocytic leukaemia, chronic myeloid leukemia, use for debulking in AML, ALL and before harvest for autologous bone marrow/stem cell transplantation and treatment of the leukemic phase of lymphoma. In specific embodiments, the sample is a peripheral blood sample.

The methods and medical uses of the various embodiments of the invention thus can be tailored to the need of individual patients or groups of patients on the basis of the various diagnostic methods of the various embodiments of the invention. By removing from the circulation one or more of CCR5, CCR6, CCR7, CCR8, CXCR4, CXCR7, CCR4, CCR9, CCR10, CXCR3 and/or CXCR5 expressing cells; and/or Treg receptor in particular CLA, CCR4 and/or CCR8 expressing cells, such as tumour cells and regulatory T lymphocytes, upregulated in cancer, an important factor in the disease can be controlled. The methods of the various embodiments of the invention may be effective in treating or reversing conditions such as by reducing levels of circulating tumour cells, reducing the incidence of tumour metastasis, removing regulatory T lymphocytes from the peripheral blood, or treating leukaemias such as chronic lymphocytic leukaemia, chronic myeloid leukemia, use for debulking in AML, ALL and before harvest for autologous bone marrow/stem cell transplantation and treatment of the leukemic phase of lymphoma.

The various embodiments of the invention will now be described in more detail by reference to the following non-limiting embodiments and examples:

DESCRIPTION OF PREFERRED EMBODIMENTS

Figure 1:
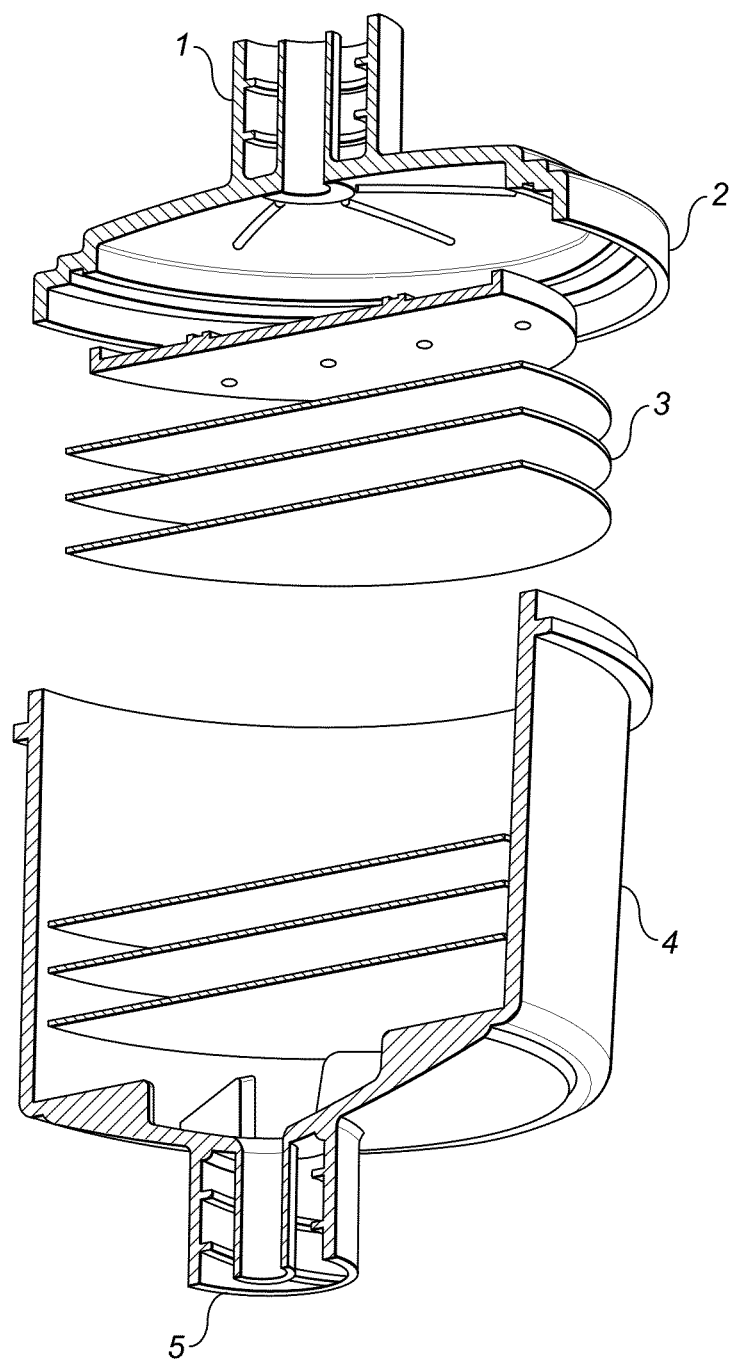
FIG. 1—The plastic house and top showing the distribution plate (2) and safety filter units (3 and 4).

The mechanism behind seeding of metastatic cells in to particular organs is by the expression of chemokines in the organ recruiting chemokine receptor expressing tumor cells. For example metastatic colon cancer cells express CCR6 and they home to liver because CCL20 is expressed in the liver allowing entrance of CCR6 expressing cancer cells.

In non Hodgkin lymphomas (T-NHL) the expression of CCR7 indicates a higher lymphatic dissemination which was demonstrated to migrate towards CCL21, the preferred chemokine for entrance of cells in to lymphoid organs.

Lung cancer metastases seem to be dependent on the expression of CXCR4 on tumour cells and the local expression of the corresponding chemokine CXCL12 (SDF-1) for the successful metastasis. In line with these findings development of small molecules for inhibition of CXCR4 mediated metastasis is under development.

Regulatory T cells (Tregs) are upregulated in many cancers as an immune escape mechanism induced by the tumor. In order to avoid immune recognition and elimination tumors activate and recruit Tregs. The production of chemokines by the tumor results in recruitment of circulating Tregs and therefore protection against immune recognition and elimination. Tregs may be recruited to the tumour by CCL17 and CCL22 binding to CCR4 expressed on the Treg. In addition CCR8 mediated recruitment by CCL1 may occur. Since many treatment regimes with chemotherapy involve activation of the immune system, eliminating Tregs in the circulation by leukapheresis may thus favour immune recognition and elimination of tumor cells, thereby enhancing cancer therapy.

In chronic leukemic disorders the number of circulating tumor cells inhibit normal hematopoeis and therefore cause symptoms. The increased production of chemokines such as CCL3 correlates with poor prognosis (Blood. 2011 Feb. 3; 117(5):1662-9. Epub 2010 Nov. 29). Thus elimination of chemokine receptor expressing leukemic cells will favorably affect the disease in terms of symptoms and disease progression.

It is shown herein that cancer patients, in particular subjects suffering from UBC and PC, exhibit an increased frequency of CCR4 expressing circulating Tregs and that this response is specific to Tregs (and does not apply to other T lymphocytes). CCR4 expressing cells may be thus be targeted in order to treat cancer. Treatment may rely upon suitable binding reagents such as CCL22 (MDC) and derivatives thereof, as described herein in further detail. It is also shown herein that subject suffering from leukemias, such as CLL, have a highly increased number of circulating B cells. The B cells express characteristic chemokine receptors, such as CCR7. It is also shown herein that CCR7 expressing B cells may be efficiently depleted using MIP3b as a specific binding reagent in a leukapheresis method.

Example 1—Tailored Leukapheresis

Column Design and Properties
Introduction

Apheresis is an established treatment used for depletion of blood components, such as antibodies, low-density lipoproteins (LDL) and blood cells. Leukapheresis is the apheresis treatment used for removal of white blood cells, leukocytes. The patient is connected to an extracorporeal blood circulating system; the blood is drawn from a vein in one arm, passed through a column device and returned into the other arm of the patient. Side effects of leukapheresis treatments are varying from mild events like headache, dizziness, hypotension, palpitation and flush seen in 0.1 to 5% of treated patients.

The Column

The column is intended to be used as a leukapheresis treatment for cancer. It will specifically remove CCR5, CCR6, CCR7, CCR8, CXCR4, CXCR7, CCR4, CCR9, CCR10, CXCR3 and/or CXCR5-expressing cells, such as tumour cells and leukocytes, such as regulatory T lymphocytes, through the use of a binding reagent, more specifically an MIP-3alpha (CCL20), CCL19, CCL21, CCL1, CXCL11, CXCL12, CCL25 (TECK), CCL27 (CTACK), CCL28 (MEC), CXCL9 (MIG), CXCL10 (IP10), CXCL13 (BCA-1), CCL17 (TARC) and CCL22 (MDC) containing resin, exploiting the CCR5, CCR6, CCR7, CCR8, CXCR4, CXCR7, CCR4, CCR9, CCR10, CXCR3 and/or CXCR5-chemokine interaction. Treg receptor expressing cells, such as CLA receptor, CCR4 or CCR8 expressing cells may be specifically removed through the use of an appropriate binding reagent, more specifically an SELE, CCL17, CCL22 and/or CCL1 containing resin. The column consists of three combined components, the plastic house, the streptavidin (SA) Sepharose™ BigBeads matrix and one or more of biotinylated MIP-3alpha (CCL20), CCL19, CCL21, CCL1, CXCL11, CXCL12, CCL25 (TECK), CCL27 (CTACK), CCL28 (MEC), CXCL9 (MIG), CXCL10 (IP10), CXCL13 (BCA-1), CCL17 (TARC) and CCL22 (MDC) and/or SELE, CCL17, CCL22 and/or CCL1 bound to the matrix. The treatment is conducted using the same techniques as a standard apheresis procedure.

The Plastic House (FIG. 1)

The plastic house, designed to keep a continuous blood flow through the matrix, consists of a transparent body and red-coloured top. The top has a distribution plate (2) at the inflow site (1) to spread the blood evenly over the entire matrix area. The plate is the first safety barrier preventing larger particles flowing through the column and into the patient. Safety filter units (3 and 4) are placed at the inflow (1) and outflow (5) sites of the plastic housing. The safety filter unit contains three filters designed to be a robust barrier and stop all particles larger than blood cells passing through the column. The plastic housing design is shown in FIG. 1. The design with safety filters (3 and 4) at both ends of the column device will minimize the risk of leakage of particles into the patient, including in the event that the device is placed up side down with the blood flow in the opposite direction to that anticipated.

Streptavidin Sepharose™ BigBeads

The second component in the device is the affinity matrix called streptavidin Sepharose™ BigBeads (Sepharose™ GE Healthcare, Sweden). Sepharose™ is a cross linked, beaded-form of agarose, which is a polysaccharide extracted from seaweed. Sepharose™ and agarose are commonly used as column matrices in biomedical affinity techniques. It is chosen for its optimal distribution capacity and can provide a large available area for affinity binding.

Binding Reagent

Coupled to the matrix is the third component of the device, one or more binding reagents that bind specifically to CCR5, CCR6, CCR7, CCR8, CXCR4, CXCR7, CCR4, CCR9, CCR10, CXCR3 and/or CXCR5 and/or to CLA receptor, CCR4 and/or CCR8 where Tregs are specifically targeted. One or more chemokines selected from the group consisting of: MIP-3alpha (CCL20), CCL19, CCL21, CCL1, CXCL11, CXCL12, CCL25 (TECK), CCL27 (CTACK), CCL28 (MEC), CXCL9 (MIG), CXCL10 (IP10), CXCL13 (BCA-1), CCL17 (TARC) and CCL22 (MDC) may be employed. Alternatively, SELE, CCL17, CCL22 and/or CCL1 may be employed to target Tregs. These peptides may be synthetic, engineered versions of the human chemokine, which are truncated and biotinylated, but retain binding activity to the CCR5, CCR6, CCR7, CCR8, CXCR4, CXCR7, CCR4, CCR9, CCR10, CXCR3 and/or CXCR5 receptor (or CLA receptor, CCR4 and/or CCR8 where Tregs are targeted). By biotinylating the engineered chemokine, it is able to bind to the streptavidin molecules in the Sepharose™ matrix. The biotin-streptavidin binding is known to be one of the strongest biological interactions with a Kd in the order of $4\times10^{-14}$ M. The calculated ratio of streptavidin:biotin binding sites in the column is 10:1. Therefore, the coupling between the matrix and chemokine will be immediate, minimising the risk of chemokine decoupling from the matrix.

The Apheresis System

To conduct the leukapheresis the following components are needed; the column, tubing system, and a 4008 ADS pump (Fresenius Medical Care).

The Circuit

Figure 2:
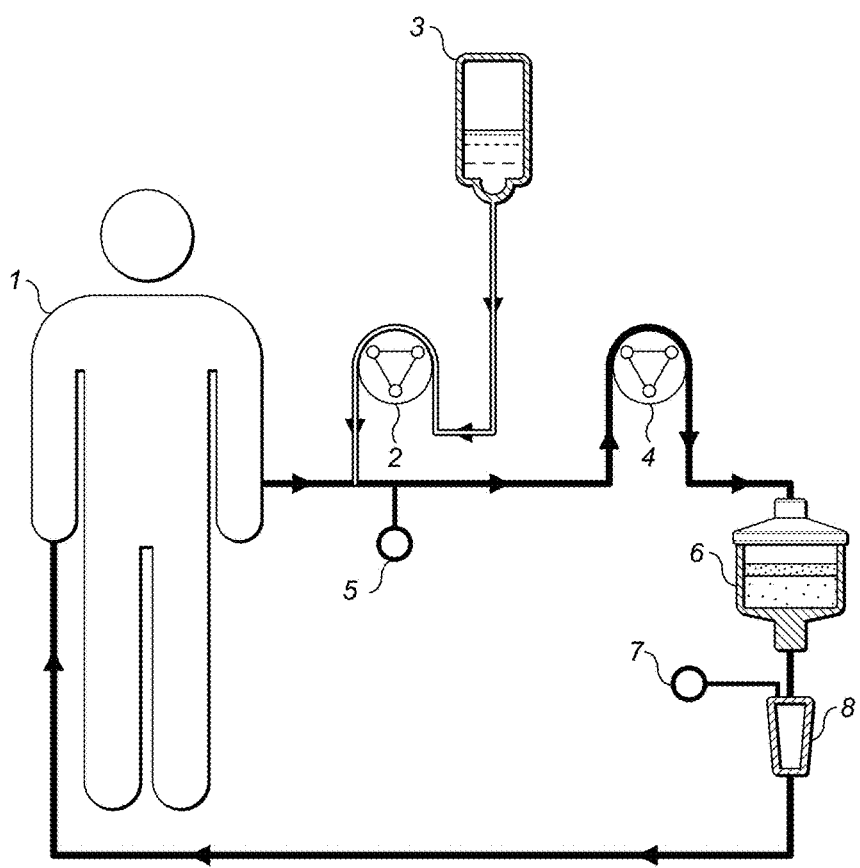
FIG. 2—The overall leukapheresis system.

The system is illustrated in FIG. 2. The patient (1) is connected to the extracorporeal circuit via sterile Venflon needles to veins in the right and the left arms. A saline bag (3) is also connected and the saline solution is pumped with an ACD pump (2). Blood is drawn from one arm of the patient through the sterile tubing system by the blood pump (4) and passed through the column (6) and back to the patient. The tubing system is connected to the column via standard dialysis luer-lock couplings. The couplings on the column are colour-coded for correct assembly; red tubing for inflow to the red column top and blue tubing for outflow back to the patient. An air detector (8) is present. Inlet pressure (5) and Pven sensors (7) are employed to monitor the pressure in the circuit.

The 4008 ADS Pump

An apheresis pump, from Fresenius Medical Care, monitors the patient's inflow and outflow, the pressure in the extracorporeal circulation and can discriminate air by a bubble catcher and air detector. A clot catcher filter is placed inside the bubble catcher. The pump also has an optical detector to distinguish between light, e.g. saline solution or air present in the tubing system and dark e.g. blood present in the tubing system.

Figure 3:
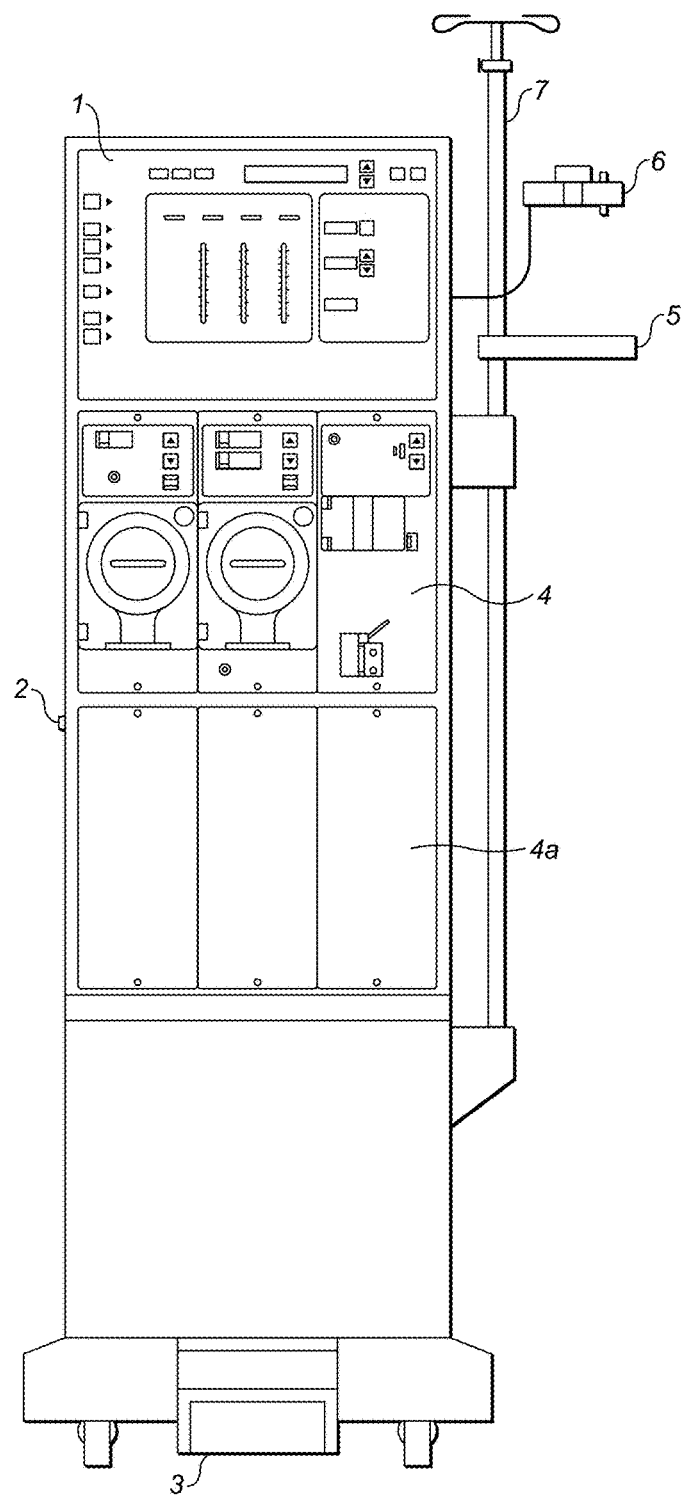
FIG. 3—The pump with air detector and optical detector (4).

A schematic diagram of the pump, showing the air detector and optical filter is shown in FIG. 3. If the pump system detects air bubbles and optical fluctuations or if extracorporeal pressure values are out of the set range, then the pump stops immediately and a visual/audible alarm are emitted.

Legend for FIG. 3:
1. Monitor
2. Holder for waste bag
3. Modules (left to right—Blood pump, ACD pump, Air detector)
4. Reserve places for further modules
5. Absorber holder
6. Drip detector
7. IV pole Preparation of the Patient The patient will be administered anticoagulants prior to each treatment session. A sterile saline solution with 5000 IE Heparin will be used for priming the extracorporeal system, thereafter a bolus injection with 4000 IE Heparin will be added into the circuit at the start of each treatment session.

Leukapheresis Time and Flow Rate

The apheresis system should be operated at a flow rate of 30-60 mL/min. A treatment is finalised after 1800 mL of blood has been circulated.

Storage Conditions

The column devices should be stored between 1 and 25° C. avoiding freezing and more elevated temperatures. Stability data >3 months indicate no difference in functionality over time or by temperature (room temperature and refrigerated). The columns will be kept in refrigerated conditions until use. Mechanical damage as those resulting from violent vibrations and trauma should be avoided. Column stored outside of these recommendations should not be used.

Transport Conditions

The column devices will be transported under refrigerated condition, avoiding freezing and more elevated temperatures. Mechanical damage such as those resulting from violent vibrations and trauma should be avoided.

In-Vitro Depletion of Target Cell Populations

To investigate the ability to eliminate CCR6-expressing cells, in vitro tests have been performed on the biotinylated MIP-3alpha coupled matrix. Blood was collected from blood donors and passed through the column device containing biotinylated MIP-3alpha coupled matrix. Blood samples were taken before and after column passage and analyzed by flow cytometry (FACS) for the depletion of CCR6-expressing cells.

Figure 4:
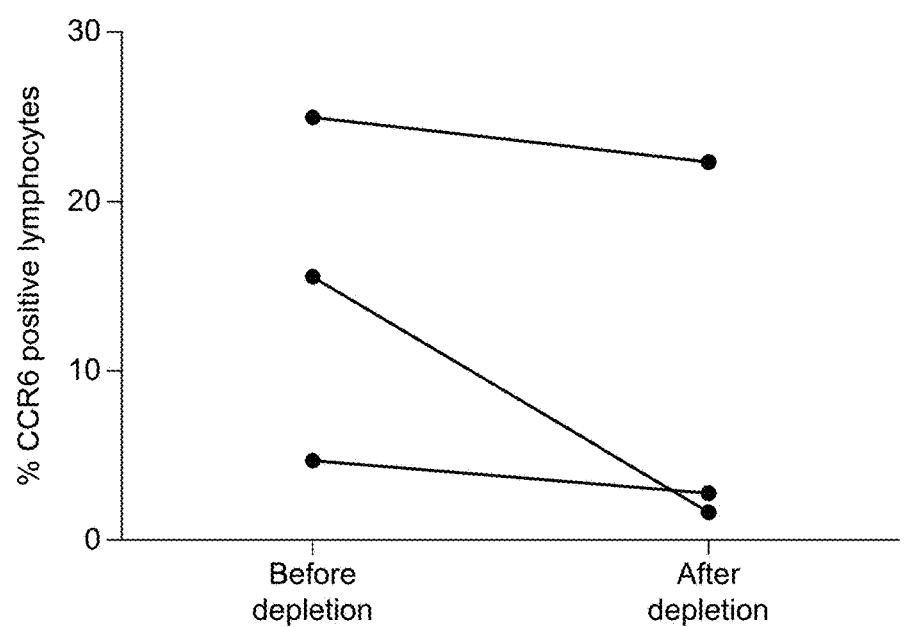
FIG. 4—Results of in vitro depletion tests performed on the biotinylated MIP-3alpha coupled matrix showing ability to eliminate CCR6-expressing lymphocytes from blood from three healthy donors.
Figure 5:
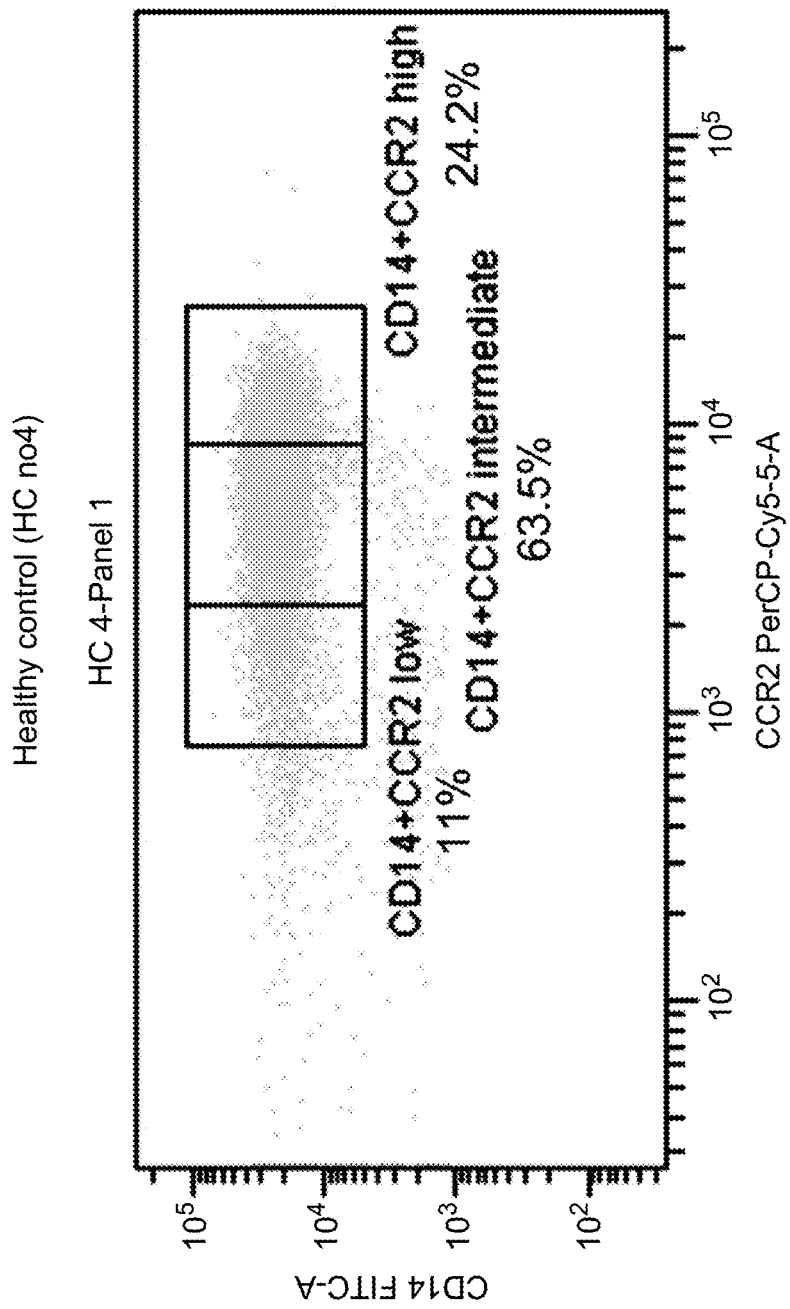
FIG. 5—Example of gating criteria for CCR2 expressing monocytes

The results demonstrate significant depletion of the target population CCR6-expressing lymphocytes post matrix perfusion. Depletion tests were performed on blood from three healthy donors. The results are shown in FIG. 4.

The in-vitro results demonstrate a specific reduction of up to around 15% of the CCR6-expressing cells by the column. Non-CCR6-expressing cells remained unaffected (data not shown).

Example 2A—Treatment of Chronic Lymphatic Leukemia (CLL) Patient

Materials and Methods

1. Flow Cytometric Analysis of Peripheral Blood

Peripheral blood from patients and healthy controls was collected in heparin tubes. The red blood cells were lysed using Fix Buffer (Phosphate Buffer Saline (PBS) citrate with 4% paraformaldehyde) for four minutes at 37° C. and Lysing buffer (PBS with 10 mM Tris and 160 mM NH4Cl, pH 7.5) for 15 min at 37° C. The cells were washed in PBS with 2% Bovine Growth Serum, incubated with 10% human serum for 15 min at room temperature (RD and stained with antibodies (Table 2) at 4° C. for 30 min. The cells were analysed by flow cytometry on a FACS Canto flow cytometer with the FACSDiva software (BD Biosciences).

TABLE 2

List of antibodies for flow cytometric analysis.

| Antibody | Fluorophore | Supplier |
| --- | --- | --- |
| CD14 | FITC | Beckman Coulter |
| Streptavidin | PE, APC | Biolegend |
| CCR7 | PerCP Cy5.5 | Biolegend |
| CD16 | PE Cy7 | BD Biosciences |
| CD3 | V450 | BD Biosciences |
| CD19 | V500 | BD Biosciences |

2. Chemokine Binding Test

Peripheral blood from patients and healthy controls was collected in heparin tubes. The red blood cells were lysed using Fix Buffer (Phosphate Buffer Saline (PBS) citrate with 4% paraformaldehyde) for four minutes at 37° C. and Lysing buffer (PBS with 10 mM Tris and 160 mM NH4Cl, pH 7.5) for 15 min at 37° C. The cells were washed in PBS with 2% Bovine Growth Serum, incubated with 10% human serum for 15 min at room temperature (RD and stained with cell specific antibodies together with biotinylated chemokine (1 µM) or the corresponding chemokine receptor antibody at 4° C. for 30 min (Table 2). The biotinylated chemokine was detected via the interaction between biotin and a fluorophore conjugated Streptavidin. The samples were analysed by flow cytometry on a FACS Canto flow cytometer with the FACSDiva software (BD Biosciences).

3. Cell Depletion By Matrix Conjugated with Biotinylated Chemokine

Cells were prepared from peripheral blood (section 1). 1 mL Sepharose BigBeads matrix conjugated with 0.4 mg/mL Streptavidin (GE Healthcare) was washed in 50 mL PBS and added to a 5 mL polystyrene tube (BD Falcon™). Biotinylated chemokine (1 µM) was added to the tube and incubated for 20 min at RT to enable immobilization of the chemokine on the matrix via the biotin-streptavidin interaction. Next, the cells were added to the chemokine-matrix and incubated for 20 min at RT. The cells that did not bind to the matrix were removed by washing the matrix with PBS in a sterile 40 µm nylon filter (BD Falcon™ Cell Strainer). The flow through cells were stained with antibodies (Table 2), analysed by flow cytometry and compared with cells from peripheral blood that had not been incubated with the chemokine-matrix.

Results and Discussion

1. Flow Cytometric Analysis of Peripheral Blood

Figure 6:
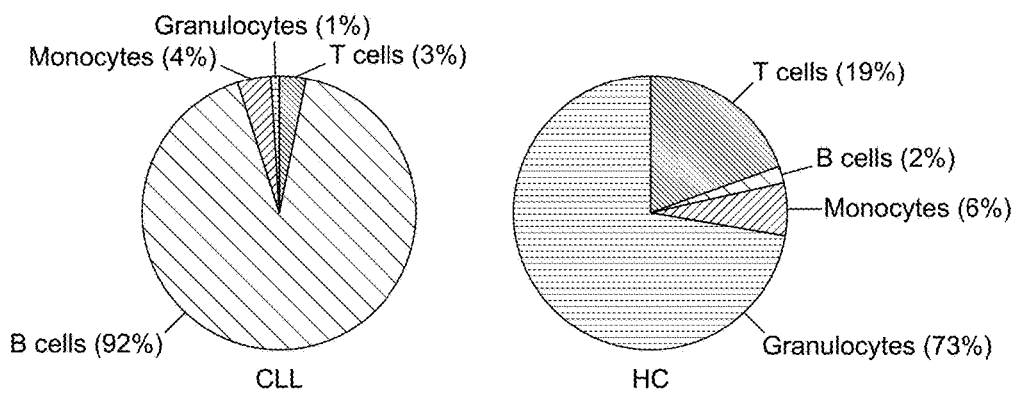
FIG. 6—Percentage of different leukocyte populations in a patient with Chronic Lymphatic Leukemia and in a healthy control (HC). Blood from a patient with CLL and a healthy control were analysed for the expression of cell specific markers with flow cytometry. The B cells were characterized as CD19 positive, the T cells as CD3 positive, granulocytes as CD16 positive and monocytes as CD14 positive.

White blood cells from a CLL patient were analysed by flow cytometry. The patient had a highly increased number of circulating B cells; 92% compared to approximately 2% in healthy blood (FIG. 6). This finding is common in CLL where malignant B cells undergo extensive proliferation, accumulate in the bone marrow and blood and crowd out healthy blood cells.

2. Chemokine Binding Test

Figure 7:
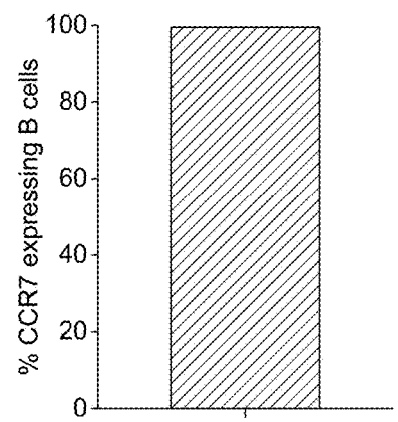
FIG. 7—Expression of CCR7 on B cells from a patient with Chronic Lymphatic Leukemia. Blood from a patient with CCL was analysed for the expression of various chemokine receptors by flow cytometry. The B cells were characterized as CD19+ lymphocytes.
Figure 8:
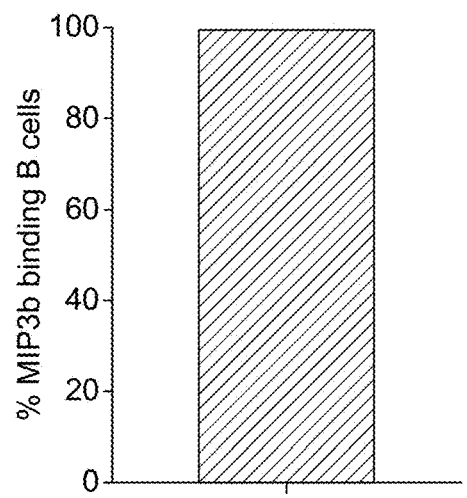
FIG. 8—Binding of the biotinylated chemokine MIP3b (CCL19) to B cells from a patient with Chronic Lymphatic Leukemia. Blood from a patient with CLL was incubated with bMIP3b and analysed by flow cytometry. The B cells were characterized as CD19+ lymphocytes.

All the B cells were shown to express the chemokine receptor CCR7 (FIG. 7) based upon flow cytometry data and binding by an anti-CCR7 antibody. CCR7 is important for lymph node homing which is mediated by binding to chemokines such as MIP3b (CCL19) and SLC (CCL21) that are expressed in lymphoid tissue. In accordance with the CCR7 expression, all the B cells bound to a biotinylated MIP3b (bMIP3b) (FIG. 8).

3. Cell Depletion By Matrix Conjugated with Biotinylated Chemokine

Figure 9:
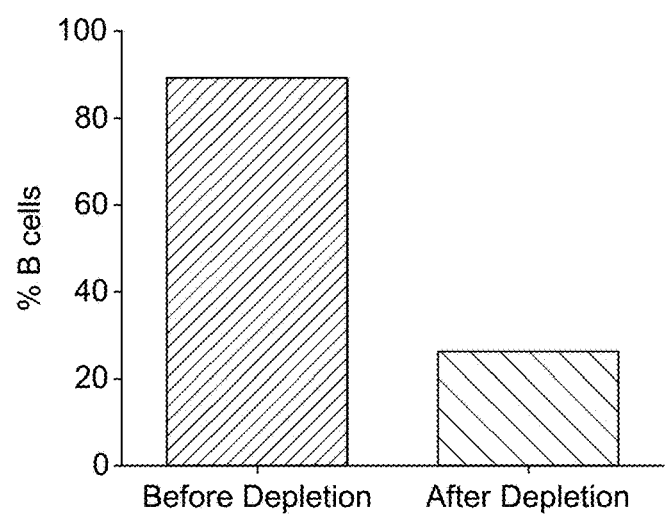
FIG. 9—Depletion of B cells with Sepharose Streptavidin matrix conjugated with bMIP3b. Blood cells from a patient with CLL were incubated with bMIP3b-SepharoseStreptavidin matrix. Unbound cells were retrieved by washing the matrix with Phosphate Buffer Saline. The cells (After Depletion) were then analysed by flow cytometry and compared with cells that had not been incubated with the MIP3b-matrix (Before Depletion).

The B cells were efficiently depleted using bMIP3b-conjugated Sepharose Streptavidin Matrix. Before depletion the B cells constituted 89.1% of the cells and after depletion 26.4% (FIG. 9).

We conclude that B cells in CLL express CCR7 and bind the ligand bMIP3b. Furthermore the majority (62.7%) of the CCR7 expressing B cells can be removed using a Sepharose Streptavidin matrix conjugated with bMIP3b.

Example 2B—Treatment of Cancers Via Removal of CCR4 Expressing Tregs Using Biotinylated-MDC (CCL22)

Materials and Methods

1. Flow Cytometric Analysis of Peripheral Blood

Peripheral blood from patients and healthy controls was collected in heparin tubes. The red blood cells were lysed using Fix Buffer (Phosphate Buffer Saline (PBS) citrate with 4% paraformaldehyde) for four minutes at 37° C. and Lysing buffer (PBS with 10 mM Tris and 160 mM NH$_4$Cl, pH 7.5) for 15 min at 37° C. The cells were washed in PBS with 2% Bovine Growth Serum, incubated with 10% human serum for 15 min at room temperature (RD and stained with antibodies (Table 3) at 4° C. for 30 min. The cells were analysed by flow cytometry on a FACS Canto flow cytometer with the FACSDiva software (BD Biosciences).

TABLE 3

List of antibodies for flow cytometric analysis.

| Antibody | Fluorophore | Supplier |
| --- | --- | --- |
| CCR4 | PerCP Cy5.5 | BD Biosciences |
| CD127 | PE Cy7 | Biolegend |
| CD4 | V500 | Biolegend |
| CD25 | APCCy7 | Biolegend |
| CD3 | Pacific blue | BD Biosciences |
| Streptavdin | PerCpCy5.5 | BD Biosciences |
| CD25 | FITC | BD Biosciences |

2. Chemokine Binding Test

Peripheral blood from patients and healthy controls was collected in heparin tubes. The red blood cells were lysed using Fix Buffer (Phosphate Buffer Saline (PBS) citrate with 4% paraformaldehyde) for four minutes at 37° C. and Lysing buffer (PBS with 10 mM Tris and 160 mM NH4Cl, pH 7.5) for 15 min at 37° C. The cells were washed in PBS with 2% Bovine Growth Serum, incubated with 10% human serum 15 min at room temperature (RD and stained with cell specific antibodies together with biotinylated chemokine (1 µM) or the corresponding chemokine receptor antibody at 4° C. for 30 min (Table 3). The biotinylated chemokine was detected via the interaction between biotin and a fluorophore conjugated Streptavidin. The samples were analysed by flow cytometry on a FACS Canto flow cytometer with the FACSDiva software (BD Biosciences).

3. Cell Depletion By Matrix Conjugated with Biotinylated Chemokine

Cells were prepared from peripheral blood (section 1). 1 mL Sepharose BigBeads matrix conjugated with 0.4 mg/mL Streptavidin (GE Healthcare) was washed in 50 mL PBS and added to a 5 mL polystyrene tube (BD Falcon™). Biotinylated chemokine (1 µM) was added to the tube and incubated for 20 min at RT to enable immobilization of the chemokine on the matrix via the biotin-streptavidin interaction. Next, the cells were added to the chemokine-matrix and incubated for 20 min at RT. The cells that did not bind to the matrix were removed by washing the matrix with PBS in a sterile 40 um nylon filter (BD Falcon™ Cell Strainer). The flow through cells were stained with antibodies (Table 3), analysed by flow cytometry and compared with cells from peripheral blood that had not been incubated with the chemokine-matrix.

Results and Discussion

Figure 10:
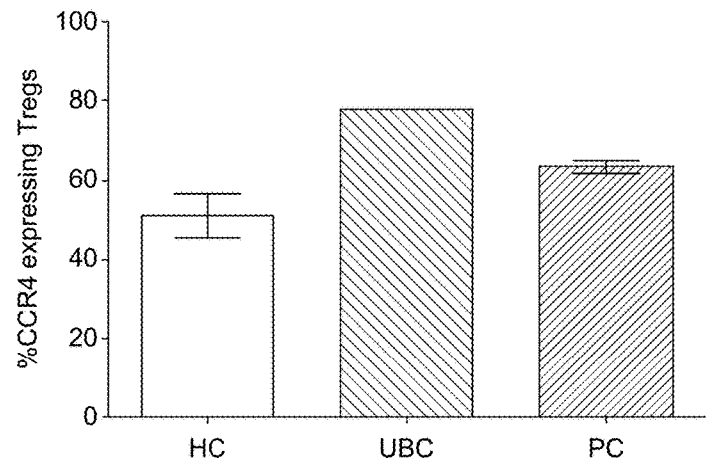
FIG. 10—Frequency of CCR4 positive Tregs in eight healthy controls (HC), two patients with Pancreatic Cancer (PC) and one patient with Urinary Bladder Cancer (UBC). The expression of chemokine receptors and specific cell markers was analyzed with flow cytometry. The Tregs were defined as CD4 positive, CD25 positive (hi), CD127 negative cells.

T regulatory cells (Tregs) are a subpopulation of T cells that suppress the immune system in order to maintain immune homeostasis. In cancer, the Tregs can inhibit an effective immune response against the tumor and thus removal of the Tregs could lead to a better immune activation against the cancer cells. White blood cells from patients with Urinary Bladder Cancer (UBC) and Pancreas Cancer (PC) were analyzed for the expression of chemokine receptors with flow cytometry. The cancer patients exhibited an increased frequency of circulating T regulatory cells (Tregs) that expressed the chemokine receptor CCR4, based upon flow cytometry data and binding by an anti-CCR4 antibody (FIG. 10).

Figure 11:
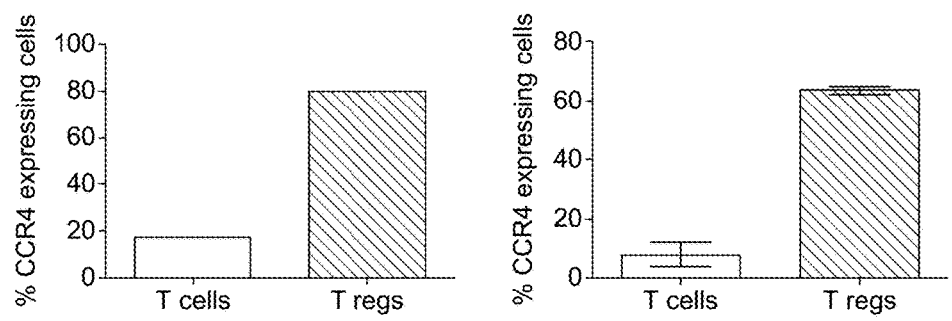
FIG. 11—CCR4 expression on Tregs compared to T cells in UBC (left) and PC (right). The expression of chemokine receptors and specific cell markers was analysed with flow cytometry in two patients with PC and one patient with UBC.

In both UBC and PC patients, CCR4 was highly upregulated on Tregs compared with the total T cell population (FIG. 11).

Figure 12:
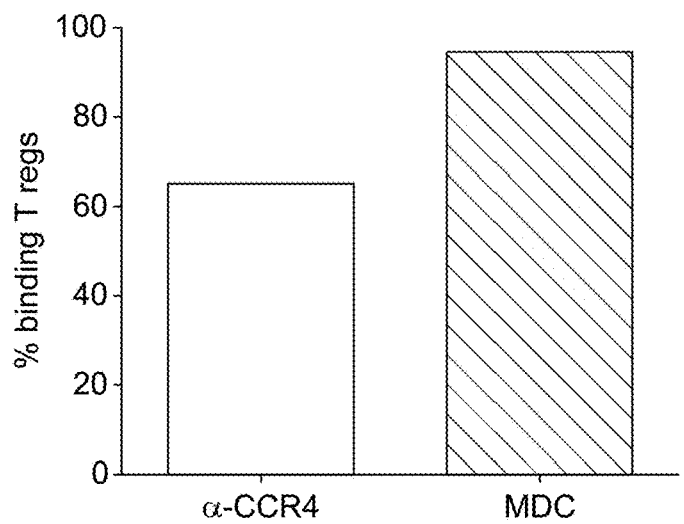
FIG. 12—Binding of the chemokine bMDC to Tregs. Blood cells from a patient with PC were incubated with biotinylated chemokine or an anti-CCR4 antibody and analyzed with flow cytometry.

The ligand for CCR4 is the chemokine MDC (CCL22). In accordance with the CCR4 expression, the Tregs bound to biotinylated MDC (bMDC) (FIG. 12).

Figure 13:
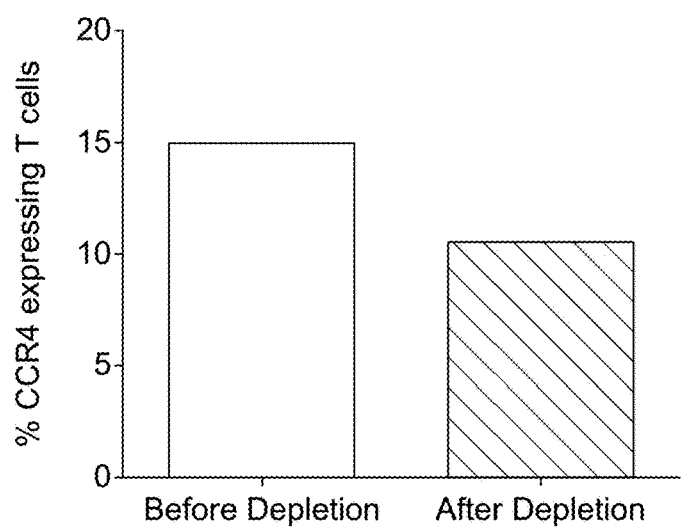
FIG. 13—Depletion of CCR4 expressing T cells with Sepharose Streptavidin-matrix conjugated with biotinylated MDC (bMDC). Blood cells from a patient with UBC were incubated with biotinylated chemokine-Sepharose Streptavidin-matrix. Unbound cells were retrieved by washing the matrix. The unbound cells (After Depletion) were then analysed with flow cytometry and compared with cells that had not been incubated with bchemokine-matrix (Before Depletion).

The CCR4 expressing T cells could be depleted with bMDC-conjugated Sepharose Streptavidin Matrix (FIG. 13).

We conclude that the frequency of Tregs that express CCR4 is enhanced in PC and UBC. These cells can bind the ligand bMDC. The Tregs express significantly more CCR4 than conventional T cells and can thus be specifically deleted with Sepharose Streptavidin matrix conjugated with bMDC.

Examples 3 to 10: General Protocols—Synthesis of Chemokines

Assembly:

Chemical synthesis of chemokines was performed using standard Fmoc solid phase peptides synthesis (SPPS) techniques on an ABI 433 peptide synthesiser. DIC (0.5 M in DMF) and OxymaPure (0.5 M in DMF) were used for activation, acetic anhydride (0.5 M in DMF) for capping, and 20% piperidine in DMF for Fmoc deprotection. Rink Amide resin was utilised for the generation of C-terminal amide chemokines and Wang resin for C-terminal acid chemokines. After assembly, the resin was washed with DMF and DCM and then dried in vacuo.

Removal of Dde Protection:

The Dde protecting group was removed by treatment of resin with a solution of 2.5% hydrazine in DMF (200 ml) over a 2 hour period. The resin was then washed with DMF.

Labelling Steps:

1. Couple Fmoc-8-amino-3,6-dioctanoic acid (PEG)

Resin was swollen in DMF and then a solution of Fmoc-8-amino-3,6-dioctanoic acid (0.38 g, 1 mmol), DIC solution (2 ml, 0.5 M in DMF) and OxymaPure solution (2 ml, 0.5 M in DMF) was added. The mixture was sonicated for 3 hours and then washed with DMF.

2. Capping

The resin was capped with acetic anhydride solution (0.5 M in DMF, 10 ml) for 5 minutes and then washed with DMF.

3. Fmoc deprotection

Fmoc deprotection was carried out by treatment with 20% piperidine in DMF solution (2×50 ml) for 15 minutes each. The resin was washed with DMF.

4. Couple Biotin-OSu

A solution of Biotin-OSu (341 mg, 1 mmol) and DIPEA (348 µl) in DMF (10 ml) was added to the resin and the mixture was sonicated for 3 hours. The resin was washed thoroughly with DMF and DCM then dried in vacuo.

Cleavage:

Dry resin was treated with TFA (10 ml) containing a scavenger cocktail consisting of TIS (500 µl) thioanisole (500 µl), water (500 µl), DMS (500 µl), EDT (250 µl), NH$_4$I (500 µg) and phenol (500 µg) and the mixture was stirred at room temperature for 5 hours. The solution was filtered into cold ether and the resin rinsed with TFA. The precipitated peptide was centrifuged, washed with ether, centrifuged and lyophilised.

Purification Protocol:

The crude peptide was purified by reverse phase HPLC (RP-HPLC) using a Jupiter C18, 250×21 mm column, 9 ml/min, eluting with an optimised gradient [Buffer A: water containing 0.1% TFA, Buffer B: acetonitrile containing 0.1% TFA].

Folding Protocol:

Pure peptide (10 mg) was dissolved into 6M GnHCl (16 ml) and then rapidly diluted to 2M GnHCl concentration by the addition of 50 mM TRIS pH 8.5 (84 ml) containing 0.3 mM GSSG and 3 mM GSH. The mixture was stirred at room temperature for 24 hours and then analysed by RP-HPLC (Jupiter C18, 250×4.6 mm column, 10-60% B over 30 minutes). Purification by RP-HPLC using an optimised gradient afforded the desired product.

Example 3—BiotinMCP-2 (CCL8)

Target Molecule: MCP-2 derivatised at the ε-amino side chain functionality of Lys(75) with PEG-Biotin (TFA salt)

Modifications: Human MCP-2 corresponding to residues 1-76, is initially expressed as 99 amino acids comprising the chemokine fold, and a 23 amino acid signal peptide which is cleaved off. The Gln at the N-terminus of the protein is subject to pyroGlu formation under physiological conditions. Thus Gln1 of the sequence was substituted with pyroglutamine to prevent mixed species of N-terminal Gln and pyroGlu being generated. This improves the yield of synthesis and ensures a homogeneous chemokine preparation through column manufacture and use. The naturally occurring lysine at position 75 was modified through biotinylation on the resin. A PEG spacer was incorporated between the ε-amino functionality and the biotin.

The linear amino acid sequence (SEQ ID NO: 1) is shown, prior to attachment of the PEG spacer and biotin molecules at amino acid 75 (K):

H-XPDSVSIPITCCFNVINRKIPIQRLESYTRITNIQCPKEAVIFKTKRG

KEVCADPKERWVRDSMKHLDQIFQNLXP-NH$_2$

X1=pyroGlu or Gln

X75=an amino acid residue that can be biotinylated, such as lysine, ornithine or diaminopropionic acid and optionally is biotinylated, optionally via a spacer molecule such as PEG, in particular K(PEG-Biotin)

The engineered MCP-2 sequence was assembled on a solid support (Rink Amide resin), using Fmoc protocols for solid-phase peptide synthesis as described in the general protocols section:

H-XPDSVSIPITCCFNVINRKIPIQRLESYTRITNIQCPKEAVIFKTKRG

KEVCADPKERWVRDSMKHLDQIFQNLXP-NH$_2$

X1=pyroGlu or Gln
X75=K(ivDde)

FmocLys(ivDde)-OH was incorporated as residue 75 to facilitate site-specific labelling at this position of the protein (SEQ ID NO: 2). Subsequent removal of the ivDde protecting group, followed by coupling of the PEG spacer and Biotin, was carried out as described in the general protocol section. Cleavage, purification and folding protocols were carried out as described to furnish the desired active chemokine (SEQ ID NO: 3).

H-XPDSVSIPITCCFNVINRKIPIQRLESYTRITNIQCPKEAVIFKTKR

GKEVCADPKERWVRDSMKHLDQIFQNLXP-NH$_2$

X1=pyroGlu or Gln
X75=K(PEG-Biotin)

Electrospray ionisation with tandem mass spectrometry (ESI-TOF-MS) data of purified folded biotinMCP-2: obtained=9263.6 Da; expected 9263.8 Da.

Functional Assay Data:

biotinMCP-2 was tested for activity in an Aequorin assay against hCCR2b, (Euroscreen) and was shown to be a partial agonist with an EC50 value of 50.9 nM. c.f. EC50 for recombinant native MCP-2 is 23.5 nM (partial agonist).

Example 4—BiotinRANTES (CCL5)

Target Molecule: RANTES derivatised at the ε-amino side chain functionality of Lys(67) with Biotin (TFA salt)

Modifications: Human RANTES corresponding to residues 1-68, is initially expressed as 91 amino acids comprising the chemokine fold, and a 23 amino acid signal peptide which is cleaved off. The single methionine (Met67) within the sequence was mutated to lysine, to mitigate against oxidation of this residue during the chain assembly, which was observed during the synthesis of the natural sequence derivative. This Met to Lys substitution provided a lysine at position 67 which was modified through biotinylation on the resin.

The linear amino acid sequence (SEQ ID NO: 4) is shown, prior to attachment of the biotin molecule at amino acid 67 (K):

H-SPYSSDTTPCCFAYIARPLPRAHIKEYFYTSGKCSNPAVVFVTRKNR

QVCANPEKKWVREYINSLEKS-OH

The engineered RANTES sequence was assembled on a solid support (Wang resin), using Fmoc protocols for solid-phase peptide synthesis as described in the general protocols section:

H-SPYSSDTTPCCFAYIARPLPRAHIKEYFYTSGKCSNPAVVFVTRKNR

QVCANPEKKWVREYINSLEXS-RESIN

X=K(ivDde)

FmocLys(ivDde)-OH was incorporated as residue 67 to facilitate site-specific labelling at this position of the protein (SEQ ID NO: 5). Subsequent removal of the ivDde protecting group, followed by coupling of the Biotin, was carried out as described in the general protocol section. Cleavage, purification and folding protocols were carried out as described to furnish the desired active chemokine (SEQ ID NO: 6).

H-SPYSSDTTPCCFAYIARPLPRAHIKEYFYTSGKCSNPAVVFVTRKNR

QVCANPEKKWVREYINSLEXS-OH

X is an amino acid residue that can be biotinylated, such as lysine, ornithine or diaminopropionic acid and optionally is biotinylated (e.g. K-biotin), optionally via a spacer molecule such as PEG, in particular K(PEG-Biotin)

Electrospray ionisation with tandem mass spectrometry (ESI-TOF-MS) data of purified folded biotinRANTES: obtained=8068.9 Da; expected 8070.2 Da.

Functional Assay Data:

BiotinRANTES was tested for agonist activity in an Aequorin assay against hCCR5, (Euroscreen) and an EC50 value of 0.5 nM was reported.

Example 5—BiotinMIP-3α (CCL20)

Target Molecule: MIP-3a derivatised at the s-amino side chain functionality of Lys(68) with PEG-Biotin (TFA salt)

Modifications: Human MIP-3a corresponding to residues 1-70, is initially expressed as 96 amino acids comprising the chemokine fold, and a 26 amino acid signal peptide which is cleaved off. The naturally occurring lysine at position 68 was modified through biotinylation on the resin. A PEG spacer was incorporated between the ε-amino functionality and the biotin.

The linear amino acid sequence (SEQ ID NO: 7) is shown, prior to attachment of the PEG spacer and biotin molecules at amino acid 68 (K):

H-ASNFDCCLGYTDRILHPKFIVGFTRQLANEGCDINAIIFHTKKKLSV

CANPKQTWVKYIVRLLSKKVKNM-OH

The engineered MIP-3a sequence was assembled on a solid support (Wang resin), using Fmoc protocols for solid-phase peptide synthesis as described in the general protocols section:

H-ASNFDCCLGYTDRILHPKFIVGFTRQLANEGCDINAIIFHTKKKLSV

CANPKQTWVKYIVRLLSKKVXNM-RESIN

X=K(ivDde)

FmocLys(ivDde)-OH was incorporated as residue 68 to facilitate site-specific labelling at this position of the protein (SEQ ID NO: 8). Subsequent removal of the ivDde protecting group, followed by coupling of the PEG spacer and Biotin, was carried out as described in the general protocol section. Cleavage, purification and folding protocols were carried out as described to furnish the desired active chemokine (SEQ ID NO: 9).

H-ASNFDCCLGYTDRILHPKFIVGFTRQLANEGCDINAIIFHTKKKLSV

CANPKQTWVKYIVRLLSKKVXNM-OH

X is an amino acid residue that can be biotinylated, such as lysine, ornithine or diaminopropionic acid and optionally is biotinylated, optionally via a spacer molecule such as PEG, in particular K(PEG-Biotin)

Electrospray ionisation with tandem mass spectrometry (ESI-TOF-MS) data of purified folded biotinMip-3α: obtained=8396.4 Da; expected 8397.0 Da.

Functional Assay Data:

BiotinMIP-3α was tested for agonist activity in an Aequorin assay against hCCR6, (Euroscreen) and an EC50 value of 1.6 nM was reported. c.f. EC50 for recombinant native MIP-3α is 1.0 nM.

Example 6—BiotinSDF-1α (CXCL12)

Target Molecule: SDF-1α derivatised at the s-amino side chain functionality of Lys(64) with Biotin (TFA salt)

Modifications: Truncated form of human SDF-1a corresponding to residues 1-67 of the mature protein, which encompasses the sequence corresponding to the chemokine fold. The full length mature protein is 72 amino acids (the signal peptide is 21 amino acids in a 93 amino acid immature protein). The naturally occurring lysine at position 64 was modified through biotinylation on the resin.

The linear amino acid sequence (SEQ ID NO: 10) is shown, prior to attachment of the biotin molecule at amino acid 64 (K):

H-KPVSLSYRCPCRFFESHVARANVKHLKILNTPNCALQIVARLKNNNR

```
QVCIDPKLKWIQEYLEKALN-OH
```

The engineered SDF-1α sequence was assembled on a solid support (Wang resin), using Fmoc protocols for solid-phase peptide synthesis as described in the general protocols section:

```
H-KPVSLSYRCPCRFFESHVARANVKHLKILNTPNCALQIVARLKNNNR

QVCIDPKLKWIQEYLEKXALN-RESIN
```

X=K(ivDde)

FmocLys(ivDde)-OH was incorporated as residue 64 to facilitate site-specific labelling at this position of the protein (SEQ ID NO: 11). Subsequent removal of the ivDde protecting group, followed by coupling of the Biotin, was carried out as described in the general protocol section. Cleavage, purification and folding protocols were carried out as described to furnish the desired active chemokine (SEQ ID NO: 12).

```
H-KPVSLSYRCPCRFFESHVARANVKHLKILNTPNCALQIVARLKNNNR

QVCIDPKLKWIQEYLEXALN-OH
```

X is an amino acid residue that can be biotinylated, such as lysine, ornithine or diaminopropionic acid and optionally is biotinylated, optionally via a spacer molecule such as PEG, especially K(Biotin)

Electrospray ionisation with tandem mass spectrometry (ESI-TOF-MS) data of purified folded biotinSDF-1α: obtained =8055.5 Da; expected 8057.5 Da.

Functional Assay Data:

biotinSDF-1α was tested for agonist activity in an Aequorin assay against hCXCR4, (Euroscreen) and an EC50 value of 17.3 nM was reported. c.f. EC50 for recombinant native SDF-1α is 12.0 nM.

Example 7—BiotinMDC (CCL22)

Target Molecule: MDC derivatised at the ε-amino side chain functionality of Lys(66) with PEG-Biotin (TFA salt)

Modifications: Human MDC corresponding to residues 1-69, is initially expressed as 93 amino acids comprising the chemokine fold, and a 24 amino acid signal peptide which is cleaved off. The naturally occurring lysine at position 66 was modified through biotinylation on the resin. A PEG spacer was incorporated between the ε-amino functionality and the biotin.

The linear amino acid sequence (SEQ ID NO: 13) is shown, prior to attachment of the PEG spacer and biotin molecules at amino acid 66 (K):

```
H-GPYGANMEDSVCCRDYVRYRLPLRVVKHFYWTSDSCPRPGVVLLTFR

DKEICADPRVPWVKMILNKLSQ-NH₂
```

The engineered MDC sequence was assembled on a solid support (Rink Amide resin), using Fmoc protocols for solid-phase peptide synthesis as described in the general protocols section:

```
H-GPYGANMEDSVCCRDYVRYRLPLRVVKHFYWTSDSCPRPGVVLLTFR

DKEICADPRVPWVKMILNXLSQ-RESIN
```

X=K(ivDde)

FmocLys(ivDde)-OH was incorporated as residue 66 to facilitate site-specific labelling at this position of the protein (SEQ ID NO: 14). Subsequent removal of the ivDde protecting group, followed by coupling of the PEG spacer and Biotin, was carried out as described in the general protocol section. Cleavage, purification and folding protocols were carried out as described to furnish the desired active chemokine (SEQ ID NO: 15).

```
H-GPYGANMEDSVCCRDYVRYRLPLRVVKHFYWTSDSCPRPGVVLLTFR

DKEICADPRVPWVKMILNXLSQ-NH₂
```

X is an amino acid residue that can be biotinylated, such as lysine, ornithine or diaminopropionic acid and optionally is biotinylated, optionally via a spacer molecule such as PEG, especially K(PEG-Biotin)

Electrospray ionisation with tandem mass spectrometry (ESI-TOF-MS) data of purified folded biotinMDC: obtained =8456.1 Da; expected 8456.9 Da.

Functional Assay Data:

BiotinMDC was tested for agonist activity in an Aequorin assay against hCCR4, (Euroscreen) and an EC50 value of 4.5 nM was reported. c.f. EC50 for recombinant native MDC is 3.6 nM.

Example 8—BiotinTARC (CCL17)

Target Molecule: TARC derivatised at the s-amino side chain functionality of Lys(72) with PEG-Biotin (TFA salt)

Modifications: Human TARC corresponding to residues 1-71, is initially expressed as 94 amino acids comprising the chemokine fold, and a 23 amino acid signal peptide which is cleaved off. An additional lysine was inserted at the C-terminus, at position 72, and modified through biotinylation on the resin. A PEG spacer was incorporated between the ε-amino functionality and the biotin.

The linear amino acid sequence (SEQ ID NO: 16) is shown, prior to attachment of the PEG spacer and biotin molecules at amino acid 72 (K):

```
H-ARGTNVGRECCLEYFKGAIPLRKLKTWYQTSEDCSRDAIVFVTVQGR

AICSDPNNKRVKNAVKYLQSLERSX-NH₂
```

X is an amino acid residue that can be biotinylated, such as lysine, ornithine or diaminopropionic acid and optionally is biotinylated (e.g. K-biotin), optionally via a spacer molecule such as PEG, in particular K(PEG-Biotin)

The engineered TARC sequence was assembled on a solid support (Rink Amide resin), using Fmoc protocols for solid-phase peptide synthesis as described in the general protocols section:

```
H-ARGTNVGRECCLEYFKGAIPLRKLKTWYQTSEDCSRDAIVFVTVQG

RAICSDPNNKRVKNAVKYLQSLERSX-RESIN
```

X=K(ivDde)

FmocLys(ivDde)-OH was incorporated as residue 72 to facilitate site-specific labelling at this position of the protein (SEQ ID NO: 17). Subsequent removal of the ivDde protecting group, followed by coupling of the PEG spacer and Biotin, was carried out as described in the general protocol section. Cleavage, purification and folding protocols were carried out as described to furnish the desired active chemokine (SEQ ID NO: 18).

H-ARGTNVGRECCLEYFKGAIPLRKLKTWYQTSEDCSRDAIVFVTVQG

RAICSDPNNKRVKNAVKYLQSLERSX-NH$_2$

X=K(PEG-Biotin)

Electrospray ionisation with tandem mass spectrometry (ESI-TOF-MS) data of purified folded biotinTARC: obtained=8577.2 Da; expected 8577.8 Da.

Functional Assay Data:

BiotinTARC was tested for agonist activity in an Aequorin assay against hCCR4, (Euroscreen) and an EC50 value of 3.1 nM was reported. c.f. EC50 for recombinant native TARC is 2.6 nM.

Example 9—BiotinMIP-3β (CCL19)

Target Molecule: MIP-3β derivatised at the ε-amino side chain functionality of Lys(78) with Biotin (TFA salt)

Modifications: Human MIP-3β corresponding to residues 1-77, is initially expressed as 98 amino acids comprising the chemokine fold, and a 21 amino acid signal peptide which is cleaved off. An additional lysine was inserted at the C-terminus, at position 78, and modified through biotinylation on the resin.

The linear amino acid sequence (SEQ ID NO: 19) is shown, prior to attachment of the biotin molecule at amino acid 78 (K):

H-GTNDAEDCCLSVTQKPIPGYIVRNFHYLLIKDGCRVPAVVFTTLRGRQ

LCAPPDQPWVERIIQRLQRTSAKMKRRSSX-NH$_2$

X is an amino acid residue that can be biotinylated, such as lysine, ornithine or diaminopropionic acid and optionally is biotinylated (e.g. K-biotin), optionally via a spacer molecule such as PEG, in particular K(PEG-Biotin)

The engineered MIP-3β sequence was assembled on a solid support (Rink Amide resin), using Fmoc protocols for solid-phase peptide synthesis as described in the general protocols section:

H-GTNDAEDCCLSVTQKPIPGYIVRNFHYLLIKDGCRVPAVVFTTLRGRQ

LCAPPDQPWVERIIQRLQRTSAKMKRRSSX-RESIN

X is FmocLys(ivDde)

FmocLys(ivDde)-OH was incorporated as residue 78 to facilitate site-specific labelling at this position of the protein (SEQ ID NO: 20). Subsequent removal of the ivDde protecting group, followed by coupling of the Biotin, was carried out as described in the general protocol section. Cleavage, purification and folding protocols were carried out as described to furnish the desired active chemokine (SEQ ID NO: 21).

H-GTNDAEDCCLSVTQKPIPGYIVRNFHYLLIKDGCRVPAVVFTTLRGRQ

LCAPPDQPWVERIIQRLQRTSAKMKRRSSX-NH$_2$

X is K(Biotin)

Electrospray ionisation with tandem mass spectrometry (ESI-TOF-MS) data of purified folded biotinMIP-3β: obtained=9148.8 Da; expected 9149.7 Da.

Functional Assay Data:

biotinMip-3β was tested for agonist activity in an Aequorin assay against hCCR7, (Euroscreen) and an EC50 value of 11.0 nM was reported. c.f. EC50 for recombinant native MIP-3β is 1.6 nM.

Example 10—BiotinITAC (CXCL11)

Target Molecule: ITAC derivatised with Biotin at the ε-amino side chain functionality of an additional Lysine inserted at the C-terminus after a PEG spacer (TFA salt)

Modifications: Human ITAC corresponding to residues 1-73, is initially expressed as 94 amino acids comprising the chemokine fold, and a 21 amino acid signal peptide which is cleaved off. A PEG spacer and an additional lysine were inserted at the C-terminus, and modified through biotinylation on the resin. The PEG spacer was incorporated at the C-terminus between the protein and the additional lysine.

The linear amino acid sequence (SEQ ID NO: 22) is shown, prior to attachment of the PEG spacer, additional lysine and biotin molecules:

H-FPMFKRGRCLCIGPGVKAVKVADIEKASIMYPSNNCDKIEVIITLKEN

KGQRCLNPKSKQARLIIKKVERKNF-OH

The engineered ITAC sequence was assembled on a solid support (Wang resin), using Fmoc protocols for solid-phase peptide synthesis as described in the general protocols section:

H-FPMFKRGRCLCIGPGVKAVKVADIEKASIMYPSNNCDKIEVIITLKEN

KGQRCLNPKSKQARLIIKKVERKNFX-RESIN

X is PEG-K(ivDde)

Fmoc-12-amino-4,7,10-trioxadodecanoic acid followed by FmocLys(ivDde)-OH were incorporated at the C-terminus to facilitate site-specific labelling with biotin at the ε-amino side chain functionality of the additional Lys (SEQ ID NO: 24). Subsequent removal of the ivDde protecting group, followed by coupling of the Biotin, was carried out as described in the general protocol section. Cleavage, purification and folding protocols were carried out as described to furnish the desired active chemokine (SEQ ID NO: 25).

H-FPMFKRGRCLCIGPGVKAVKVADIEKASIMYPSNNCDKIEVIITLKEN

KGQRCLNPKSKQARLIIKKVERKNFX-OH

X is PEG-K(Biotin)

Electrospray ionisation with tandem mass spectrometry (ESI-TOF-MS) data of purified folded biotinITAC: obtained=8866.5 Da; expected 8860.6 Da.

Functional Assay Data:

biotinITAC was tested for agonist activity in an Aequorin assay against hCXCR3, (Euroscreen) and an EC50 value of 15.7 nM was reported. c.f. EC50 for recombinant native ITAC is 0.7 nM.

Example 11—BiotinTECK (CCL25)

Target Molecule: TECK (Met to Nleu substitution) derivatised at the ε-amino side chain functionality of Lys72 with PEG-Biotin (TFA salt)

Modifications: Truncated form of human TECK corresponding to residues 1-74 of the mature protein, which encompasses the sequence corresponding to the chemokine fold. The full length mature protein is 127 amino acids (the signal peptide is 23 amino acids in a 150 amino acid immature protein). The single methionine within the sequence was altered to Norleucine, to mitigate against oxidation of this residue during the chain assembly, which was observed during the synthesis of the natural sequence derivative. The Gln at the N-terminus of the proteins is subject to pyroGlu formation under physiological conditions. Thus Gln1 of the sequence was substituted with pyroglutamine to prevent mixed species of N-terminal Gln and pyroGlu being generated. This improves the yield of synthesis and ensures a homogeneous chemokine preparation through column manufacture and use. The naturally occurring lysine at position 72 was modified through biotinylation on the resin. A PEG spacer was incorporated between the ε-amino functionality and the biotin.

The linear amino acid sequence (SEQ ID NO: 26) is shown, prior to attachment of the PEG spacer and biotin molecules at amino acid 72 (K):

H-XGVFEDCCLAYHYPIGWAVLRRAWTYRIQEVSGSCNLPAAIFYLPKRH

RKVCGNPKSREVQRAXKLLDARNXVF-OH

X1=pyroGlu or Gln
X64=Norleucine
X72=an amino acid residue that can be biotinylated, such as lysine, ornithine or diaminopropionic acid and optionally is biotinylated, optionally via a spacer molecule such as PEG, e.g. K(PEG-Biotin)

The engineered TECK sequence was assembled on a solid support (Wang resin), using Fmoc protocols for solid-phase peptide synthesis as described in the general protocols section:

H-XGVFEDCCLAYHYPIGWAVLRRAWTYRIQEVSGSCNLPAAIFYLPKRH

RKVCGNPKSREVQRAXKLLDARNXVF-RESIN

X1=pyroGlu or Gln
X64=Norleucine
X72=K(ivDde)

FmocLys(ivDde)-OH was incorporated as residue 72 to facilitate site-specific labelling at this position of the protein (SEQ ID NO: 27). Subsequent removal of the ivDde protecting group, followed by coupling of the PEG spacer and Biotin, was carried out as described in the general protocol section. Cleavage, purification and folding protocols were carried out as described to furnish the desired active chemokine (SEQ ID NO: 28).

H-XGVFEDCCLAYHYPIGWAVLRRAWTYRIQEVSGSCNLPAAIFYLPKRH

RKVCGNPKSREVQRAXKLLDARNXVF-OH

X1=pyroGlu or Gln
X64=Norleucine
X72 is K(PEG-Biotin)

Electrospray ionisation with tandem mass spectrometry (ESI-TOF-MS) data of purified folded biotinTECK(Met to Nleu substitution): obtained=8958.5 Da; expected 8959.6 Da.

Functional Assay Data:
biotinTECK(Met to Nleu substitution) was tested for agonist activity in an Aequorin assay against hCCR9, (Euroscreen) and an EC50 value of 63.6 nM was reported. c.f. EC50 for recombinant native TECK is 67.9 nM.

Example 12—BiotinCTAC (CCL27)

Target Molecule: CTAC derivatised at the ε-amino side chain functionality of Lys(87) with PEG-Biotin (TFA salt)

Modifications: Human CTAC corresponding to residues 1-88, is initially expressed as 112 amino acids comprising the chemokine fold, and a 24 amino acid signal peptide which is cleaved off. The Met(87) within the sequence was mutated to lysine to provide a lysine at position 87 which was modified through biotinylation on the resin. A PEG spacer was incorporated between the ε-amino functionality and the biotin.

The linear amino acid sequence (SEQ ID NO: 29) is shown, prior to attachment of the PEG spacer and biotin molecules:

FLLPPSTACCTQLYRKPLSDKLLRKVIQVELQEADGDCHLQAFVLHLAQR

SICIHPQNPSLSQWFEHQERKLHGTLPKLNFGMLRKXG

X is an amino acid residue that can be biotinylated, such as lysine, ornithine or diaminopropionic acid and optionally is biotinylated, optionally via a spacer molecule such as PEG, e.g. K(PEG-Biotin)

The engineered CTAC sequence was assembled on a solid support (Wang resin), using Fmoc protocols for solid-phase peptide synthesis as described in the general protocols section:

H-FLLPPSTACCTQLYRKPLSDKLLRKVIQVELQEADGDCHLQAFVLHLA

QRSICIHPQNPSLSQWFEHQERKLHGTLPKLNFGMLRKXG-RESIN

X=K(ivDde)

FmocLys(ivDde)-OH was incorporated as residue 87 to facilitate site-specific labelling at this position of the protein (SEQ ID NO: 30). Subsequent removal of the ivDde protecting group, followed by coupling of the PEG spacer and Biotin, was carried out as described in the general protocol section. Cleavage, purification and folding protocols were carried out as described to furnish the desired active chemokine (SEQ ID NO: 31).

H-FLLPPSTACCTQLYRKPLSDKLLRKVIQVELQEADGDCHLQAFVLHLA

QRSICIHPQNPSLSQWFEHQERKLHGTLPKLNFGMLRKXG-OH

X=K(PEG-Biotin)

Electrospray ionisation with tandem mass spectrometry (ESI-TOF-MS) data of purified folded biotinCTAC: obtained=10513.4 Da; expected 10514.2 Da.

Functional Assay Data:
BiotinCTAC was tested for agonist activity in an Aequorin assay against hCCR10, (Euroscreen) and an EC50 value of 49.4 nM was reported. c.f. EC50 for recombinant native CTAC is 33.5 nM.

Example 13—BiotinIP-10 (CXCL10)

Target Molecule: IP-10 derivatised with Biotin at the ε-amino side chain functionality of an additional Lysine inserted at the C-terminus after a PEG spacer (TFA salt)

Modifications: Human IP-10 corresponding to residues 1-77, is initially expressed as 98 amino acids comprising the chemokine fold, and a 21 amino acid signal peptide which is cleaved off. A PEG spacer and an additional lysine were inserted at the C-terminus, and modified through biotinylation on the resin. The PEG spacer was incorporated at the C-terminus between the protein and the additional lysine.

The linear amino acid sequence (SEQ ID NO: 32) is shown, prior to attachment of the PEG spacer, additional lysine and biotin molecules:

H-VPLSRTVRCTCISISNQPVNPRSLEKLEIIPASQFCPRVEIIATMKKK

GEKRCLNPESKAIKNLLKAVSKERSKRSP-OH

The engineered IP-10 sequence was assembled on a solid support (Wang resin), using Fmoc protocols for solid-phase peptide synthesis as described in the general protocols section:

H-VPLSRTVRCTCISISNQPVNPRSLEKLEIIPASQFCPRVEIIATMKKK

GEKRCLNPESKAIKNLLKAVSKERSKRSPX-RESIN

X is K(ivDde), optionally attached via a spacer such as PEG, e.g. -PEG-K(ivDde)

Fmoc-8-amino-3,6-dioctanoic acid followed by FmocLys(ivDde)-OH were incorporated at the C-terminus to facilitate site-specific labelling with biotin at the ε-amino side chain functionality of the additional Lys (SEQ ID NO: 33). Subsequent removal of the ivDde protecting group, followed by coupling of the Biotin, was carried out as described in the general protocol section. Cleavage, purification and folding protocols were carried out as described to furnish the desired active chemokine. The final active chemokine thus has the following sequence (SEQ ID NO: 34):

H-VPLSRTVRCTCISISNQPVNPRSLEKLEIIPASQFCPRVEIIATMKKK

GEKRCLNPESKAIKNLLKAVSKERSKRSPX-OH

X is an amino acid residue that can be biotinylated, such as lysine, ornithine or diaminopropionic acid and optionally is biotinylated, optionally via a spacer molecule such as PEG, e.g. K(PEG-Biotin) and may be attached via a spacer molecule, e.g.PEG-K(Biotin)

Electrospray ionisation with tandem mass spectrometry (ESI-TOF-MS) data of purified folded biotinIP-10: obtained=9141.0 Da; expected 9141.9 Da.

Functional Assay Data:

BiotinIP-10 was tested for agonist activity in an Aequorin assay against hCXCR3, (Euroscreen) and an EC50 value of 8.7 nM was reported. c.f. EC50 for recombinant native IP-10 is 4.4 nM.

The various embodiments of the present invention is not to be limited in scope by the specific embodiments described herein. Indeed, various modifications of the various embodiments of the invention in addition to those described herein will become apparent to those skilled in the art from the foregoing description and accompanying figures. Such modifications are intended to fall within the scope of the appended claims. Moreover, all embodiments described herein are considered to be broadly applicable and combinable with any and all other consistent embodiments, as appropriate.

Various publications are cited herein, the disclosures of which are incorporated by reference in their entireties.

The invention claimed is:

1. A method for treating cancer in a subject in need thereof, which comprises:
    applying peripheral blood from the subject to an apheresis column loaded with a solid support comprising one or more binding reagents capable of specifically binding to chemokine receptor CCR7 immobilized directly or indirectly on the support, whereby one or more cells expressing chemokine receptor CCR7 are removed from the peripheral blood of the subject; and
    returning the applied peripheral blood back to the subject, whereby the cancer is treated, and wherein the cancer is a leukemia.

2. The method of claim 1, wherein the levels of circulating tumour cells are reduced in the subject.

3. The method of claim 1, wherein the incidence of tumour metastasis is reduced in the subject.

4. The method of claim 1, wherein the leukemia is selected from chronic lymphocytic leukemia, chronic myeloid leukemia, acute myeloid leukemia (AML), acute lymphoblastic leukemia (ALL), and leukemic phase of lymphoma.

5. The method of claim 1, wherein the binding reagent is an agonist or an antagonist of CCR7.

6. The method of claim 1, wherein the binding reagent is an antibody or a chemokine.

7. The method of claim 6, wherein the chemokine is selected from CCL19 and CCL21.

8. The method of claim 7, wherein the chemokine is CCL19 (MIP-3b) or CCL21 (SLC) and the chemokine receptor is CCR7.

9. The method of claim 1, wherein the one or more cells are B cells, regulatory T cells, tumour cells, central memory T lymphocytes, or regulatory T lymphocytes.

10. The method of claim 1, wherein the subject has increased levels of expression of CCR7 as compared to a subject that does not have cancer.

11. The method of claim 1, wherein 20-90% of the subject's blood is applied to the column in a single treatment.

12. The method of claim 1, wherein treating cancer comprises:
   (a) reducing levels of circulating tumour cells in the subject,
   (b) reducing the incidence of tumour metastasis in the subject,
   (c) removing regulatory T lymphocytes from the peripheral blood of the subject,
   (d) debulking in Acute Myeloid Leukemia (AML), or Acute Lymphoblastic Leukemia (ALL) in the subject before harvest for autologous bone marrow/stem cell transplantation, or
   (e) any combination of (a)-(d).

* * * * *